(12) United States Patent
Mauger et al.

(10) Patent No.: US 8,163,768 B2
(45) Date of Patent: Apr. 24, 2012

(54) 1,4-DIHYDROPYRIDINE-FUSED HETEROCYCLES, PROCESS FOR PREPARING THE SAME, USE AND COMPOSITIONS CONTAINING THEM

(75) Inventors: Jacques Mauger, Tucson, AZ (US); Anil Nair, Tucson, AZ (US); Nina Ma, Tucson, AZ (US); Kirsten Bjergarde, Tucson, AZ (US); Bruno Filoche-Romme, Creteil (FR); Odile Angouillant-Boniface, Paris (FR); Serge Mignani, Chatenay-Malabry (FR); Jean-Christophe Carry, Saint Maur des Fosses (FR); Francois Clerc, Antony (FR); Herve Minoux, Thiais (FR); Laurent Schio, Marolles en Brie (FR); Cecile Combeau, Fontenay aux Roses (FR)

(73) Assignee: Aventis Pharma S.A.., Antony (FR)

( * ) Notice: Subject to any disclaimer, the term of this patent is extended or adjusted under 35 U.S.C. 154(b) by 1075 days.

(21) Appl. No.: 12/014,516

(22) Filed: Jan. 15, 2008

(65) Prior Publication Data

US 2008/0261969 A1 Oct. 23, 2008

Related U.S. Application Data

(63) Continuation of application No. PCT/IB2006/002734, filed on Jul. 18, 2006.

(30) Foreign Application Priority Data

Jul. 20, 2005 (EP) .................................. 05291558

(51) Int. Cl.
A61K 31/437 (2006.01)
A61K 31/4375 (2006.01)
C07D 471/14 (2006.01)
(52) U.S. Cl. ............................. 514/293; 546/82; 546/84
(58) Field of Classification Search .................... 546/82, 546/84; 514/293
See application file for complete search history.

(56) References Cited

U.S. PATENT DOCUMENTS

| 2002/0007059 A1 | 1/2002 | Drizin et al. |
| 2004/0198981 A1 | 10/2004 | Husson et al. |
| 2005/0019854 A1 | 1/2005 | Gross et al. |

FOREIGN PATENT DOCUMENTS

| WO | WO 99/30710 | | 6/1999 |
| WO | WO 01/36422 | A1 | 5/2001 |
| WO | WO 01/66544 | A2 | 9/2001 |
| WO | WO 02/062795 | A2 | 8/2002 |
| WO | WO 02/083936 | A2 | 10/2002 |
| WO | WO 02/094835 | A1 | 11/2002 |
| WO | WO 2004/005323 | A2 | 1/2004 |
| WO | WO 2004/099190 | A1 | 11/2004 |
| WO | WO 2005/016245 | A2 | 2/2005 |

OTHER PUBLICATIONS

Banker, G.S. et al, "Modern Pharmaceutics, 3ed.", Marcel Dekker, New York, 1996, pp. 451 and 596.*
Wolff, Manfred E. "Burger's Medicinal Chemistry, 5ed, Part I", John Wiley & Sons, 1995, pp. 975-977.*
Dermer, Bio/Technology, 1994, 12:320.*
Chemical Abstracts, CAS Registry No. 327089-03-2, Ambinter Stock Screening Collection; Jul. 3, 2005.
Chemical Abstracts, CAS Registry No. 380210-97-9, Ambinter Stock Screening Collection; Jul. 3, 2005.
Chemical Abstracts, CAS Registry No. 380211-89-2, Ambinter Stock Screening Collection; Jul. 3, 2005.
Chemical Abstracts, CAS Registry No. 380450-96-4, Ambinter Stock Screening Collection; Jul. 3, 2005.
Chemical Abstracts, CAS Registry No. 380450-97-5, Ambinter Stock Screening Collection; Jul. 3, 2005.
Chemical Abstracts, CAS Registry No. 380453-29-2, Ambinter Stock Screening Collection; Jul. 3, 2005.
Chemical Abstracts, CAS Registry No. 380459-24-5, Ambinter Stock Screening Collection; Jul. 3, 2005.
Chemical Abstracts, CAS Registry No. 438027-48-6, Ambinter Stock Screening Collection; Jul. 3, 2005.
Chemical Abstracts, CAS Registry No. 439095-18-8, Bionet Building Blocks; May 25, 2005.
Chemical Abstracts, CAS Registry No. 565201-72-1, Ambinter Stock Screening Collection; Jul. 3, 2005.
Chemical Abstracts, CAS Registry No. 654633-97-3, Ambinter Stock Screening Collection; Jul. 3, 2005.
Chemical Abstracts, CAS Registry No. 654633-98-4, ChemDiv, Inc. Product Library; Apr. 25, 2003.
Chemical Abstracts, CAS Registry No. 654633-99-5, ChemDiv, Inc. Product Library; Apr. 25, 2003.
Chemical Abstracts, CAS Registry No. 654634-00-1, ChemDiv, Inc. Product Library; Apr. 25, 2003.
Chemical Abstracts, CAS Registry No. 654634-01-2, Ambinter Stock Screening Collection; Jul. 3, 2005.
Chemical Abstracts, CAS Registry No. 748145-12-2, Ambinter Stock Screening Collection; Jul. 3, 2005.

(Continued)

Primary Examiner — Rita Desai
(74) Attorney, Agent, or Firm — Scully, Scott, Murphy & Presser, P.C.

(57) ABSTRACT

This invention relates to compounds of formula (I)

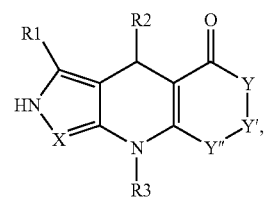

to processes for the preparation of such compounds, to pharmaceutical compositions comprising such compounds, and to methods of treatment comprising administering of such compounds.

17 Claims, No Drawings

OTHER PUBLICATIONS

Chemical Abstracts, CAS Registry No. 748145-19-9, Ambinter Stock Screening Collection; Jul. 3, 2005.
Chemical Abstracts, CAS Registry No. 748146-30-7, Ambinter Stock Screening Collection; Jul. 3, 2005.
Chemical Abstracts, CAS Registry No. 748146-41-0, Ambinter Stock Screening Collection; Jul. 3, 2005.
Chemical Abstracts, CAS Registry No. 748146-73-8, Ambinter Stock Screening Collection; Jul. 3, 2005.
Chemical Abstracts, CAS Registry No. 867135-51-1, Interchim Intermediates; Jan. 18, 2005.
Drizin et al, Structure-Activity Studies for a Novel Series of Tricyclic Dihydropyrimidines as KATP Channel Openers (KCOs), Bioorganic & Medicinal Chemistry Letters; 12 (2002) pp. 1481-1484.
Kada et al, Furan derivatives. Part CXV. Condensation reactions of 5-arylthio- and 5-heteroarylthio-2-furaldehydes with nitromethane, Collection of Czechoslovak Chemical Communications; (1978), 43(8), pp. 2037-40.
Kada et al, Reaction of 2-cyano-3-(4,5-dibromo-2-furyl)-2-propenenitrile and methyl 2-cyano-3-(4,5-dibromo-2-furyl)-2-propenenitrile and methyl 2-cyano-3-(4,5-dibromo-2-furyl)-2-propenoate with nucleophiles, Collection of Czechoslovak Chemical Communications; (1984), 49(4), pp. 984-991.
Quiroga et al, Regioselective Synthesis of 4,7,8,9-tetrahydro-2H-pyrazolo[3,4-b]quinolin-5(6H)-ones. Mechanism and Structural Analysis, Tetrahedron; 57 (2001) pp. 6947-6953.

* cited by examiner

1,4-DIHYDROPYRIDINE-FUSED HETEROCYCLES, PROCESS FOR PREPARING THE SAME, USE AND COMPOSITIONS CONTAINING THEM

The present invention relates in particular to novel chemical compounds, particularly novel substituted dihydropyridine-fused heterocycles, to the compositions containing them and to their use as medicinal products.

More particularly, the invention relates to specific partially saturated pyrrole or pyrazole fused 5-oxo-hexahydronaphthyridines or 5-oxo-hexahydroquinolines, exhibiting anticancer activity via modulation of the activity of proteins, in particular of kinases.

To date, most of the commercial compounds used in chemotherapy are cytotoxic agents, which poses considerable problems of side effects and of tolerance in patients. These effects may be limited in so far as the medicinal products used act selectively on cancer cells, with exclusion of healthy cells. One of the solutions for limiting the adverse effects of chemotherapy may therefore consist in using medicinal products which act on metabolic pathways or elements constituting these pathways, expressed mainly in cancer cells, and which would be expressed very little or not at all in healthy cells.

Protein kinases are a family of enzymes which catalyze the phosphorylation of hydroxyl groups of specific protein residues such as tyrosine, serine or threonine residues. Such phosphorylations can widely modify the function of proteins; thus, protein kinases play an important role in regulating a large variety of cell processes, including in particular metabolism, cell proliferation, cell differentiation, cell migration or cell survival. Among the various cellular functions in which the activity of a protein kinase is involved, certain processes represent attractive targets for treating cancer-related diseases and also other diseases.

Thus, one of the objects of the present invention is to provide compositions having anticancer activity, acting in particular with respect to kinases. Among the kinases for which modulation of the activity is sought, Aurora A and B are preferred. The use of Aurora kinase inhibitors as anticancer agents has recently been reviewed in "aurora kinase inhibitors as anticancer agents, N. Keen and S. Taylor, Nature Reviews 2004, 4, 927-936.

Many proteins involved in chromosome segregation and spindle assembly have been identified in yeast and *drosophila*. Disorganization of these proteins leads to non-segregation of chromosomes and to monopolar or disorganized spindles. Among these proteins, some kinases, including Aurora and Ipl1, which originate respectively from *drosophila* and *S. cerevisiae*, are necessary for chromosome segregation and separation of the centrosome. A human analogue of yeast Ipl1 has recently been cloned and characterized by various laboratories. This kinase, called Aurora2, Aurora A, STK15 or BTAK, belongs to the serine/threonine kinase family. Bischoff et al. have shown that Aurora2 is oncogenic and is amplified in human colorectal cancers (EMBO J, 1998, 17, 3052-3065). Examples of this have also been shown in cancers involving epithelial tumours, such as breast cancer.

It is worth mentioning that one of the advantages of the current invention is to provide quite selective compounds. Indeed, these compounds mostly avoid inhibiting kinases involved in cellular transcription, which may result in severe side effects and/or higher toxicity towards quiescent cells. As a result, the compounds according to the invention mostly avoid inhibiting CDK7 and/or CDK9 kinases, or at least the inhibition ratio is in favour of an Aurora kinase.

The following corresponds to Applicant's believed closest prior art search for compounds of formulas (I) and (II) according to the invention:

Drizin, Irene; Holladay, Mark W.; Yi, Lin; Zhang, Henry Q.; Gopalakrishnan, Sujatha; Gopalakrishnan, Murali; Whiteaker, Kristi L.; Buckner, Steven A.; Sullivan, James P.; Carroll, William A. "Structure-Activity studies for a novel series of tricyclic dihydropyrimidines as KATP channel openers (KCOs)". Bioorganic & Medicinal Chemistry Letters (2002), 12(11), 1481-1484.

Quiroga, J et al. Tetrahedron (2001) 57(32), 6947-6953 <<Regioselective synthesis of 4,7,8,9-tetrahydro-2H-pyrazolo[3,4-b]quinolin5(6H)-ones"

Drizin, Irene; Altenbach, Robert J.; Carroll, William A. "Preparation of tricyclic dihydropyrazolone and tricyclic dihydroisoxazolone as potassium channel openers". U.S. Pat. Appl. Publ. 2002007059 A1 WO 2001066544 A2.

"New substituted benzimidazole derivatives are C-JUN N-terminal kinase inhibitors useful in the prevention and/or treatment of e.g. inflammatory diseases, autoimmune diseases, destructive bone disorders and neurodegenerative diseases". WO 200499190 A1.

Gross, Rene; Lajoix, Anne-Dominique; Ribes, Gerard. <<Novel methods for screening inhibitors of the interaction of rat neuronal nitric oxide synthase and its cognate inhibitor". WO02/083936 A2.

Kohara, T; Fukunaga K, Fujimura M, Hanano T; Okabe H.: "dihydropyrazolopyridine compounds and pharmaceutical use thereof". WO02/062795 A2

Olsson L., Naranda T "Affinity small molecules for the EPO receptor" WO2004/005323 A2

Drees, B E; Chakravarty L; Prestwich G D; Dorman G; Kavecz M; Lukacs A; Urge L.; Darvas F; Rzepecki P W; Fergusson C G "Compound having inhibiting activity of phosphatidylinositol 3-kinase and methods of use thereof WO2005/016245 A2

Kada, Rudolf; Knoppova, Viera; Kovac, Jaroslav; Cepec, Pavel. "Reaction of 2-cyano-3-(4,5-dibromo-2-furyl)-2-propenenitrile and methyl 2-cyano-3-(4,5-dibromo-2-furyl)-2-propenenitrile and methyl 2-cyano-3-(4,5-dibromo-2-furyl)-2-propenoate with nucleophiles". Collection of Czechoslovak Chemical Communications (1984), 49(4), 984-91.

Kada, Rudolf; Kovac, Jaroslav. "Furan derivatives. Part CXV. Condensation reactions of 5-arylthio- and 5-heteroarylthio-2-furaldehydes with nitromethane". Collection of Czechoslovak Chemical Communications (1978), 43(8), 2037-40.

Now, surprisingly, and according to a first aspect of the invention, it has been found that products corresponding to the general formula (I) below are of particular interest for inhibiting an Aurora kinase:

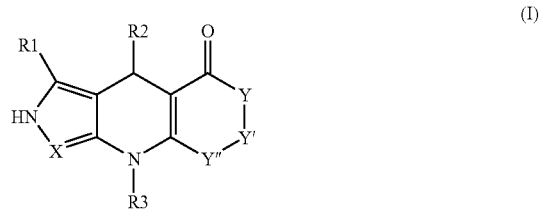

wherein:
R1 represents H, alkyl, aryl, heteroaryl, substituted alkyl, substituted aryl, or substituted heteroaryl;

R2 represents substituted aryl or substituted heteroaryl;
R3 represents H or R4;
X is N or CR7;
Y, Y' and Y":
  (i) each independently represents a substituent selected among CH₂, CHR5, CR5R6, C=O, O, S, NH, and NR7; or
  (ii) together represent a substituent selected among —CH₂—O—(C=O)—, —(CH₂)₄— and —(CH₂)₂— chain moiety;
R4 and R7 each independently represents a substituent selected among: R8, —COOR8, COR8, and CONHR8;
R5 and R6 each independently represent R8;
R8 represents H or optionally substituted: -alkyl, -alkyl-alkylene, -alkylene, -heterocycloalkyl, -cycloalkyl, -aryl, -heteroaryl, -alkyl-heterocycloalkyl, -alkyl-cycloalkyl, -alkyl-aryl, or -alkyl-heteroaryl, -alkyl-NRaRb. Ra and Rb each independantly represents H or Alkyl,
being understood that R1 is H when X is N and Y' is CR5R6.

The formula (I) comprises all the possible tautomeric forms;

Preferably, the object of the invention is a compound of formula (I) wherein R1 is H Preferably, the object of the invention is a compound of formula (I) wherein R3 is H.

Preferably, the object of the invention is a compound of formula (I) wherein Y and Y" are CH₂.

Preferably, the object of the invention is a compound of formula (I) wherein Y' is selected among CH₂, CHCH₃, C(CH₃)₂, CH-aryl, CH-heteroaryl, CH-(substituted aryl), CH-(substituted heteroaryl), NH and NR7.

Preferably, the object of the invention is a compound of formula (I) wherein R2 is a substituted heteroaryl when X is N and Y' is CR5R6

Preferably, the object of the invention is a compound of formula (Ia)

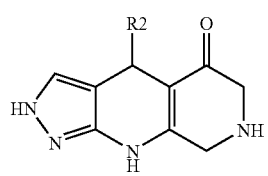

corresponding to a compound of formula (I) with X=N, R1=H, R3=H, Y=Y"=CH2 and Y'=NH, wherein R2 is a substituted aryl.

More preferably, the object of the invention is a compound of formula (Ia) as defined above wherein R2 is a substituted heteroaryl group.

Preferably, the object of the invention is a compound of formula (I'a)

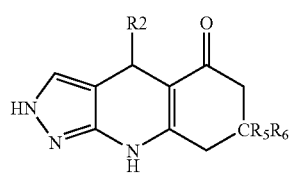

corresponding to compound of formula (I) with X=N, R1=H, R3=H, Y=Y"=CH2 and Y'=CR5R6, R5 and R6 are as defined above, wherein R2 is a substituted aryl group.

More preferably, the object of the invention is a compound of formula (I'a) as defined above wherein R2 is a substituted heteroaryl group.

Preferably, the object of the invention is a compound of formula (Ib)

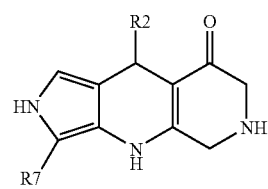

corresponding to compound of formula (I) with X=CR7, R1=H, R3=H, Y=Y"=CH2 and Y'=NH, R7 being as defined above, wherein R2 is a substituted aryl group.

More preferably, the object of the invention is a compound of formula (Ib) as defined above wherein R2 is a substituted heteroaryl group.

Preferably, the object of the invention is a compound of formula (I'b)

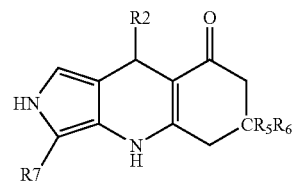

corresponding to compound of formula (I) with X=CHR7, R1=H, R3=H, Y=Y"=CH2 and Y'=CR5R6, R5, R6 and R7 being are as defined above, wherein R2 is a substituted aryl group.

Most preferably, the object of the invention is a compound of formula (I'b) as defined above wherein R2 is a substituted heteroaryl group.

More particularly, the object of the invention is a compound of formulae (Ia) or (Ib), wherein R2 is a substituted phenyl or heteroaryl group; wherein the substitution includes one to four substituents chosen among halogen, alkyl, OH, OR8, CH₂—OR8, SH, SR8, NH₂, NHR8, CONHR8, CONHCH2R8, NHCOR8, NHCONHR8, SO₂⁻NHR8, phenyl not substituted or substituted by alkyl, OH, or halogen, wherein R8 is as defined above.

More particularly R8 is chosen among phenyl and heteroaryl, not substituted or substituted with one to four substituents independently chosen among F, Cl, Br, OH, SH, CF₃, OCF₃, OCH₃, SCF₃, SCH₃, OCHF₂, OCH₂F, SCH₂F, (C1-C6)-alkyl, O-allyl, phenyl, and phenyl substituted with halogen.

More particularly, the object of the invention is a compound of formulae (I'a) or (I'b) wherein R2 is a substituted heteroaryl group; wherein the substitution includes one to four substituents chosen among halogen, alkyle, OH, OR8, CH₂—OR8, SH, SR8, NH₂, NHR8, CONHR8, CONHCH2R8, NHCOR8, NHCONHR8, SO₂³¹ NHR8, phenyl not substituted or substituted by alkyl, OH, or halogen, wherein R8 is as defined above.

More particularly R8 is phenyl or heteroaryl, not substituted or substituted with one to four substituents independently chosen among F, Cl, Br, OH, SH, $CF_3$, $OCF_3$, $OCH_3$, $SCF_3$, $SCH_3$, $OCHF_2$, $OCH_2F$, $SCH_2F$, (C1-C6)-alkyl, O-allyl, phenyl, and phenyl substituted with halogen More particularly, the object of the invention is a compound of formulae (I), (Ia), (Ib), (I'a) and (I'b), wherein R2 is heteroaryl substituted by SR8

More particularly, the object of the invention is a compound of formulae (I), (Ia), (Ib), (I'a) and (I'b), wherein R2 is furyl or thienyl substituted by SR8

More particularly, R8 is a benzimidazolyl or a imidazolyl not susbtituted or substituted by one to four substituents independently chosen among F, Cl, Br, OH, SH, $CF_3$, $OCF_3$, $OCH_3$, $SCF_3$, $SCH_3$, $OCHF_2$, $OCH_2F$, $SCH_2F$, (C1-C6)-alkyl, O-allyl, phenyl, and phenyl substituted with halogen.

More particularly, the object of the invention is a compound of formula (I), (I'a) and (I'b) wherein R5 and R6 are both Hydrogen or both methyl.

More particularly, the object of the invention is a compound of formula (I), (I'a) and (I'b) wherein R5 is Hydrogen and R6 is a (C1-C6)-alkyl substituted or not substituted or a phenyl substituted or not substituted.

More particularly, the object of the invention is a compound of formula (I), (Ib) and (I'b) wherein R7 is a —$CO_2Et$ group More particularly, the object of the invention is a compound prepared according to the examples of the experimental part hereafter.

A compound according to the first aspect of the invention may be in the racemic form, enriched in one enantiomer, enriched in one diastereoisomer, its tautomers, its prodrugs and its pharmaceutically acceptable salts.

In the products of formula (I) as defined above and below, the alkyl, cycloalkyl, heterocycloalkyl, aryl, heteroaryl, aralkyl or heteroaralkyl radicals can be optionally substituted with one or more radicals, which may be identical or different, chosen from halogen atoms; and the radicals: hydroxyl; cycloalkyl containing at most 6 ring members; acyl containing at most 7 carbon atoms; cyano; nitro; free, salified or esterified carboxyl; tetrazolyl; —NH2, —NH(alk), —N(alk)(alk); $SO_2$—NH—CO—NH-alkyl; $SO_2$—NH—CO—NH-phenyl; —C(O)—$NH_2$; —C(O)—NH(alk); —C(O)—N(alk)(alk), —NH—C(O)-(alk), —N(alk)-C(O)-(alk); thienyl; phenyl, alkyl, alkylthio, alkoxy and phenoxy, themselves optionally substituted with one or more radicals chosen from halogen atoms and hydroxyl, alkoxy, alkyl, —NH2, —NH(alk) and —N(alk)(alk) radicals.

More particularly, in the products of formula (I) as defined above and below, the alkyl, cycloalkyl, heterocycloalkyl, aryl, heteroaryl, aralkyl or heteroaralkyl radicals can be optionally substituted with one or more radicals, which may be identical or different, chosen from halogen atoms; and the radicals: hydroxyl; free, salified or esterified carboxyl; —NH2, —NH(alk), —N(alk)(alk); phenyl, alkyl and alkoxy, themselves optionally substituted with one or more radicals chosen from halogen atoms and hydroxyl, alkoxy, alkyl, —NH2, —NH(alk) and —N(alk)(alk) radicals.

Even more particularly, in the products of formula (I) as defined above and below, the alkyl, alkenyl, alkynyl, cycloalkyl, heterocycloalkyl, aryl, heteroaryl, aralkyl or heteroaralkyl radicals can be optionally substituted with one or more radicals, which may be identical or different, chosen from halogen atoms and hydroxyl and alkoxy radicals.

In the products of formula (I) and below, the terms indicated have the meanings which follow:

the term "halogen" refers to fluorine, chlorine, bromine or iodine atoms, and preferably fluorine, chlorine or bromine atoms;

the term "alkyl radical" refers to a linear or branched radical containing at most 12 carbon atoms, chosen from methyl, ethyl, propyl, isopropyl, butyl, isobutyl, sec-butyl, tert-butyl, pentyl, isopentyl, sec-pentyl, tert-pentyl, neopentyl, hexyl, isohexyl, sec-hexyl and tert-hexyl radicals and also heptyl, octyl, nonyl, decyl, undecyl and dodecyl radicals, and also the linear or branched positional isomers thereof. Mention is more particularly made of alkyl radicals containing at most 6 carbon atoms, and in particular methyl, ethyl, propyl, isopropyl, n-butyl, isobutyl, tert-butyl, linear or branched pentyl, linear or branched hexyl radicals;

the term "alkoxy radical", that can be represented for example by OR, refers to a linear or branched radical containing at most 12 carbon atoms, and preferably 6 carbon atoms, chosen, for example, from methoxy, ethoxy, propoxy, isopropoxy, linear, secondary or tertiary butoxy, pentoxy, hexoxy or heptoxy radicals, and also the linear or branched positional isomers thereof;

the term "alkylthio" or "alkyl-S—", that can be represented for example by SR3, refers to a linear or branched radical containing at most 12 carbon atoms, and is in particular methylthio, ethylthio, isopropylthio and heptylthio radicals. In the radicals comprising a sulphur atom, the sulphur atom can be oxidized to an SO or S(O)2 radical;

the term "acyl radical" (COR) refers to a linear or branched radical containing at most 12 carbon atoms in which the radical R is a hydrogen atom, or an alkyl, cycloalkyl, cycloalkenyl, cycloalkyl, heterocycloalkyl or aryl radical, these radicals having the values indicated above and being optionally substituted as indicated: mention is, for example, made of formyl, acetyl, propionyl, butyryl or benzoyl radicals, or else valeryl, hexanoyl, acryloyl, crotonoyl or carbamoyl radicals;

the term "cycloalkyl radical" refers to a monocyclic or bicyclic carbocyclic radical containing from 3 to 10 ring members and refers in particular to cyclopropyl, cyclobutyl, cyclopentyl and cyclohexyl radicals;

the term "cycloalkylalkyl radical" refers to a radical in which cycloalkyl and alkyl are chosen from the values indicated above: this radical thus refers, for example, to cyclopropylmethyl, cyclopentylmethyl, cyclohexylmethyl and cycloheptylmethyl radicals;

the term "acyloxy radical" is intended to mean acyl-O-radicals in which acyl has the meaning indicated above: mention is, for example, made of acetoxy or propionyloxy radicals;

the term "acylamino radical" is intended to mean acyl-N-radicals in which acyl has the meaning indicated above;

the term "aryl radical" refers to unsaturated carbocyclic radicals that are monocyclic or comprise condensed rings. As examples of such an aryl radical, mention may be made of phenyl, naphthyl, anthrenyl and phenanthrenyl radicals: mention is more particularly made of the phenyl radical;

the term "arylalkyl" is intended to mean radicals resulting from combination of the alkyl radicals mentioned above, that are optionally substituted, and the aryl radicals also mentioned above, that are optionally substituted: mention is, for example, made of benzyl, phenylethyl, 2-phenethyl, triphenylmethyl or naphthalenemethyl radicals;

the term "heterocyclic radical" refers to a saturated (heterocycloalkyl) or unsaturated (including heteroaryl) (all unsaturated heteroary are not necessarily aromatic e.g. chromanyl, tetrahydroquinolyl) carbocyclic radical comprising at most 6 ring members interrupted with one or more identical or different hetero atoms chosen from oxygen, nitrogen or sulphur atoms.

As heterocyclic radicals, mention may in particular be made of dioxolane, dioxane, dithiolane, thiooxolane, thiooxane, oxiranyl, oxolanyl, dioxolanyl, piperazinyl, piperidyl, pyrrolidinyl, imidazolidinyl, pyrazolidinyl, morpholinyl, tetrahydrofuryl, tetrahydrothienyl, chromanyl, dihydrobenzofuryl, indolinyl, piperidyl, perhydropyranyl, pyrindolinyl, tetrahydroquinolinyl, tetrahydroisoquinolinyl, benzoxazinyl or thioazolidinyl radicals, all these radicals being optionally substituted.

Among the heterocyclic radicals, mention may in particular be made of optionally substituted piperazinyl, optionally substituted piperidyl, optionally substituted pyrrolidinyl, imidazolidinyl, pyrazolidinyl, morpholinyl or thioazolidinyl radicals.

The term "heterocycloalkylalkyl radical" is intended to mean radicals in which the heterocycloalkyl and alkyl residues have the meanings above;

among the heteroaryl radicals with 5 ring members, mention may be made of furyl radicals, such as 2-furyl and 3-furyl, thienyl radicals, such as 2-thienyl and 3-thienyl, and pyrrolyl, diazolyl, thiazolyl, thiadiazolyl, thiatriazolyl, isothiazolyl, oxazolyl, oxadiazolyl, 3- or 4-isoxazolyl, imidazolyl, pyrazolyl and isoxazolyl, triazolyl, triazinyl and tetrazolyl radicals.

Among the heteroaryl radicals with 6 ring members, mention may in particular be made of pyridyl radicals such as 2-pyridyl, 3-pyridyl and 4-pyridyl and pyrimidyl, pyrimidinyl, pyridazinyl and pyrazinyl radicals.

As condensed heteroaryl radicals containing at least one hetero atom chosen from sulphur, nitrogen and oxygen, mention may, for example, be made of benzothienyl such as 3-benzothienyl, benzofuryl, benzothiazolyl, indolyl, benzimidazolyl, benzoxazolyl, thionaphthyl, indolyl, isoindolyl, indazolyl, pyridopyrrolyl, pyridopyrazolyl, naphtimidazolyl, imidazoquinolyl, benzisothiazolyl, benzisoxazolyl, purinyl, quinolinyl, isoquinolinyl and naphthyridinyl.

Among the condensed heteroaryl radicals, mention may more particularly be made of benzothienyl, benzofuranyl, indolyl or quinolinyl, benzimidazolyl, benzothiazolyl, indolizinyl, isoquinolinyl, quinazolinyl groups, these radicals being optionally substituted as indicated for the heteroaryl radicals.

The addition salts with inorganic or organic acids of the products of formula (I) can, for example, be the salts formed with hydrochloric acid, hydrobromic acid, hydriodic acid, nitric acid, sulphuric acid, phosphoric acid, propionic acid, acetic acid, trifluoroacetic acid, formic acid, benzoic acid, maleic acid, fumaric acid, succinic acid, tartaric acid, citric acid, oxalic acid, glyoxylic acid, aspartic acid, ascorbic acid, alkylmonosulphonic acids such as, for example, methanesulphonic acid, ethanesulphonic acid or propanesulphonic acid, alkyldisulphonic acids such as, for example, methanedisulphonic acid or alpha,beta-ethanedisulphonic acid, arylmonosulphonic acids such as benzenesulphonic acid, and aryldisulphonic acids.

According to a second aspect, the invention is about a pharmaceutical composition comprising a product according to its first aspect, in combination with a pharmaceutically acceptable excipient.

Therefore, the present invention also relates to therapeutic compositions containing a compound according to the invention, in combination with a pharmaceutically acceptable excipient depending on the chosen mode of administration. The pharmaceutical composition may be in solid or liquid form or in the form of liposomes.

Among the solid compositions that may be mentioned are powders, gelatin capsules and tablets. Among the oral forms, solid forms protected against the acidic medium of the stomach may also be included. The supports used for the solid forms consist in particular of mineral supports such as phosphates or carbonates, or organic supports such as lactose, celluloses, starch or polymers. The liquid forms consist of solutions, suspensions or dispersions. They contain, as dispersive support, either water or an organic solvent (ethanol, NMP or the like) or mixtures of surfactants and solvents or of complexing agents and solvents.

The liquid forms will preferably be injectable and, as a result, will have a formulation that is acceptable for such a use.

Acceptable routes of administration by injection include intravenous, intraperitoneal, intramuscular and subcutaneous routes, the intravenous route being preferred.

The administered dose of the compounds of the invention will be adapted by the practitioner depending on the route of administration to the patient and the condition of said patient.

The compounds of the present invention may be administered alone or as a mixture with other anticancer agents. Among the possible combinations, that may be mentioned are:

alkylating agents and especially cyclophosphamide, melphalan, ifosfamide, chlorambucil, busulfan, thiotepa, prednimustine, carmustine, lomustine, semustine, steptozotocin, decarbazine, temozolomide, procarbazine and hexamethylmelamine;

platinum derivatives especially such as cisplatin, carboplatin or oxaliplatin;

antibiotic agents especially such as bleomycin, mitomycin or dactinomycin;

antimicrotubule agents especially such as vinblastine, vincristine, vindesine, vinorelbine or taxoids (paclitaxel and docetaxel);

anthracyclines especially such as doxorubicin, daunorubicin, idarubicin, epirubicin, mitoxantrone or losoxantrone;

group I and II topoisomerases such as etoposide, teniposide, amsacrine, irinotecan, topotecan and tomudex;

fluoropyrimidines such as 5-fluorouracil, UFT or floxuridine;

cytidine analogues such as 5-azacytidine, cytarabine, gemcitabine, 6-mercaptomurine or 6-thioguanine;

adenosine analogs such as pentostatin, cytarabine or fludarabine phosphate;

methotrexate and folinic acid;

various enzymes and compounds such as L-asparaginase, hydroxyurea, trans-retinoic acid, suramin, dexrazoxane, amifostine, herceptin and estrogen and androgen hormones;

antivascular agents such as combretastatin or colchicine derivatives and prodrugs thereof.

It is also possible to combine the compounds of the present invention with a radiation treatment. These treatments may be administered simultaneously, separately or sequentially. The treatment will be adapted to the patient to be treated by the practitioner.

According to a third aspect, the invention is about the use of a product according to its first aspect, as a medicament Therefore, a product in accordance with the invention may be used for the manufacture of a medicinal product that is useful for treating a pathological condition, in particular a cancer.

According to a third aspect, the invention is about the use of a product according to its first aspect, as an agent that inhibits an Aurora kinase.

According to its third aspect, the invention is about the use of a product according to its first aspect, as an agent that inhibits the proliferation of tumour cells.

According to a fourth aspect, the invention is about the use of a product according to its first aspect, for producing a medicinal product of use in treating a pathological condition, especially a cancerous condition.

As an inhibitor of tumour cell proliferation, the said compound may be used in the prevention and treatment of leukaemias, both primary and metastatic solid tumours, carcinomas and cancers, in particular: breast cancer; lung cancer; cancer of the small intestine; cancer of the colon and rectum; cancer of the respiratory tracts, of the oropharynx and the hypopharynx; cancer of the oesophagus; cancer of the liver, stomach cancer, cancer of the biliary canals, cancer of the biliary vesicle, cancer of the pancreas; cancers of the urinary tracts including the kidney, urothelium and bladder; cancers of the female genital tract including cancer of the uterus, the neck of the uterus, the ovaries, chloriocarcinoma and trophoblastoma; cancers of the male genital tract including cancer of the prostate, of the seminal vesicles, the testicles, germinal cell tumours; cancers of the endocrinal glands including cancer of the thyroid, the pituitary, of the adrenal glands; skin cancers, including haemangiomas, melanomas, sarcomas, including Kaposi's sarcoma; tumours of the brain, nerves, eyes, meninges, including astrocytomas, gliomas, glioblastomas, retinoblastomas, neurinomas, neuroblastomas, schwannomas, meningiomas, malignant haematopoietic tumours; leukaemias (Acute Lymphocytic Leukemia (ALL), Acute Myeloid Leukemia (AML), Chronic Myeloid Leukemia (CML), Chronic lymphocytic leukemia (CLL)), chloromas, plasmocytomas, T or B cell leukaemias, non Hodgkins or Hodgkins lymphomas, myelomas, and various malignant haemopathies.

According to a fifth aspect, the invention is about a process of preparation of a tricyclic dihydropyridine of formula (I) by the following general procedure:

A mixture of 1 equivalent of pyrazole or pyrrole (X=N or CR7), 1 equivalent of aldehyde R2-CHO and 1 equivalent of diketo derivative is heated at reflux temperature in an alcohol such as ethanol or 1-butanol for ½ to several hours. The solution is cooled down to room temperature. The desired compound is either isolated by filtration or the solvent is removed under vacuum. If needed, the crude product is purified on silica gel or using preparative high performance liquid chromatography (HPLC).

When Y' is N-Boc the product is deprotected using a solution of trifluoroacetic acid in dichloromethane (50/50) or a solution of hydrochloric acid in dioxane.

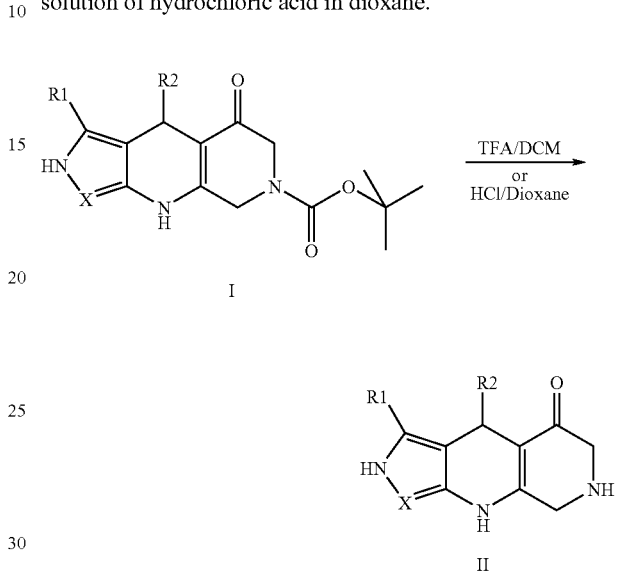

Therefore the invention is also about a process of preparation of compounds of formula (I) characterized in that a/ an aminopyrazole (X=NH) or an aminopyrrole (X=CR7) derivative of formula (II)

b/ an aldehyde of formula (III)

R2-CHO and c/ a diketone derivatives of formula (IV)

wherein R1, R2, R7, Y, Y', Y" are as defined in claim 1, are mixed in an alcoholic solvent at reflux temperature to produce a crude compound of formula (I) that is then optionally submitted to a deprotection step and/or a purification step and/or a salification step.

A/ General Procedure for the Preparation of N-Substituted Tricyclic Dihydropyridines
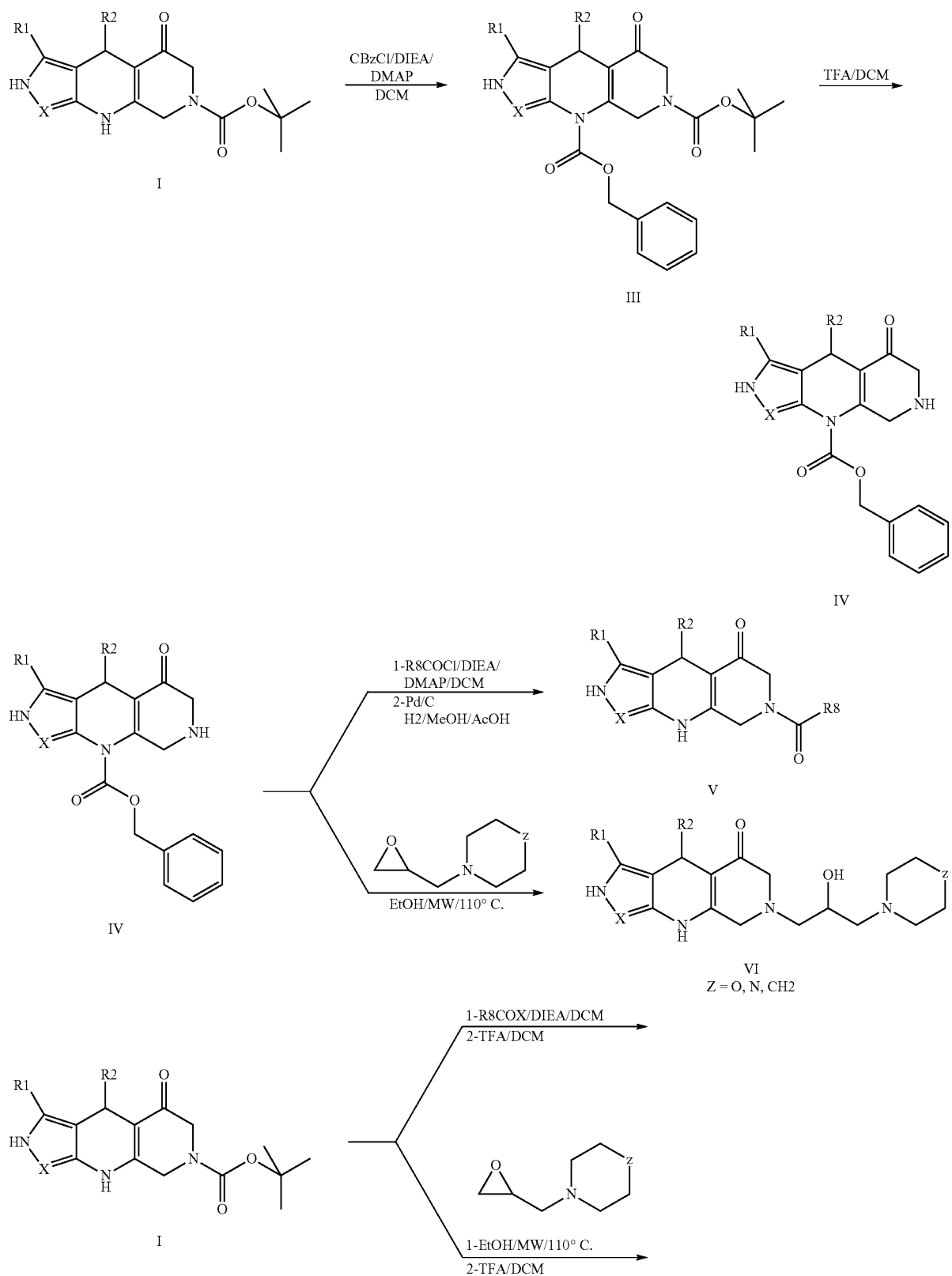

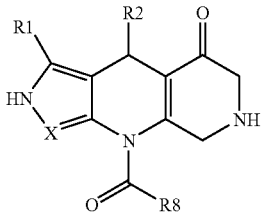

7 VII

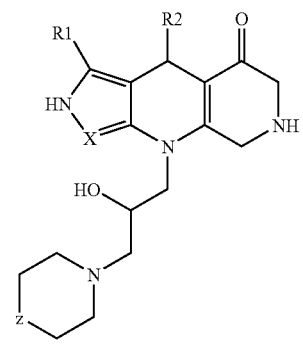

VIII

The tricyclic compound I in solution in dichloromethane (DCM) is treated by with 2 equivalents of benzyloxycarbonyl chloride, 2 equivalents of diisopropylethylamine (DIEA) and a catalytic amount of 4-dimethylaminopyridine (DMAP) at room temperature for 24 hours. The reaction mixture is poured into a 10% solution of potassium hydrogenosulfate and extracted with DCM. The organic phase is washed with water, dried over magnesium sulfate ($MgSO_4$) and concentrated under vacuum. The crude products are purified on silica gel to give the Cbz-protected derivative III.

The Boc protection is removed by treating compound III with a mixture of trifluoroacetic acid (TFA) and DCM (50/50) at room temperature for 1 hour. After evaporation of the solvent, the crude product is purified on silica gel to give IV.

Acyl derivatives of general formula V are prepared in 2 steps. The compounds of formula IV are first acylated by various acyl chlorides in DCM using DIEA and a catalytic amount of DMAP. The reaction mixture is stirred overnight at room temperature and poured into water. The mixture is extracted with DCM. The organic phase is washed with water, dried over $MgSO_4$ and concentrated under vacuum. The compounds V are purified using preparative HPLC.

Alkyl derivatives of general formula VI are prepared from compounds IV using the corresponding epoxides in ethanol. The solution is either heated at reflux temperature for 2 hours or irradiated with microwaves at 110° C. for 10 minutes. The mixture is poured in water and extracted with DCM. The DCM solution is washed with water, dried over $MgSO_4$ and concentrated. The resulting product is hydrogenated with Pd/C under hydrogen atmosphere. After filtration on Celite® and evaporation, the crude product is purified using preparative liquid chromatography coupled to mass spectrometry (LC/MS).

Acyl derivatives of general formula VII are prepared by direct acylation of I with acyl chlorides as described for III or with acid anhydrides in DCM using DIEA for 2 hours at room temperature. The mixture is poured in 10% potassium hydrogenosulfate solution and extracted with DCM. The organic solution is washed with water, dried over $MgSO_4$ and concentrated. The crude product is treated directly with a solution of TFA/DCM (50/50) for 1 hour at room temperature. The crude products are purified using preparative LC/MS to give VII.

Alkyl derivatives of general formula VIII are obtained by treating in a microwave apparatus at 150° C. compound I with the corresponding epoxide in N,N-dimethylformamide (DMF). The intermediate is purified using preparative HPLC. The resulting derivative is deprotected with a TFA/DCM solution (50/50). The crude product is purified by preparative LC/MS.

B/ General Procedure for the Preparation of Non-Commercially Available Aldehydes R2-CHO of Formula (III)

Aldehydes of General Structures IX:

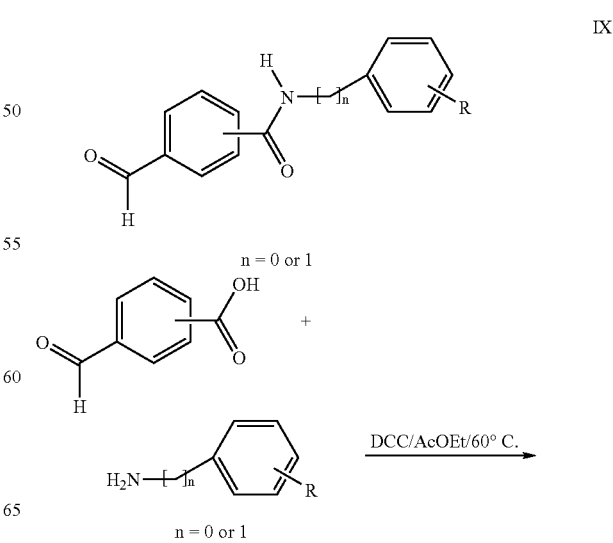

-continued

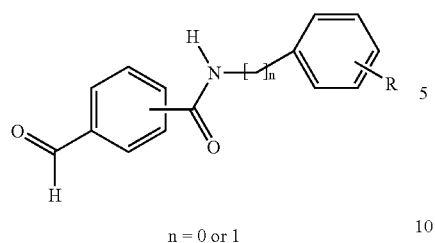

n = 0 or 1

A mixture of 1 equivalent of formyl benzoic acid and 1 equivalent of aniline or benzylamine derivative in ethyl acetate (AcOEt) is treated with dicyclohexylcarbodiimide (DCC) at 60° C. for several hours. The mixture is poured in HCl 1N. The organic phase is collected and successively washed with water, a solution of sodium bicarbonate and brine. The solution is dried over MgSO$_4$ and concentrated. The crude products are purified on silica gel when needed.

Aldehydes of General Structure X:

X

A mixture of 1 equivalent of aminobenzaldehyde and 1 equivalent of benzoyl chloride derivative in DMF is treated with 2 equivalents of DIEA under microwave irradiation at 110° C. for 10 minutes. Compounds X generally precipitate and are collected by filtration.

Aldehydes of General Structure XI:

XI

-continued

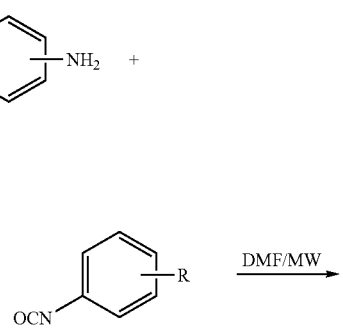

A mixture of 1 equivalent of aminobenzaldehyde and 1 equivalent of phenylisocyanate derivative in DMF is treated under microwave irradiation at 110° C. for 10 minutes. Compounds XI generally precipitate and are collected by filtration.

Aldehydes of General Structure XII:

XII

A mixture of 1 equivalent of chlorosulfonylbenzaldehyde and 1 equivalent of aniline derivative in dichloro-1,2-ethane (DCE) is treated with an excess of pyridine for several hours. The mixture is poured into a 10% HCl solution and extracted with DCM. The organic phase is washed with brine, dried over MgSO$_4$ and concentrated. The crude products are purified on silica gel to give aldehydes XII.

Aldehydes of Structure XV and XVI:

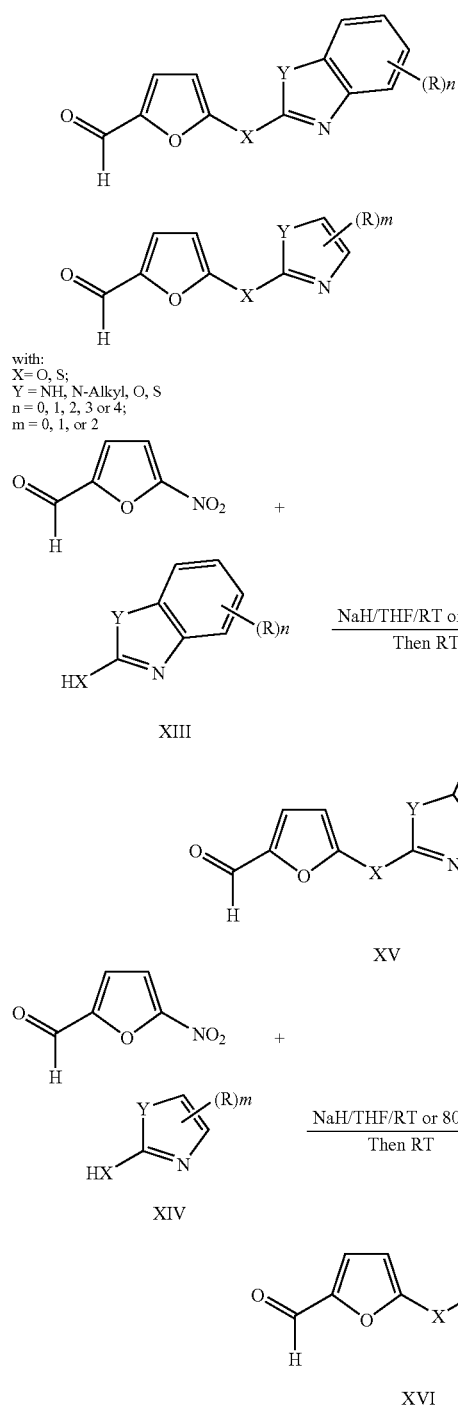

with:
X= O, S;
Y = NH, N-Alkyl, O, S
n = 0, 1, 2, 3 or 4;
m = 0, 1, or 2

To a solution of 1 equivalent of the compound of general formula XIII or XIV in dry tetrahydrofuran (THF) is added 1 to 1.5 equivalent of NaH suspension at room temperature. The mixture is stirred at room temperature until gas evolution has ceased and optionally heated at 80° C. for 30 minutes. The reaction mixture is cooled down to room temperature and a solution of 1 equivalent of 5-nitro-furaldehyde in THF is added. The reaction mixture is stirred until completion and then poured into water and extracted with ethyl acetate. The organic phase is washed with brine, dried over MgSO$_4$ and concentrated. When needed the crude products are purified via column chromatography on silica gel or via recrystallization to yield compounds of formula XV or XVI.

Aldehydes of General Structure XVII and XVIII:

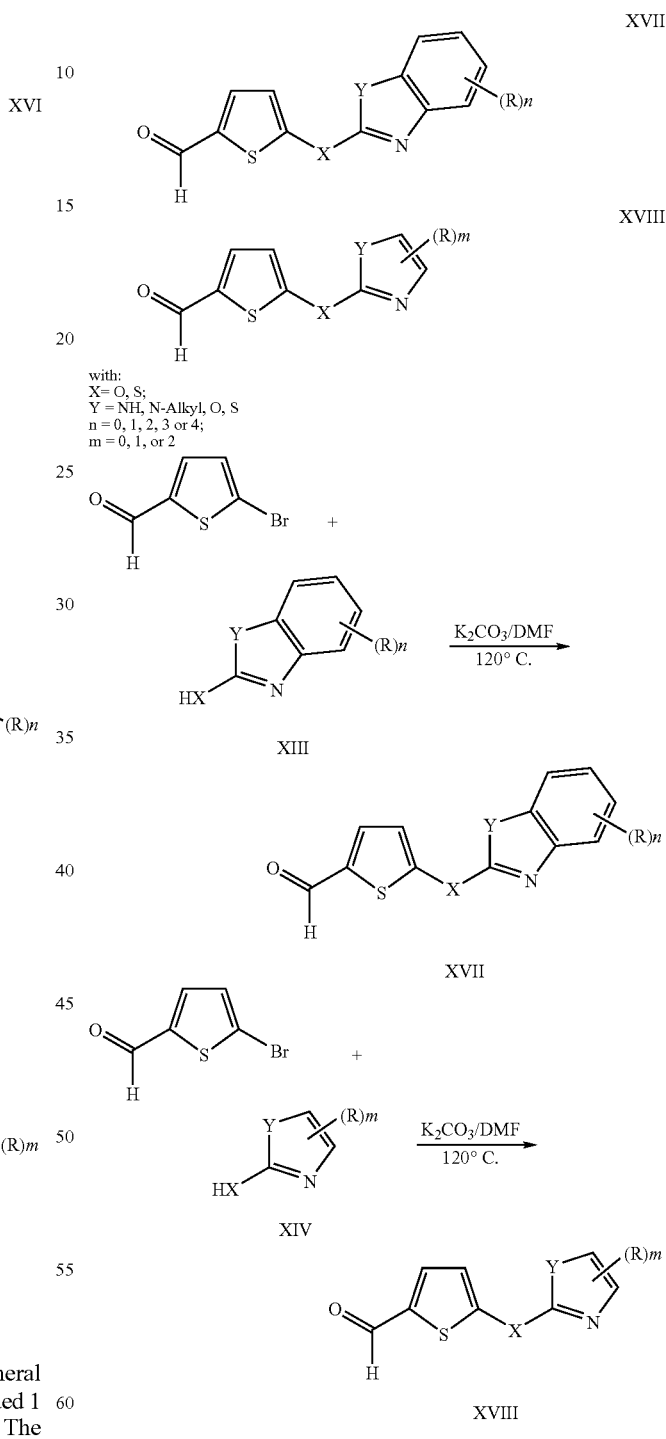

with:
X= O, S;
Y = NH, N-Alkyl, O, S
n = 0, 1, 2, 3 or 4;
m = 0, 1, or 2

A mixture of 1 equivalent of 5-bromothiophene-2-carboxaldehyde, 1 equivalent of the compounds of general formula XIII or XIV and 2 equivalents of potassium carbonate are heated at 120° C. until completion of the reaction. Then the reaction mixture is poured in water and extracted with ethyl acetate. The organic phase is washed with brine, dried over MgSO$_4$ and concentrated. The crude products are purified on silica gel when needed to yield compounds XVII or XVIII.

Aldehydes of General Structure XIX:

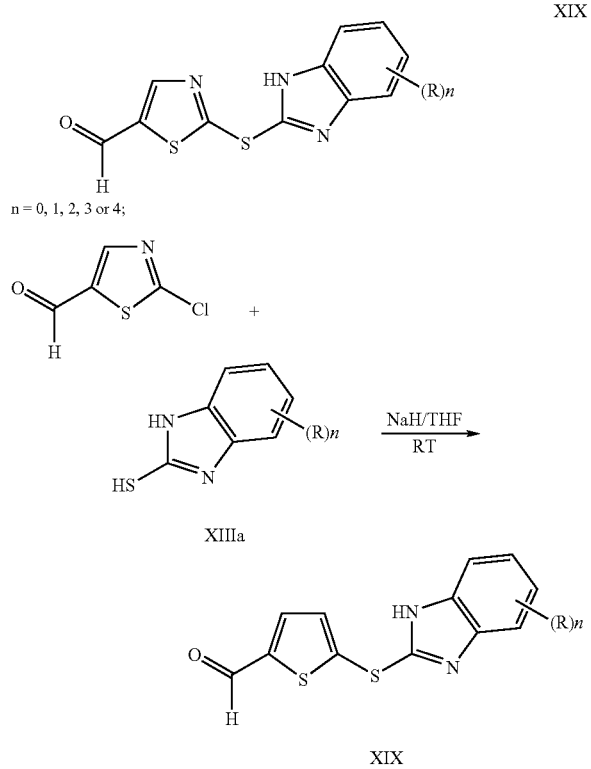

n = 0, 1, 2, 3 or 4;

To a solution of 1 equivalent of the compound of general formula XIIIa in dry THF is added 1 to 1.5 equivalent of NaH suspension at room temperature. The mixture is stirred at room temperature until gas evolution has ceased. A solution of 1 equivalent of 2-chloro-1,3-thiazole-5-carbaldehyde in THF is added. The reaction mixture is stirred until completion and then poured into water and extracted with ethyl acetate. The organic phase is washed with brine, dried over MgSO$_4$ and concentrated. An alternative workup can be filtration of the reaction mixture. The solid is then diluted with water and extracted with ethyl acetate and with dichloromethane. The organic extracts are combined, dried on MgSO$_4$ and concentrated. When needed the crude products are purified via column chromatography on silica gel or via recrystallization to yield compounds of formula XIX.

Experimental Part
Methods:
Analytical LC/MS Method A:

Analytical LC/MS analyses were conducted using Shimadzu LC-10AD HPLC pumps; a Gilson 215 well plate autosampler; a Shimadzu SPD-10A UV detector; the mass spectrometer was a PE Sciex API 100LC.instrument model on a YMC basic S5 column eluted with a gradient of acetonitrile (ACN) containing 0.1% TFA in water at a flow rate of 0.1 ml/min, gradient details are given for each example. Compounds eluting off the column are detected by electrospray ionisation mass spectrometry (EIMS).

Analytical LC/MS Method B:

Analysis is conducted on Waters model ZQ mass spectrometer working in positive and negative ion electrospray mode (mass range=100-1200 amu) fitted on a Agilent HP1100 HPLC instrument. Separation is done on a Waters Xbridge C18 column (3×50 mm, 2.5 µm particle diameter) maintained at a temperature of 60° C. and eluted by a gradient of acetonitrile in water containing 0.1% (v/v) formic acid at a flow rate of 1.1 ml/min. The gradient has the following shape: 5 to 100% acetonitrile in 5 minutes, maintain 100% acetonitrile for 0.5 minute, then back to 5% acetonitrile in 1 minute. Total run time is 7 minutes. In addition to mass spectrometry, UV diode array detection is performed at wavelengths=210 to 400 nM and evaporative light scattering is carried out using a Sedere Sedex 85 instrument.

Analytical LC/MS Method C:

Analysis is conducted on Waters model ZQ mass spectrometer working in positive and negative ion electrospray mode (mass range=100-1200 amu) fitted on a Waters Acquity UPLC Instrument. Separation is done on a Waters UPLC BeH C18 column (2.1×50 mm, 1.7 µm particle diameter) maintained at a temperature of 55° C. and eluted by a gradient of acetonitrile in water containing 0.1% (v/v) formic acid at a flow rate of 1.2 ml/min. The gradient has the following shape: 5 to 100% acetonitrile in 3 minutes, then back to 5% acetonitrile in 1 minute. Total run time is 4.5 minutes. In addition to mass spectrometry, UV diode array detection is performed at wavelengths=210 to 400 nM.

Preparative LC/MS Method A:

Preparative LC/MS separation were carried out on Waters HPLC instruments: 515 HPLC Pump; 2525 Binary Gradient Module; 2487 DAD (Dual Absorbance Detector); 2767 sample Manager connected with a Micromass mass spectrometer. Products were separated on a YMC Combi Prep Pro C18 column eluted with a gradient acetonitrile containing 0.1% TFA in water containing 0.1% TFA of flow rate 32 ml/min. For each separation gradient programation is adapted on the basis of an analytical LC/MS chromatogram of the sample.

Preparative LC/MS Method B:

Compounds are purified by LC/MS using a Waters FractionLynx system composed of a Waters model 600 gradient pump, a Waters model 515 regeneration pump, a Waters Reagent Manager make-up pump, a Waters model 2700 autoinjector, two Rheodyne model LabPro switches, a Waters model 996 photodiode array detector, a Waters model ZMD mass spectrometer and a Gilson model 204 fraction collector. The instrument is controlled by a Waters FractionLynx software. At the output of the separating column the flow is split to the 1/1000 ratio using a LC Packing AccuRate splitter; 1/1000 of the flow is mixed with methanol (0.5 ml/min. flow rate) and sent to the detectors, this flow is split again: ¾ of the flow is sent to the photodiode array detector and ¼ to the mass spectrometer; the rest of the output of the column (999/1000) is sent to the fraction collector where flow wis directed normally to waste unless expected mass signal is detected by the FractionLynx software. The FractionLynx software is supplied with molecular formulas of expected compounds and trigger the collection of compounds when mass signal corresponding to [M+H]$^+$ and [M+Na]$^+$ are detected. In certain cases (depending on analytical LC/MS result, when [M+2H]$^{++}$ is detected as an intense ion) the FractionLynx software is additionally supplied with calculated half molecular weight (MW/2), in these conditions collection is also triggered when mass signal corresponding to [M+2H]$^{++}$ and [M+Na+H]$^{++}$ are detected. Compounds are collected in tarred glass tubes. After collection, solvent is evaporated in a Jouan model RC 10.10 centrifuge evaporator and the weight of compound is determined by weighing of the tubes after solvent evaporation. Column and gradient details are given for each example in the following part.

EXAMPLE 1

4-(4-Hydroxy-3-methyl-phenyl)-2,4,6,7,8,9-hexahydro-pyrazolo[3,4-b]-1,7-naphthyridin-5-one; compound with trifluoro-acetic acid

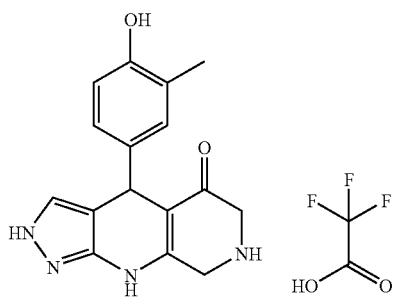

To a mixture of 213 mg of N-Boc-3,5-diketopiperidine (1 mmole) (N-Boc-3,5-diketopiperidine can be prepared according to patent WO 06003096 A1) and 83 mg of 3-aminopyrazole (1 mmole) in 5 ml of ethanol is added 136.2 mg of 4-hydroxy-3-methylbenzaldehyde (1 mmole). The mixture is heated at reflux temperature for 2 hours and cooled down to room temperature. The precipitate is collected by filtration and washed with ethanol to give 316 mg of pale yellow solid (yield=80%). Analytical LC/MS method A: Retention time (RT)=3.8 min (2-85% ACN/H$_2$O gradient over 7 min) EIMS ([M+H]+): 397.

N-Boc-3,5-diketopiperidine can be prepared according to patent WO 2006003096 A1.

100 mg of the isolated compound is dissolved in 5 ml of DCM and treated with 5 ml of TFA for 1 hr at room temperature. After evaporation of the solvent the crude product is directly purified using preparative reverse phase HPLC. 50 mg of desired compound are isolated after lyophilisation of the fractions (yield=50%). Analytical LC/MS method A: (2-85% ACN/H$_2$O gradient over 7 min) EIMS ([M+H]+): 297. RT=2.31

H$^1$NMR (D$_6$-DMSO) (300 MHz, Brucker instrument): 1.99 (s, 3H); 3.64 (AB, 2H); 4.09 (AB, 2H); 4.97 (s, 1H); 6.52 (d, 1H); 6.76 (d, 1H); 6.80 (s, 1H); 7.31 (s, 1H); 10.4 (s, 1H).

EXAMPLE 2

4-[3-(4-Chloro-phenoxy)-phenyl]-2,4,6,7,8,9-hexahydro-pyrazolo[3,4-b]-1,7-naphthyridin-5-one; compound with trifluoro-acetic acid

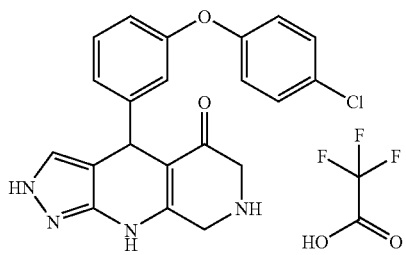

To a mixture of 107 mg of N-Boc-3,5-diketopiperidine (0.5 mmole) and 42 mg of 3-aminopyrazole (0.5 mmole) in 2.5 ml of ethanol is added 0.116 ml of 3-(4-chlorophenoxy)-benzaldehyde (0.5 mmole). The mixture is heated at reflux temperature for ½ hour and cooled down to room temperature. The solution is concentrated under vacuum. The resulting oily residue is dissolved in 2.5 ml of DCM and treated with 2.5 ml of TFA at room temperature for 1 hour. After evaporation of the solvent, the crude product is directly purified using preparative reversed phase HPLC resulting in 70 mg of white solid after lyophilisation of the fractions (yield=31%). Analytical LC/MS method A: (2-85% ACN/H$_2$O gradient over 7 min) EIMS ([M+H]+): 393. RT=3.91

H$^1$NMR (D$_6$-DMSO) (300 MHz Brucker instrument): 3.70 (AB, 2H); 4.18 (AB, 2H); 5.17 (s, 1H); 6.65 (d, 1H); 6.94 (m, 4H); 7.22 (m, 1H); 7.45 (m, 3H); 9.80 (sl, 2H); 10.4 (s, 1H)

EXAMPLE 3

4-[5-(1H-Benzimidazol-2-ylsulfanyl)-furan-2-yl]-1,4,6,7,8,9-hexahydro-pyrazolo[3,4-b]quinolin-5-one

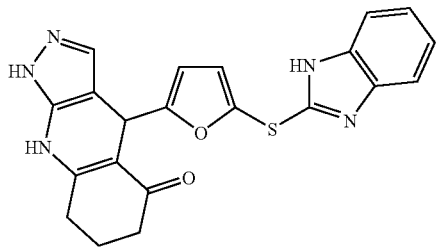

To a mixture of 225 mg of 1,3-cyclohexanedione (2 mmoles) and 183 mg of 3-aminopyrazole (2.2 mmoles) in ethanol is added 490 mg of 5-(1H-benzimidazol-2-yl-sulfanyl)-furan-2-carbaldehyde (2 mmoles). The mixture is heated at reflux temperature for ½ hour and cooled down to room temperature. The precipitate is collected by filtration and washed with ethanol to give 460 mg of pale yellow solid (yield=58%)

Analytical LC/MS method A: (2-85% ACN/H$_2$O gradient over 7 min) EIMS ([M+H]+): 404. RT=3.13 min.

H$^1$NMR (D$_6$-DMSO) (300 MHz Brucker instrument): 1.96 (m, 2H); 2.26 (m, 2H); 2.54 (m, 2H); 4.11 (s, 1H); 5.22 (s, 1H); 5.97 (s, 1H); 6.85 (s, 1H); 7.16 (m, 2H); 7.37 (m, 1H); 7.46 (s, 1H); 7.55 (m, 1H); 10.0 (s, 1H); 12.2 (s, 1H); 12.47 (s, 1H).

EXAMPLE 4

4-[5-(1H-Benzimidazol-2-ylsulfanyl)-furan-2-yl]-7,7-dimethyl-2,4,6,7,8,9-hexahydro-pyrazolo[3,4-b]quinolin-5-one

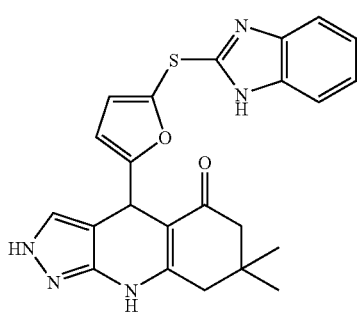

To a solution of 156 mg of dimedone (1 mmole) and 91 mg of 3-aminopyrazole (1.1 mmole) in 5 ml of ethanol is added 244 mg of 5-(1H-benzimidazol-2-ylsulfanyl)-furan-2-carbaldehyde (1 mmole). The mixture is heated at reflux for 1 hr. The solution is cooled down to room temperature and concentrated under vacuum. The crude product is directly purified on silica gel using a mixture of dichloromethane/methanol 98/2 then 96/4 as eluent.

After evaporation of the fractions, 250 mg of a pale yellow solid are isolated (58%). Analytical LC/MS method A: (2-85% ACN/H$_2$O gradient over 7 min.) EIMS ([M+H]+): 432. RT: 2.56 min H$^1$NMR (D$_6$-DMSO) (300 MHz Brucker instrument): 0.81 (s, 3H); 0.87 (s, 3H); 2.00 (AB, 2H); 2.29 (AB, 2H); 5.02 (s, 1H); 5.85 (s, 1H); 6.72

The following examples were prepared using the same procedure as for example 1:

TABLE 1

| Example number | Structure | Compound name | MW of expected compound | EIMS ([M + H]$^+$) | LC/MS RT (min) |
|---|---|---|---|---|---|
| 5 | 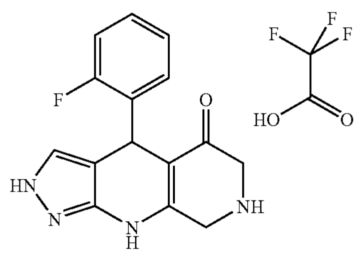 | 4-(2-Fluoro-phenyl)-2,4,6,7,8,9-hexahydro-pyrazolo[3,4-b]-1,7-naphthyridin-5-one; compound with trifluoro-acetic acid | 284.11 | 285.32 | 2.67* |
| 6 | 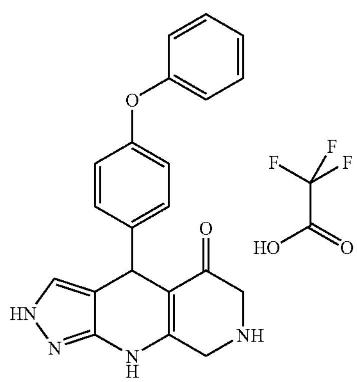 | 4-(4-Phenoxy-phenyl)-2,4,6,7,8,9-hexahydro-pyrazolo[3,4-b]-1,7-naphthyridin-5-one; compound with trifluoro-acetic acid | 358.14 | 359.43 | 3.6* |
| 7 | 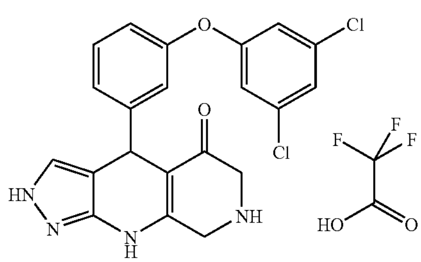 | 4-[3-(3,5-Dichloro-phenoxy)-phenyl]-2,4,6,7,8,9-hexahydro-pyrazolo[3,4-b]-1,7-naphthyridin-5-one; compound with trifluoro-acetic acid | 427.07 | 428.32 | 3.29 |
| 8 | 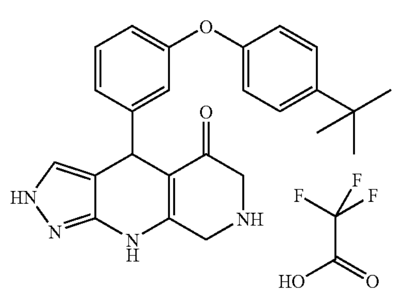 | 4-[3-(4-tert-Butyl-phenoxy)-phenyl]-2,4,6,7,8,9-hexahydro-pyrazolo[3,4-b]-1,7-naphthyridin-5-one; compound with trifluoro-acetic acid | 414.21 | 415.54 | 3.5 |

TABLE 1-continued

| Example number | Structure | Compound name | MW of expected compound | EIMS ([M + H]+) | LC/MS RT (min) |
|---|---|---|---|---|---|
| 9 | 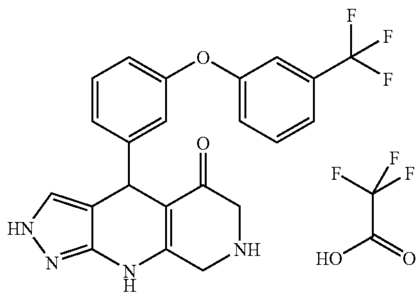 | 4-[3-(4-trifluoromethyl-phenyloxy)-phenyl]-2,4,6,7,8,9-hexahydro-pyrazolo[3,4-b]-1,7-naphthyridin-5-one; compound with trifluoro-acetic acid | 426.13 | 427.43 | 3.2 |
| 10 | 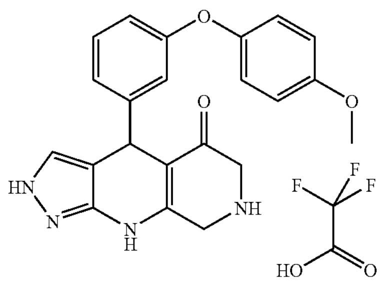 | 4-[3-(4-Methoxy-phenoxy)-phenyl]-2,4,6,7,8,9-hexahydro-pyrazolo[3,4-b]-1,7-naphthyridin-5-one; compound with trifluoro-acetic acid | 388.15 | 389.45 | 2.79 |
| 11 | 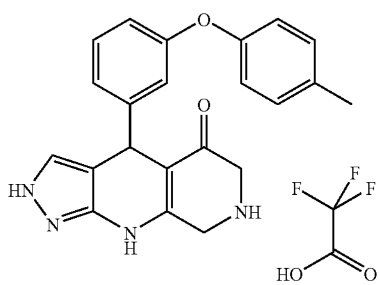 | 4-(3-p-Tolyloxy-phenyl)-2,4,6,7,8,9-hexahydro-pyrazolo[3,4-b]-1,7-naphthyridin-5-one; compound with trifluoro-acetic acid | 372.16 | 373.45 | 2.99 |
| 12 | 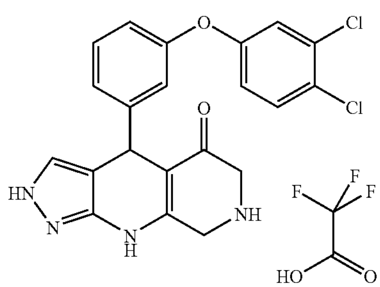 | 4-[3-(3,4-Dichloro-phenoxy)-phenyl]-2,4,6,7,8,9-hexahydro-pyrazolo[3,4-b]-1,7-naphthyridin-5-one; compound with trifluoro-acetic acid | 427.07 | 428.32 | 3.28 |
| 13 | 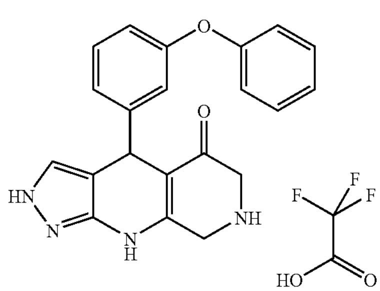 | 4-(3-Phenoxy-phenyl)-2,4,6,7,8,9-hexahydro-pyrazolo[3,4-b]-1,7-naphthyridin-5-one; compound with trifluoro-acetic acid | 358.14 | 359.43 | 2.79 |

TABLE 1-continued

| Example number | Structure | Compound name | MW of expected compound | EIMS ([M + H]⁺) | LC/MS RT (min) |
|---|---|---|---|---|---|
| 14 | 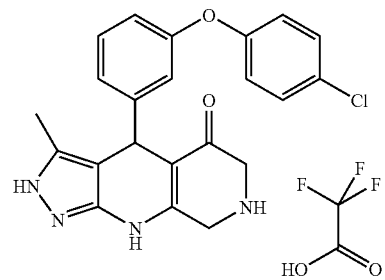 | 4-[3-(4-Chloro-phenoxy)-phenyl]-3-methyl-2,4,6,7,8,9-hexahydro-pyrazolo[3,4-b]-1,7-naphthyridin-5-one; compound with trifluoro-acetic acid | 406.12 | 407.90 | 2.87 |
| 15 | 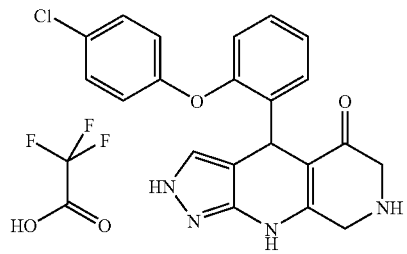 | 4-[2-(4-Chloro-phenoxy)-phenyl]-2,4,6,7,8,9-hexahydro-pyrazolo[3,4-b]-1,7-naphthyridin-5-one; compound with trifluoro-acetic acid | 392.10 | 393.87 | 2.87 |
| 16 | 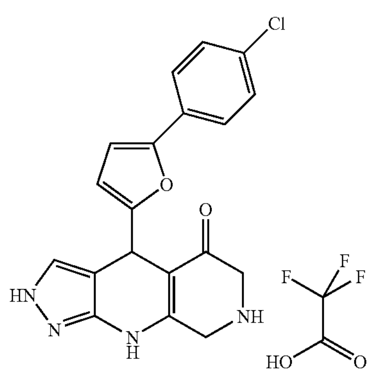 | 4-[5-(4-Chloro-phenyl)-furan-2-yl]-2,4,6,7,8,9-hexahydro-pyrazolo[3,4-b]-1,7-naphthyridin-5-one; compound with trifluoro-acetic acid | 366.09 | 367.83 | 2.6 |
| 17 | 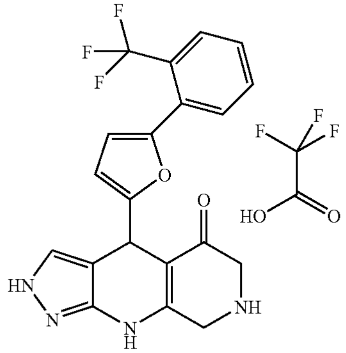 | 4-[5-(2-trifluoromethyl-phenyl)-furan-2-yl]-2,4,6,7,8,9-hexahydro-pyrazolo[3,4-b]-1,7-naphthyridin-5-one; compound with trifluoro-acetic acid | 400.11 | 401.39 | 2.7 |

TABLE 1-continued

| Example number | Structure | Compound name | MW of expected compound | EIMS ([M + H]+) | LC/MS RT (min) |
| --- | --- | --- | --- | --- | --- |
| 18 | 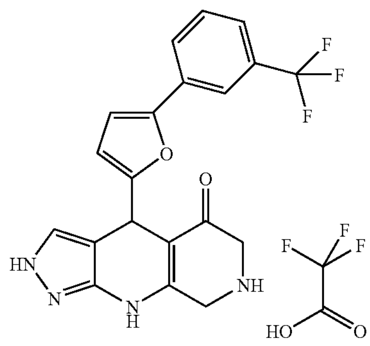 | 4-[5-(3-trifluoromethyl-phenyl)-furan-2-yl]-2,4,6,7,8,9-hexahydro-pyrazolo[3,4-b]-1,7-naphthyridin-5-one; compound with trifluoro-acetic acid | 400.11 | 401.39 | 2.85 |
| 19 | 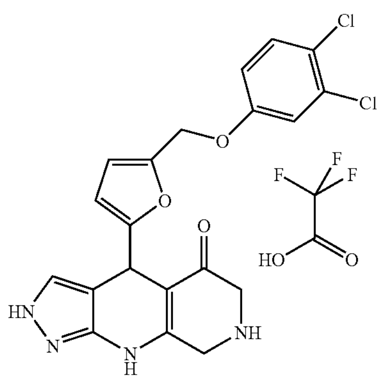 | 4-[5-(3,4-Dichloro-phenoxymethyl)-furan-2-yl]-2,4,6,7,8,9-hexahydro-pyrazolo[3,4-b]-1,7-naphthyridin-5-one; compound with trifluoro-acetic acid | 431.06 | 432.31 | 3.02 |
| 20 | 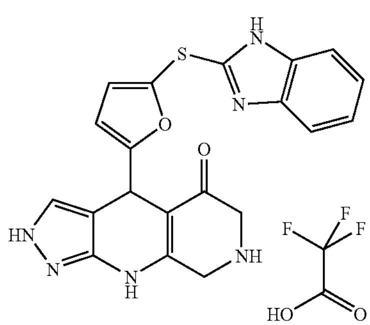 | 4-[5-(1H-Benzimidazol-2-ylsulfanyl)-furan-2-yl]-2,4,6,7,8,9-hexahydro-pyrazolo[3,4-b]-1,7-naphthyridin-5-one; compound with trifluoro-acetic acid | 404.11 | 405.48 | 1.85 |
| 21 | 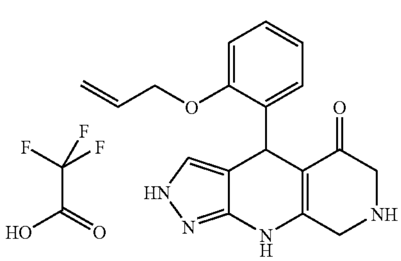 | 4-(2-Allyloxy-phenyl)-2,4,6,7,8,9-hexahydro-pyrazolo[3,4-b]-1,7-naphthyridin-5-one; compound with trifluoro-acetic acid | 322.14 | 323.39 | 2.21 |

Analytical LC/MS conditions: method A gradient 2 to 80% acetonitrile in 7 min
*Analytical LC/MS conditions: method A gradient 5 to 85% acetonitrile in 7 min The following examples were prepared using the same procedure as for example 3 or 4.

TABLE 2

| Example number | Structure | Compound name | MW of expected compound | EIMS ([M + H]⁺) | LC/MS RT (min) |
| --- | --- | --- | --- | --- | --- |
| 22 | 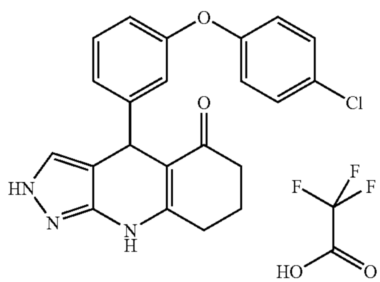 | 4-[3-(4-Chloro-phenoxy)-phenyl]-2,4,6,7,8,9-hexahydro-pyrazolo[3,4-b]quinolin-5-one; compound with trifluoro-acetic acid | 391.86 | 392.86 | 3.01 |
| 23 | 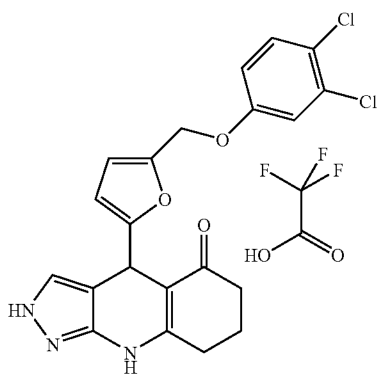 | 4-[5-(3-Chloro-phenyl)-furan-2-yl]]-2,4,6,7,8,9-hexahydro-pyrazolo[3,4-b]quinolin-5-one; compound with trifluoro-acetic acid | 365 | 366 | 3.74 |
| 24 | 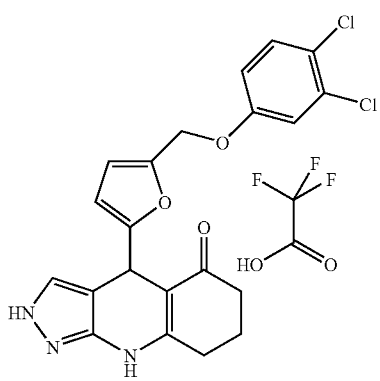 | 4-[5-(3,4-Dichloro-phenoxymethyl)-furan-2-yl]-2,4,6,7,8,9-hexahydro-pyrazolo[3,4-b]quinolin-5-one; compound with trifluoro-acetic acid | 430 | 431 | 4.06 |
| 25 | 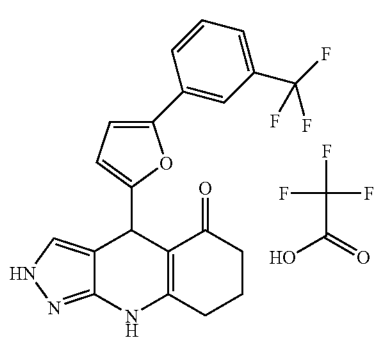 | 4-[5-(3-Trifluoromethyl-phenyl)-furan-2-yl]-2,4,6,7,8,9-hexahydro-pyrazolo[3,4-b]quinolin-5-one; compound with trifluoro-acetic acid | 399 | 400 | 3.94 |

TABLE 2-continued

| Example number | Structure | Compound name | MW of expected compound | EIMS ([M + H]+) | LC/MS RT (min) |
|---|---|---|---|---|---|
| 26 | 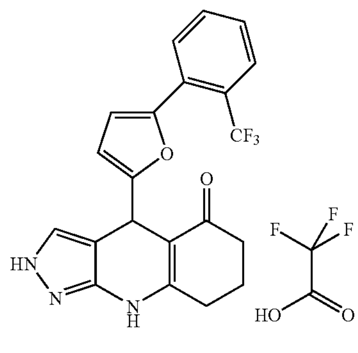 | 4-[5-(2-Trifluoromethyl-phenyl)-furan-2-yl]-2,4,6,7,8,9-hexahydro-pyrazolo[3,4-b]quinolin-5-one; compound with trifluoro-acetic acid | 399 | 400 | 3.68 |
| 27 | 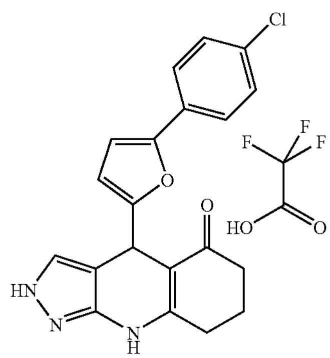 | 4-[5-(4-Chloro-phenyl)-furan-2-yl]-2,4,6,7,8,9-hexahydro-pyrazolo[3,4-b]quinolin-5-one; compound with trifluoro-acetic acid | 365 | 366 | 3.6 |
| 28 | 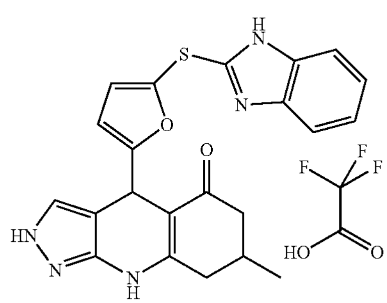 | 4-[5-(1H-Benzimidazol-2-ylsulfanyl)-furan-2-yl]-7-methyl-2,4,6,7,8,9-hexahydro-pyrazolo[3,4-b]quinolin-5-one; compound with trifluoro-acetic acid | 417 | 418 | 3.01 |
| 29 | 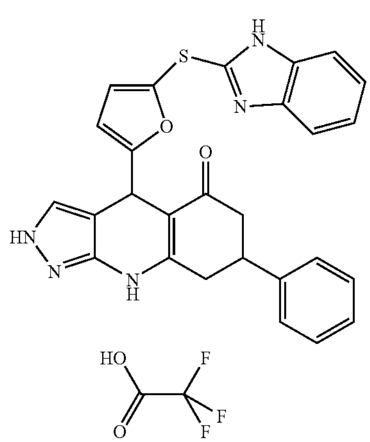 | 4-[5-(1H-Benzimidazol-2-ylsulfanyl)-furan-2-yl]-7-phenyl-2,4,6,7,8,9-hexahydro-pyrazolo[3,4-b]quinolin-5-one; compound with trifluoro-acetic acid | 479 | 480 | 3.66 |

TABLE 2-continued

| Example number | Structure | Compound name | MW of expected compound | EIMS ([M + H]+) | LC/MS RT (min) |
|---|---|---|---|---|---|
| 30 | 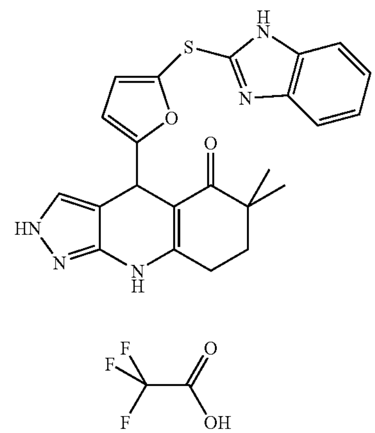 | 4-[5-(1H-Benzimidazol-2-ylsulfanyl)-furan-2-yl]-6,6-dimethyl-2,4,6,7,8,9-hexahydro-pyrazolo[3,4-b]quinolin-5-one; compound with trifluoro-acetic acid | 431 | 432 | 3.33 |
| 31 | 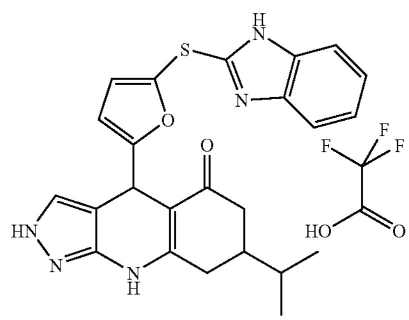 | 4-[5-(1H-Benzimidazol-2-ylsulfanyl)-furan-2-yl]-7-isopropyl-2,4,6,7,8,9-hexahydro-pyrazolo[3,4-b]quinolin-5-one; compound with trifluoro-acetic acid | 445 | 446 | 3.57 |
| 32 | 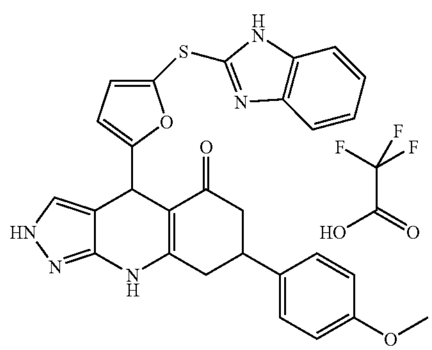 | 4-[5-(1H-Benzimidazol-2-ylsulfanyl)-furan-2-yl]-7-(4-methoxy-phenyl)-2,4,6,7,8,9-hexahydro-pyrazolo[3,4-b]quinolin-5-one; compound with trifluoro-acetic acid | 509 | 510 | 3.67 |
| 33 | 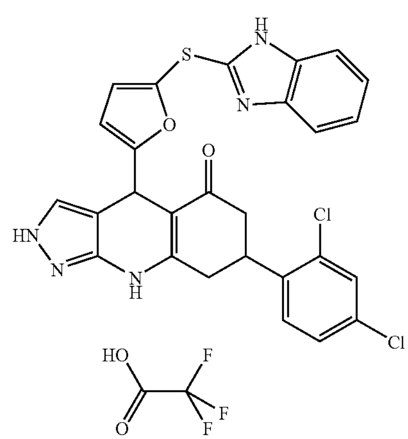 | 4-[5-(1H-Benzimidazol-2-ylsulfanyl)-furan-2-yl]-7-(2,4-dichloro-phenyl)-2,4,6,7,8,9-hexahydro-pyrazolo[3,4-b]quinolin-5-one; compound with trifluoro-acetic acid | 548 | 549 | 4.27 |

TABLE 2-continued

| Example number | Structure | Compound name | MW of expected compound | EIMS ([M + H]+) | LC/MS RT (min) |
|---|---|---|---|---|---|
| 34 | 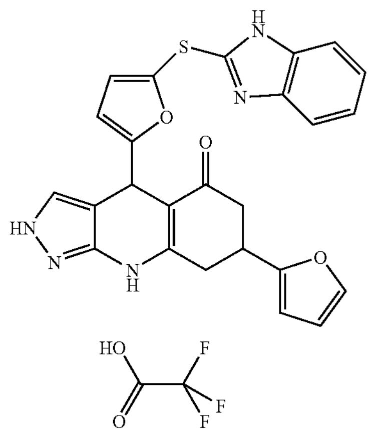 | 4-[5-(1H-Benzimidazol-2-ylsulfanyl)-furan-2-yl]-7-furan-2-yl-2,4,6,7,8,9-hexahydro-pyrazolo[3,4-b]quinolin-5-one; compound with trifluoro-acetic acid | 469 | 470 | 3.38 |
| 35 | 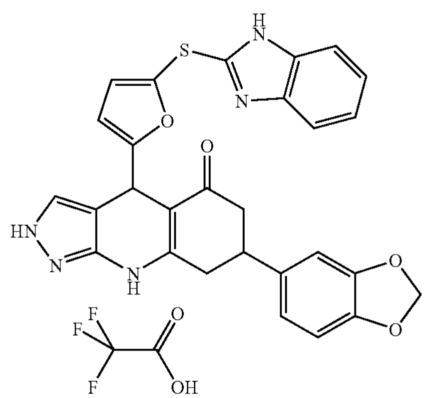 | 7-Benzo[1,3]dioxol-5-yl-4-[5-(1H-benzimidazol-2-ylsulfanyl)-furan-2-yl]-2,4,6,7,8,9-hexahydro-pyrazolo[3,4-b]quinolin-5-one; compound with trifluoro-acetic acid | 523 | 524 | 3.61 |
| 36 | 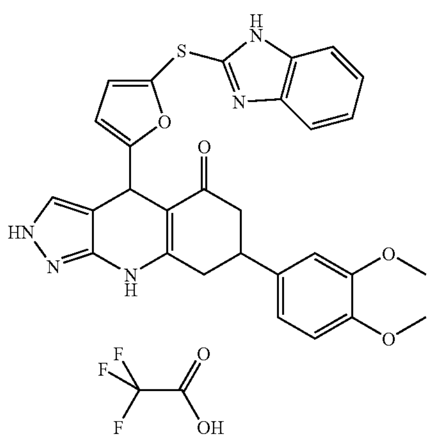 | 4-[5-(1H-Benzimidazol-2-ylsulfanyl)-furan-2-yl]-7-(3,4-dimethoxy-phenyl)-2,4,6,7,8,9-hexahydro-pyrazolo[3,4-b]quinolin-5-one; compound with trifluoro-acetic acid | 539 | 540 | 3.38 |
| 37 | 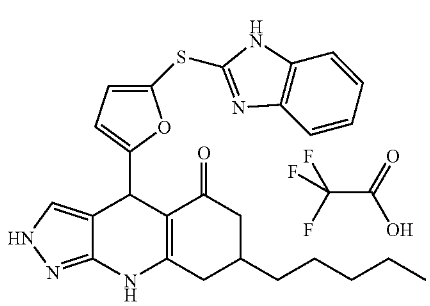 | 4-[5-(1H-Benzimidazol-2-ylsulfanyl)-furan-2-yl]-7-pentyl-2,4,6,7,8,9-hexahydro-pyrazolo[3,4-b]quinolin-5-one; compound with trifluoro-acetic acid | 473 | 474 | 4.25 |

TABLE 2-continued

| Example number | Structure | Compound name | MW of expected compound | EIMS ([M + H]+) | LC/MS RT (min) |
|---|---|---|---|---|---|
| 38 | 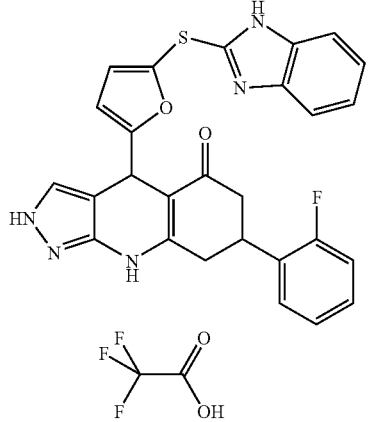 | 4-[5-(1H-Benzimidazol-2-ylsulfanyl)-furan-2-yl]-7-(2-fluoro-phenyl)-2,4,6,7,8,9-hexahydro-pyrazolo[3,4-b]quinolin-5-one; compound with trifluoro-acetic acid | 497 | 498 | 3.73 |
| 39 | 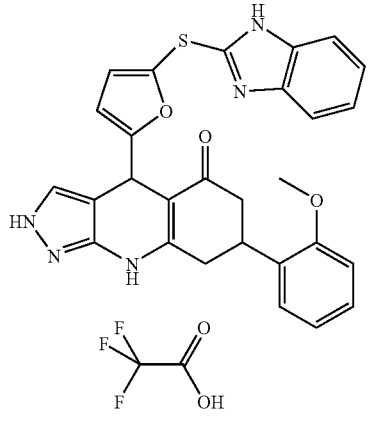 | 4-[5-(1H-Benzimidazol-2-ylsulfanyl)-furan-2-yl]-7-(2-methoxy-phenyl)-2,4,6,7,8,9-hexahydro-pyrazolo[3,4-b]quinolin-5-one; compound with trifluoro-acetic acid | 509 | 510 | 3.77 |
| 40 | 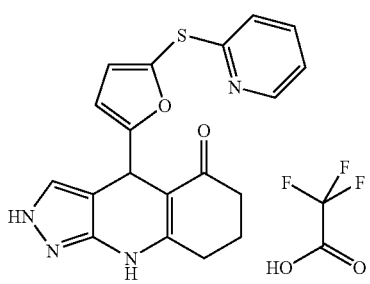 | 4-[5-Pyridin-2-ylsulfanyl)-furan-2-yl]-2,4,6,7,8,9-hexahydro-pyrazolo[3,4-b]quinolin-5-one; compound with trifluoro-acetic acid | 364 | 365 | 2.75 |

TABLE 2-continued

| Example number | Structure | Compound name | MW of expected compound | EIMS ([M + H]+) | LC/MS RT (min) |
|---|---|---|---|---|---|
| 41 | 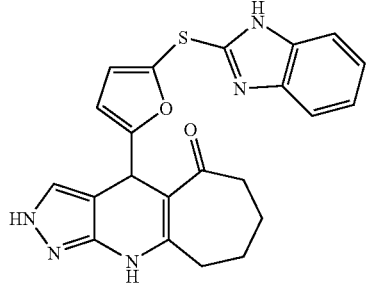 | 4-[5-(1H-Benzoimidazol-2-ylsulfanyl)-furan-2-yl]-4,6,7,8,9,10-hexahydro-2H-1,2,10-triaza-cyclohepta[f]inden-5-one; compound with trifluoro-acetic acid | 417.13 | 418.13 | 2.95 |
| 42 | 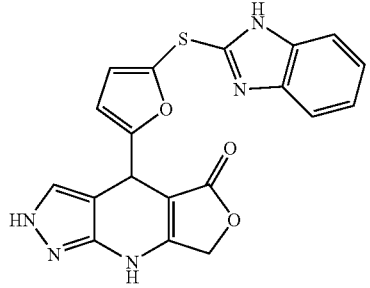 | 4-[5-(1H-Benzoimidazol-2-ylsulfanyl)-furan-2-yl]-2,4,7,8-tetrahydro-6-oxa-1,2,8-triaza-s-indacen-5-one; compound with trifluoro-acetic acid | 391.07 | 392.07 | 2.58 |
| 43 | 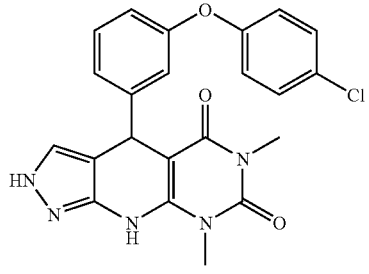 | 4-[3-(4-Chloro-phenoxy)-phenyl]-6,8-dimethyl-2,4,8,9-tetrahydro-1,2,6,8,9-pentaaza-cyclopenta[b]naphthalene-5,7-dione; compound with trifluoro-acetic acid | 435.11 | 436.11 | 2.55* |

Analytical LC/MS conditions: method A gradient 2 to 80% acetonitrile in 7 min

*Analytical LC/MS conditions: method A gradient 30 to 90% acetonitrile in 7 min

EXAMPLE 44

4-[5-(1H-Benzimidazol-2-ylsulfanyl)-furan-2-yl]-7-(tert-butyloxycarbonyl)-2,4,6,7,8,9-hexahydro-pyrazolo[3,4-b]-1,7-naphthyridin-5-one; compound with trifluoro-acetic acid

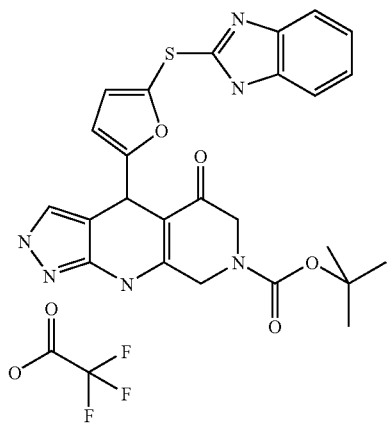

To a mixture of 443 mg of N-Boc-3,5-diketopiperidine (2.08 mmoles) and 173 mg of 3-aminopyrazole (2.08 mmoles) in 10 ml of ethanol is added 508 mg of 5-(1H-benzimidazol-2-ylsulfanyl)-furan-2-carbaldehyde 2.08 mmoles). The mixture is heated at reflux temperature for 1 hour and cooled down to room temperature. The solution is concentrated and the crude product is purified on silica gel using DCM/MeOH (95/5) as eluent. 590 mg of pale yellow solid 44 are isolated (yield=56%). Analytical LC/MS method A: (2-85% ACN/H$_2$O gradient over 7 min.) EIMS ([M+H]+): 505; RT: 3.79 min.

EXAMPLE 45

4-[5-(1H-Benzimidazol-2-ylsulfanyl)-furan-2-yl]-7-(2-hydroxy-3-piperidin-1-yl-propyl)-2,4,6,7,8,9-hexahydro-pyrazolo[3,4-b]-1,7-naphthyridin-5-one; compound with trifluoro-acetic acid

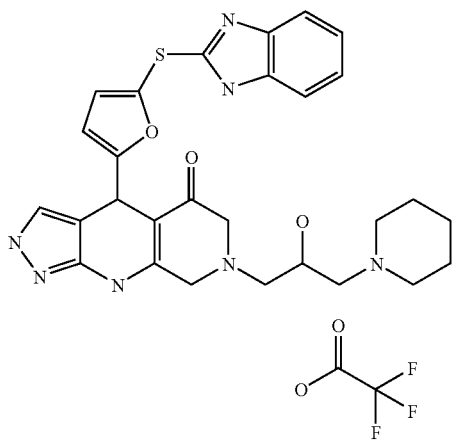

300 mg of the solid 44 (0.59 mmole) is dissolved in 4 ml of DCM and 0.184 ml of benzylchloroformate (1.3 mmole) is added, followed by 0.385 ml of DIEA (2.36 mole) and 20 mg of DMAP (0.16 mmole). The reaction mixture is shaken overnight at room temperature and then poured into 80 ml of a 10% (w/v) solution of KH$_2$SO$_4$ and extracted twice with 40 ml of ethyl acetate. The combined organic extracts are washed with brine, dried over MgSO$_4$ and concentrated. The residue is directly treated with 10 ml of a solution of TFA/DCM (50/50) for 1 hour at room temperature. The solution is concentrated under vacuum. Half of the resulting residue is dissolved in 2 ml of ethanol and directly used for the final step. The solution is treated under microwave irradiation with an excess of freshly prepared 1-oxiranylmethyl-piperidine (prepared by stirring 274 mg of epibromhydrin (2 mmoles) and 0.198 ml of piperidine (2 mmoles) in 10 ml of methanol overnight at room temperature). The mixture is irradiated under microwave for 15 minutes at 150° C. The solution is concentrated and the resulting residue is purified using a preparative HPLC. 29 mg of expected compound 45 are isolated (yield=4%). Analytical LC/MS method A: (2-85% ACN/H$_2$O gradient over 7 min.) ([M+H]+): 546. RT: 2.67 min.

EXAMPLES 46 to 50

4-[3-(4-Chloro-phenoxy)-phenyl]-7-(2-hydroxy-3-morpholin-4-yl-propyl)-2,4,6,7,8,9-hexahydro-pyrazolo[3,4-b]-1,7-naphthyridin-5-one; compound with trifluoro-acetic acid (Ex. 50)

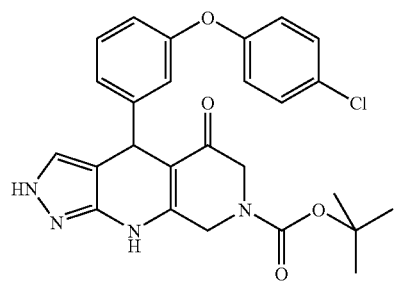

46

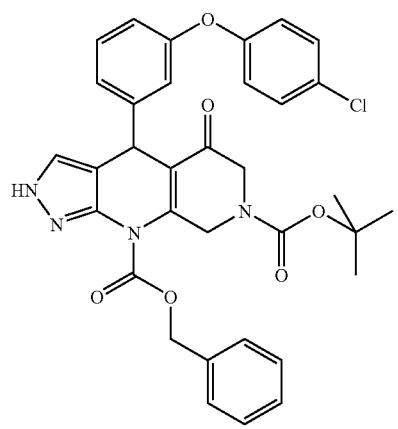

47

45

-continued

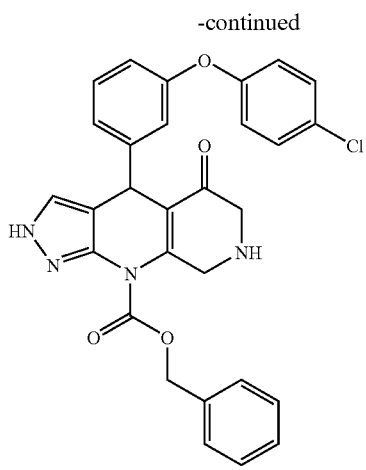

48

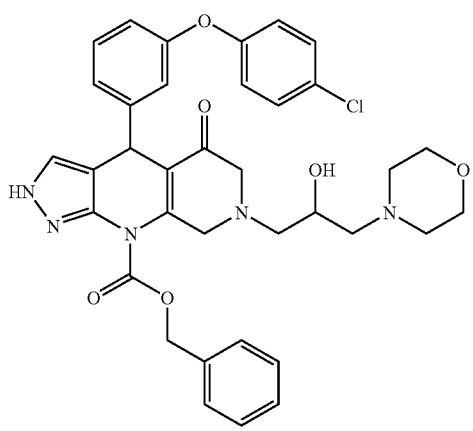

49

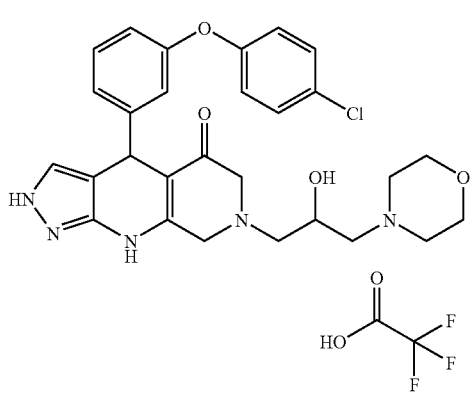

50

Compound 50 is prepared using the same procedure as example 45 using 3-(4-chlorophenoxy)-benzaldehyde as aldehyde. To a mixture of 1.07 g of N-Boc-3,5-diketopiperidine (5 mmoles) and 415 mg of 3-aminopyrazole (5 mmoles) in 10 ml of ethanol is added 962 mg of 3-(4-chlorophenoxy) benzaldehyde (5 mmoles). The mixture is heated at reflux temperature for 1 hour and cooled down to room temperature. The solution is concentrated and the crude product is purified on silica gel using DCM/MeOH (95/5) as eluent. 1.33 g of pale yellow solid 46 is isolated (yield=54%). Analytical LC/MS method A: EIMS ([M+H]+): 493; RT: 3.28 min (gradient 30 to 90% acetonitrile in 7 min).

46

1.21 g of the above solid (2.46 mmoles) are dissolved in 20 ml of DCM and 0.184 ml of benzylchloroformate (4.92 mmoles) is added, followed by 1.6 ml of DIEA (9.84 moles) and 20 mg of DMAP (0.16 mmole). The reaction mixture is shaken overnight at room temperature and then poured into 80 ml of a 10% (w/v) solution of $KH_2SO_4$ and extracted twice with 40 ml of ethyl acetate. The combined organic extracts are washed with brine, dried over $MgSO_4$ and concentrated. The crude product is purified on silica gel using a solution of DCM/MeOH 98/2 as eluent. 1.6 g of desired compound 47 is isolated (quantitative yield). Analytical LC/MS method A: EIMS ([M+H]+): 627; RT: 4.52 min (gradient 30 to 90% acetonitrile in 7 min).

Product 47 is treated with 20 ml of a solution of TFA/DCM (50/50) for 1 hour at room temperature. The solution is concentrated under vacuum. The resulting product is purified on silica gel using DCM/MeOH 90/10 as eluent. 0.91 g of expected compound 48 is isolated (yield=64%). Analytical LC/MS method A: EIMS ([M+H]+): 527; Ret. Time: 2.66 min (gradient 30 to 90% acetonitrile in 7 min).

A solution of 53 mg of 48 (0.1 mmole) and 21 mg of 4-oxiranylmethyl-morpholine (0.15 mmole) in 1 ml of ethanol is heated at reflux temperature for 2 hours. After cooling, the mixture is poured into 80 ml of water and extracted twice with 50 ml of DCM. The combined organic extracts are washed with 50 ml of 0.5N HCl, with brine, dried over $MgSO_4$ and concentrated.

The residue 49 is directly hydrogenated under hydrogen atmosphere using 0.01 mmole of palladium on charcoal. The reaction is stirred overnight and then filtered on Celite®. The filtrate is concentrated and the crude product is directly purified using preparative LC/MS method A. 45 mg of desired compound 50 are isolated (yield=85%). Analytical LC/MS method A: [M+H]+): 536, RT: 3.77 min (gradient 5 to 85% acetonitrile in 7 min).

EXAMPLES 51 and 52

4-[5-(1H-Benzimidazol-2-ylsulfanyl)-furan-2-yl]-9-(2-hydroxy-3-morpholin-4-yl-propyl)-2,4,6,7,8,9-hexahydro-pyrazolo[3,4-b]-1,7-naphthyridin-5-one; compound with trifluoro-acetic acid (ex 52)

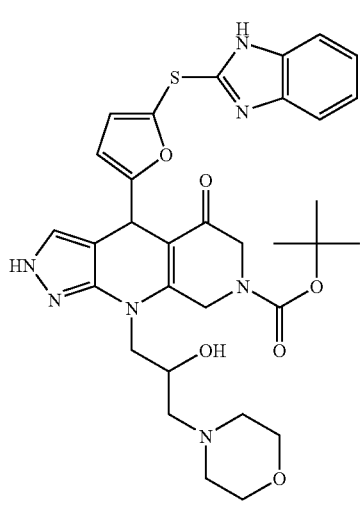

51

EXAMPLE 53

4-[3-(4-Chloro-phenoxy)-phenyl]-7-(3,5-dimethyl-isoxazole-4-carbonyl)-2,4,6,7,8,9-hexahydro-pyrazolo[3,4-b]-1,7-naphthyridin-5-one; compound with trifluoro-acetic acid

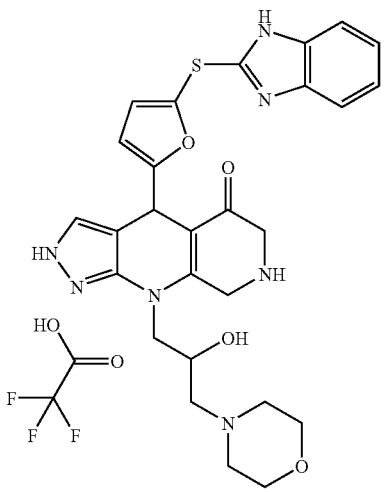

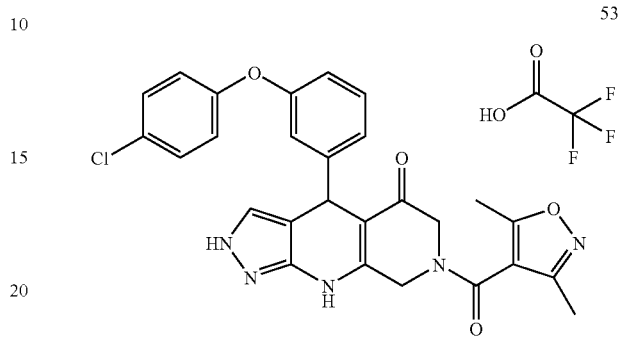

To a solution of 50 mg of compound 44 (0.1 mmole) in 1 ml of EtOH and 1 ml of DMF is added 21 mg of 4-oxiranylmethyl-morpholine (0.15 mmole). The solution is heated at 150° C. under microwave irradiation for 20 minutes. The solution is concentrated and the residue is purified using preparative LC/MS method A. Compound 51 is then treated with 2 ml of a TFA/DCM (50/50) solution for 1 hour at room temperature. The final product is purified by preparative LC/MS (method A). 19 mg of compound 52 are isolated (yield=29%). Analytical LC/MS method A: ([M+H]+): 548, RT: 2.58 min (gradient 5 to 85% acetonitrile in 7 min).

To a solution of 26.3 mg (0.05 mmole) of compound 48 in 0.5 ml of DCM are successively added 12 mg of 3,5-dimethylisoxazole-4-carbonyl chloride (0.75 mmole), 16 μl of DIEA (0.1 mmole) and 5 mg of DMAP (0.04 mmole). The reaction mixture is stirred overnight and then poured into 20 ml of water and extracted twice with 10 ml of DCM. The combined organic extracts are washed with brine, dried over MgSO$_4$ and concentrated. The resulting residue is dissolved in a mixture of 1 ml of methanol and 0.1 ml of acetic acid. The compound is hydrogenated using Pd/C under hydrogen atmosphere. After 20 hour hydrogenation the mixture is filtered on Celite® and the filtrate is concentrated under vacuum. The crude product is purified by preparative LC/MS (method A) resulting in 2.3 mg of product 53. (yield=7.4%). Analytical method A [M+H]+): 516. RT: 4.45 min (gradient 5 to 85% acetonitrile in 7 min).

The following compounds have been prepared the same way:

TABLE 3

| Example number | Structure | Compound name | MW of expected compound | EIMS ([M + H]+) | LC/MS RT (min) |
|---|---|---|---|---|---|
| 54 | 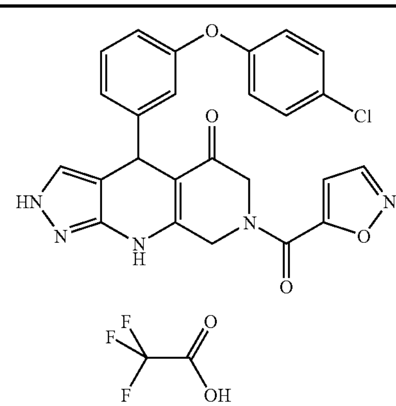 | 4-[3-(4-Chloro-phenoxy)-phenyl]-7-(isoxazole-5-carbonyl)-2,4,6,7,8,9-hexahydro-pyrazolo[3,4-b]-1,7-naphthyridin-5-one; compound with trifluoro-acetic acid | 487.90 | 488 | 4.34 |

TABLE 3-continued

| Example number | Structure | Compound name | MW of expected compound | EIMS ([M + H]+) | LC/MS RT (min) |
|---|---|---|---|---|---|
| 55 | 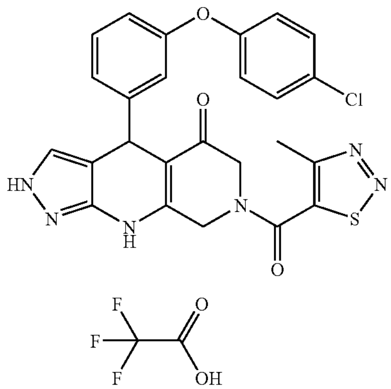 | 4-[3-(4-Chloro-phenoxy)-phenyl]-7-(4-methyl-[1,2,3]thia-diazole-5-carbonyl)-2,4,6,7,8,9-hexahydro-pyrazolo[3,4-b]-1,7-naphthyridin-5-one; compound with trifluoro-acetic acid | 519 | 520 | 4.5 |
| 56 | 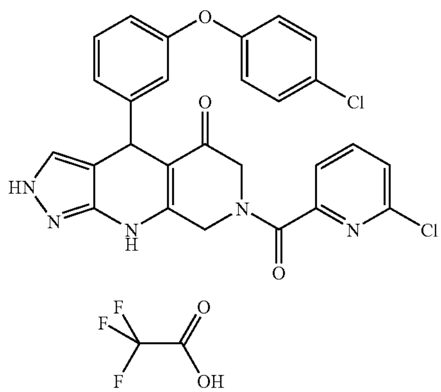 | 4-[3-(4-Chloro-phenoxy)-phenyl]-7-(6-chloro-pyridine-2-carbonyl)-2,4,6,7,8,9-hexahydro-pyrazolo[3,4-b]-1,7-naphthyridin-5-one; compound with trifluoro-acetic acid | 532 | 533 | 4.66 |

Analytical LC/MS conditions: method A, gradient 5 to 85% acetonitrile in 7 min

EXAMPLE 57

7-Acetyl-4-[3-(4-chloro-phenoxy)-phenyl]-2,4,6,7,8,9-hexahydro-pyrazolo[3,4-b]-1,7-naphthyridin-5-one; compound with trifluoro-acetic acid

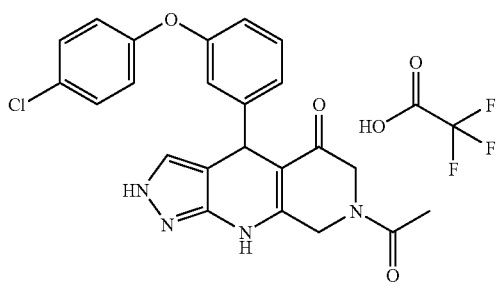

57

To a solution of 25 mg (0.048 mmole) of compound 48 in 1 ml of DCM are successively added 6 µl of acetic anhydride (0.06 mmole) and 16 µl of DIEA (0.1 mmole). The solution is stirred overnight and poured into 20 ml of water. The mixture is extracted twice with 15 ml of DCM. The combined organic extracts are washed with a 10% solution of potassium dihydrogenosulfate, water, dried over MgSO$_4$ and concentrated. The crude product is directly hydrogenated under hydrogen atmosphere using Pd/C as catalyst. The reaction mixture is stirred overnight and then filtered on Celite®. The filtrate is concentrated under vacuum and the resulting residue is purified by preparative LC/MS (method A). 1.1 mg of desired product 57 is isolated (yeild=4%). Analytical LC/MS method A: [M+H]+): 435. RT: 3.71 min (gradient 5 to 85% acetonitrile in 7 min).

EXAMPLE 58

9-Acetyl-4-[3-(4-chloro-phenoxy)-phenyl]-2,4,6,7,8,9-hexahydro-pyrazolo[3,4-b]-1,7-naphthyridin-5-one; compound with trifluoro-acetic acid

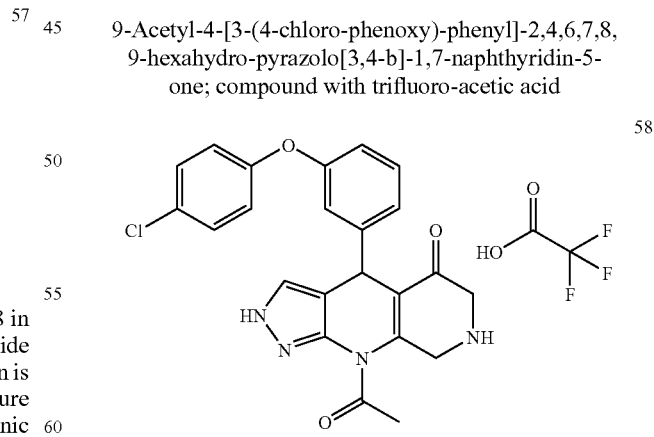

58

To a solution of 25 mg (0.048 mmole) of compound 46 in 0.5 ml of DCM are successively added 11 µl of acetic anhydride (0.11 mmole) and 33 µl of DIEA (0.2 mmole). The solution is stirred at room temperature for 2 hours and poured into 20 ml of water. The mixture is extracted twice with 15 ml of DCM. The combined organic extracts are washed with a 10% solution of potassium dihydrogenosulfate and water, dried over MgSO₄ and concentrated. The crude product is directly treated with 1 ml of TFA/DCM (50/50) solution at room temperature for 1 hour. The mixture is concentrated under vacuum and the resulting residue is purified by preparative LC/MS (method A). 23 mg of desired product 58 are isolated (yield=52%). Analytical LC/MS method A: [M+H]+): 435. RT: 4.33 min (gradient 5 to 85% acetonitrile in 7 min).

EXAMPLE 59

4-[5-(1H-Benzimidazol-2-ylsulfanyl)-furan-2-yl]-9-methyl-2,4,6,7,8,9-hexahydro-pyrazolo[3,4-b]quinolin-5-one; compound with trifluoro-acetic acid

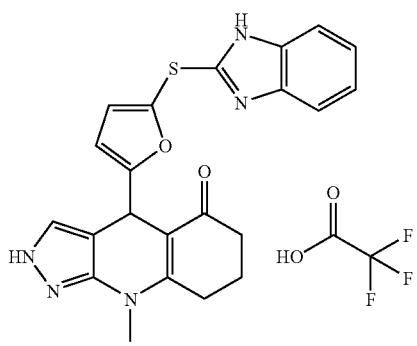

To a solution of 30 mg (0.075 mmole) of compound 3 and 14 µl of methyl iodide (0.225 mmole) in 1 ml of DMF is added 31 mg of potassium carbonate (0.225 mmole). The solution is stirred for 20 hours at room temperature and poured into 20 ml of water. The mixture is extracted twice with 15 ml of DCM. The combined organic extracts are washed with brine, dried over MgSO₄ and concentrated. The crude product is purified by preparative LC/MS (method A). 2.2 mg of desired product 59 are isolated (yield=6%). Analytical LC/MS method A: [M+H]+): 418, RT: 2.54 min (gradient 5 to 85% acetonitrile in 7 min).

EXAMPLE 60

3-(5-Oxo-2,4,6,7,8,9-hexahydro-pyrazolo[3,4b]-1,7-naphthyridin-4-yl)-N-(4-trifluoromethoxy-benzyl)-benzamide; compound with trifluoro-acetic acid

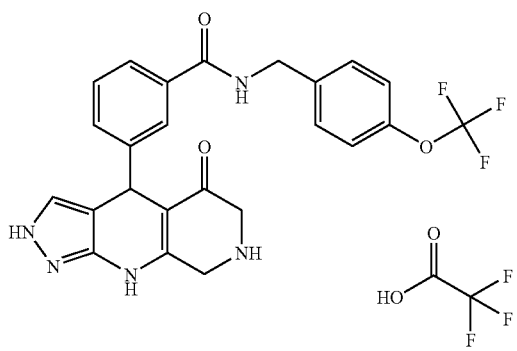

Preparation of the aldehyde: to a solution of 300 mg of 3-carboxybenzaldehyde (2 mmoles) and 382 mg of 4-(trifluoromethoxy)benzylamine (2 mmoles) in 5 ml of DCM is successively added 540 mg of 1-hydroxybenzotriazole (HOBt) (4 mmoles) and 0.63 mg of diisopropylcarbodiimide (DIC) (4 mmoles). The reaction mixture is stirred overnight at room temperature and then poured into 20 ml of 10% KH₂SO₄ solution. The mixture is extracted twice with 15 ml of ethyl acetate. The combined organic extracts are washed with 20 ml of water and 20 ml of brine, dried over MgSO₄ and concentrated giving 670 mg of 3-formyl-N-(4-trifluoromethoxy-benzyl)-benzamide (yield=85%). Analytical LC/MS method A: ([M+H]+): 324, RT: 5.24 min (gradient 5 to 85% acetonitrile in 7 min). Compound 60 is prepared as described for example 2 starting with 21.3 mg of of N-Boc-3,5-diketopiperidine (0.1 mmole), 8.3 mg 3-aminopyrazole (0.1 mmole) and 32.3 mg of 3-formyl-N-(4-trifluoromethoxy-benzyl)-benzamide (0.1 mmole) in a mixture of 0.5 ml of ethanol and 0.5 ml of DMF, resulting in 22.5 mg of product 60 after purification by preparative LC/MS. (method A, yield=38%). Analytical LC/MS method A: ([M+H]+): 484, RT: 2.51 min (gradient 2 to 80% acetonitrile in 7 min).

EXAMPLE 61

3-(5-Oxo-2,4,6,7,8,9-hexahydro-pyrazolo[3,4b]-1,7-naphthyridin-4-yl)-N-(3-trifluoromethoxy-benzyl)-benzamide; compound with trifluoro-acetic acid

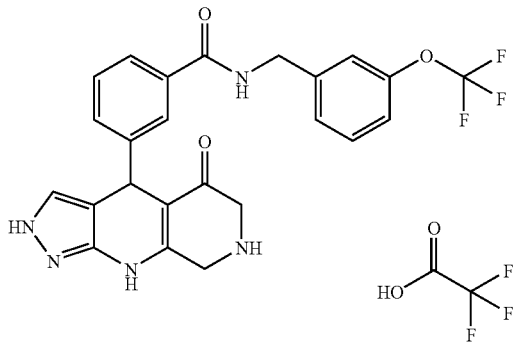

Compound 61 was prepared using the same procedure as described for 60 starting with 3-(trifluoromethoxy)benzylamine. 25.5 mg of desired compound were isolated after preparative LC/MS (method A, yield=43%). Analytical LC/MS method A: [M+H]+): 484, RT: 2.47 min (gradient 2 to 80% acetonitrile in 7 min).

EXAMPLE 62

4-(5-Oxo-2,4,6,7,8,9-hexahydro-pyrazolo[3,4b]-1,7-naphthyridin-4-yl)-N-(3-trifluoromethoxy-phenyl)-benzamide; compound with trifluoro-acetic acid

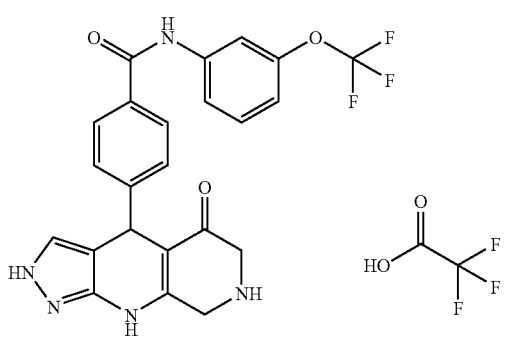

Preparation of the aldehyde: to a solution of 300 mg of 4-carboxybenzaldehyde (2 mmoles) and 382 mg of 3-(trifluoromethoxy)aniline (2 mmoles) in 5 ml of ethyl acetate is added 830 mg of dicyclohexycarbodiimide (DCC) (4 mmoles). The reaction mixture is heated at 60° C. overnight and then poured into 60 ml of 1 N HCl solution. The mixture is extracted twice with 30 ml of ethyl acetate. The combined organic extracts are washed with 50 ml of water, 50 ml of a saturated solution of sodium bicarbonate and brine, dried over MgSO$_4$ and concentrated. The crude product is purified on silica gel giving 233 mg of 4-Formyl-N-(3-trifluoromethoxy-phenyl)-benzamide (yield=38%). Analytical LC/MS method A: ([M+H]+): 310, RT: 5.60 min (gradient 5 to 85% acetonitrile in 7 min).

Starting with 30.9 mg of the above aldehyde (0.1 mmole) and using the same procedure as example 2, 22.3 mg of product 62 were obtained after preparative LC/MS (method A, yield=43%). Analytical LC/MS method A: ([M+H]+): 470, RT: 2.61 min (gradient 2 to 80% acetonitrile in 7 min).

The following examples were obtained using the same procedure:

TABLE 4

| Example number | Structure | Compound name | MW of expected compound | EIMS ([M + H]$^+$) | LC/MS RT (min) |
|---|---|---|---|---|---|
| 63 | 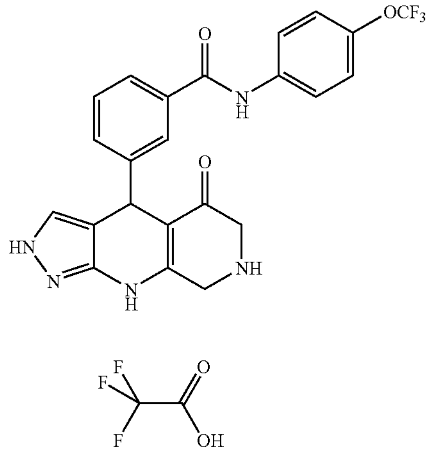 | 3-(5-Oxo-2,4,6,7,8,9-hexahydro-pyrazolo[3,4b]-1,7-naphthyridin-4-yl)-N-(4-trifluoromethoxy-phenyl)-benzamide; compound with trifluoro-acetic acid | 469.43 | 470 | 2.57 |
| 64 | 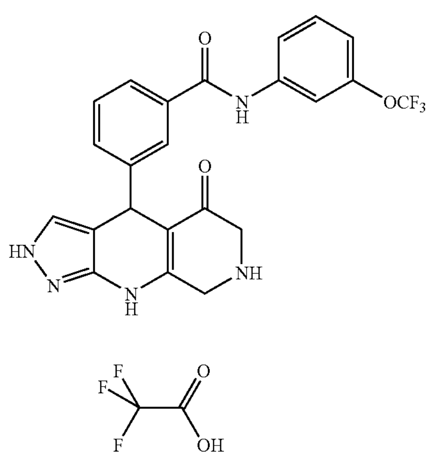 | 3-(5-Oxo-2,4,6,7,8,9-hexahydro-pyrazolo[3,4b]-1,7-naphthyridin-4-yl)-N-(3-trifluoromethoxy-phenyl)-benzamide; compound with trifluoro-acetic acid | 469.43 | 470 | 2.58 |

Analytical LC/MS conditions: method A, gradient 2 to 80% acetonitrile in 7 min

EXAMPLE 65

4-Chloro-N-[3-(5-Oxo-2,4,6,7,8,9-hexahydro-pyrazolo[3,4b]-1,7-naphthyridin-4-yl)-phenyl]-benzamide; compound with trifluoro-acetic acid

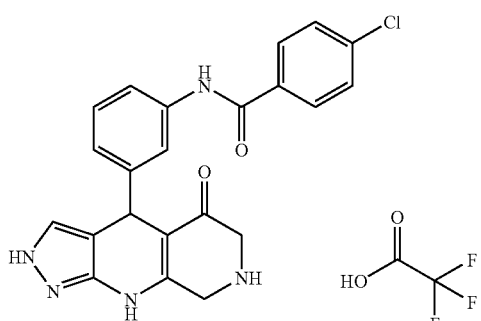

Preparation of the aldehyde: to a solution of 242 mg of 3-aminobenzaldehyde (2 mmoles) and 250 µl of 4-chlorobenzoyl chloride (2 mmoles) in 5 ml of DMF is added 700 µl of DIEA (4 mmoles). The reaction is irradiated in under microwaves at 110° C. for 10 minutes. The precipitate formed is filtrated and washed with methanol. 670 mg of 4-Chloro-N-(3-formyl-phenyl)-benzamide are isolated as a white solid (yield=85%). Analytical LC/MS method A: ([M+H]+): 260

Starting with 26 mg of the above aldehyde (0.1 mmole) and using the same procedure as for example 2, 25 mg of product 65 were obtained after preparative LC/MS (method A, yield=53%). Analytical LC/MS method A: ([M+H]+): 420, RT: 2.14 min (gradient 2 to 80% acetonitrile in 7 min).

EXAMPLE 66

4-Chloro-N-[5-(5-Oxo-2,4,6,7,8,9-hexahydro-pyrazolo[3,4b]-1,7-naphthyridin-4-yl)-thiazol-2-yl]-benzamide; compound with trifluoro-acetic acid

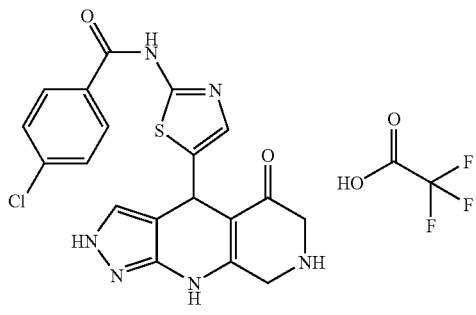

Compound 66 was prepared using the same procedure as described for 65. 266 mg of 4-chloro-N-(5-formyl-thiazol-2-yl)-benzamide were prepared from 256 mg of 2-amino-thiazole-5-carbaldehyde (2 mmoles) and 250 µl of 4-chlorobenzoyl chloride (2 mmoles) (yield=26%). Analytical LC/MS method A: ([M+H]+): 282, RT: 6.10 min (gradient 2 to 80% acetonitrile in 7 min). Starting from 27 mg of the above aldehyde (0.1 mmole), 15.2 mg of desired compound 66 were isolated after purification by preparative LC/MS (method A, yield=28%). Analytical LC/MS method A: ([M+H]+): 427, RT: 2.53 min (gradient 2 to 80% acetonitrile in 7 min).

EXAMPLE 67

1-(4-Chloro-phenyl)-3-[3-(5-Oxo-2,4,6,7,8,9-hexahydro-pyrazolo[3,4b]-1,7-naphthyridin-4-yl)-phenyl]-urea; compound with trifluoro-acetic acid

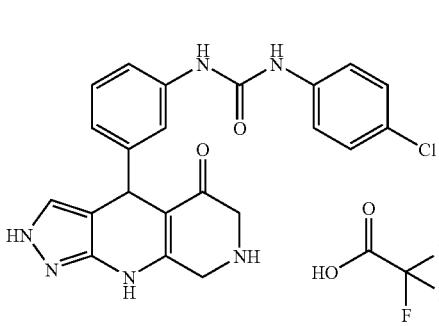

Preparation of the aldehyde: a mixture of 360 mg of 3-aminobenzaldehyde (0.3 mmoles) and 460 mg of 4-chloro-phenylisocyanate (0.3 mmoles) in 3 ml of DMF is heated under microwave irradiation at 110° C. for 10 minutes. The precipitate formed is filtered giving the desired 1-(4-Chloro-phenyl)-3-(3-formyl-phenyl)-urea. Analytical LC/MS method A: ([M+H]+): 351, RT: 5.30 min (gradient 5 to 85% acetonitrile in 7 min).

Starting with 27 mg of the above aldehyde (0.1 mmole) and using the same procedure as in example 2, 23 mg of product 67 were obtained after preparative LC/MS (method A, yield=42%). Analytical LC/MS method A: ([M+H]+): 435, RT: 2.26 min (gradient 2 to 80% acetonitrile in 7 min).

EXAMPLE 68

4-(5-Oxo-2,4,6,7,8,9-hexahydro-pyrazolo[3,4b]-1,7-naphthyridin-4-yl)-N-(4-trifluoromethoxy-phenyl)-benzenesulfonamide; compound with trifluoro-acetic acid

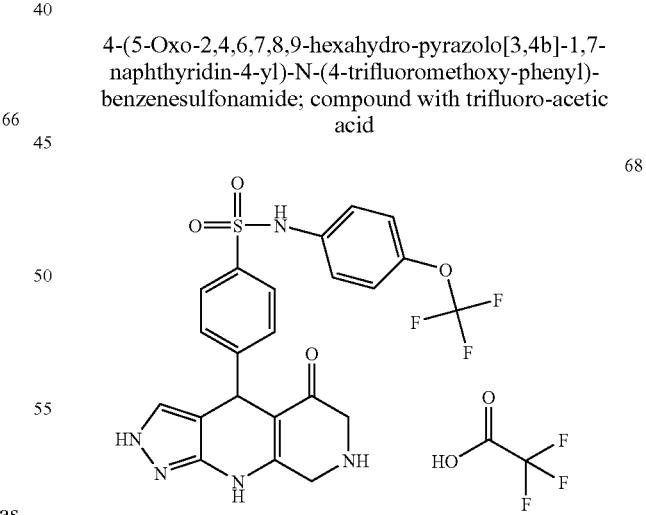

Preparation of the aldehyde: to a mixture of 610 mg of 4-chlorosulfonylbenzaldehyde (3 mmoles) and 460 mg of 4-trifluoromethoxyaniline (3 mmoles) in 2 ml of dichloroethane is added 2 ml of pyridine (25 mmoles). The reaction mixture is stirred at room temperature for 5 hours and then poured into 100 ml of 10% HCl solution. The mixture is extracted twice with 30 ml of DCM. The combined organic extracts are washed with 30 ml of water, 30 ml of a saturated solution of sodium bicarbonate and brine, and the solution is dried over MgSO₄ and concentrated. The crude product is purified on silica gel using DCM/AcOEt 90/10 as eluent. 0.48 g of 4-formyl-N-(4-trifluoromethoxy-phenyl)-benzene-sulfonamide is isolated as a white solid (yield=47%). Analytical LC/MS method A:([M+H]+): 346, RT: 5.53 min (gradient 5 to 85% acetonitrile in 7 min).

Starting with 34.5 mg of the above aldehyde (0.1 mmole) and using the same procedure as in example 2, 19 mg of product 68 were obtained after preparative LC/MS (method A, yield=31%). Analytical LC/MS method A: ([M+H]+): 506, RT: 2.56 min (gradient 2 to 80% acetonitrile in 7 min).

EXAMPLE 69

N-(4-Chloro-phenyl)-4-(5-Oxo-2,4,6,7,8,9-hexahydro-pyrazolo[3,4b]-1,7-naphthyridin-4-yl)-benzene-sulfonamide; compound with trifluoro-acetic acid 69

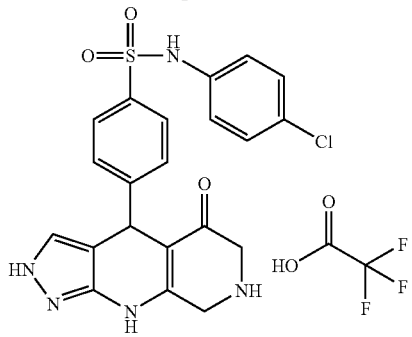

Product 69 was prepared using the same procedure as described for example 68. 450 mg of N-(4-Chloro-phenyl)-4-formyl-benzenesulfonamide were prepared from 256 mg of 4-chlorosulfonylbenzaldehyde (3 mmoles) and 250 µl of 4-chloroaniline (3 mmoles) (yield=51%). Analytical LC/MS method A: ([M+H]+): 296, RT: 5.20 min (gradient 5 to 85% acetonitrile in 7 min).

Starting from 29.6 mg of the above aldehyde (0.1 mmole), and using the same procedure as in example 2 18.8 mg of desired compound 69 were isolated after purification by preparative LC/MS (method A, yield=33%). Analytical LC/MS method A: ([M+H]+): 456, RT: 2.28 min (gradient 2 to 80% acetonitrile in 7 min).

EXAMPLE 70

4-[5-(5-Methyl-1H-benzimidazol-2-ylsulfanyl)-furan-2-yl]-2,4,6,7,8,9-hexahydro-pyrazolo[3,4-b]quinolin-5-one; compound with trifluoro-acetic acid compound with trifluoro-acetic acid 70

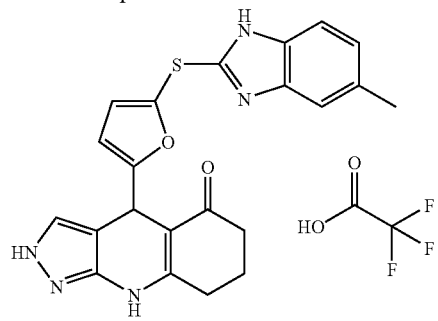

Preparation of the aldehyde: to a solution of 0.82 g of 2-mercapto-5-methyl benzimidazole (5 mmoles) in 10 ml of dry THF is added 200 mg of sodium hydride suspension (60% suspension in mineral oil) (5 mmoles). The reaction mixture is heated at reflux temperature for ½ hour. The mixture is then cooled to room temperature and 0.71 g of 5-nitrofuraldehyde (5 mmoles) in 5 ml of THF is added dropwise. The reaction mixture is stirred for ½ hour and then poured into 200 ml of water. The mixture is extracted twice with 75 ml of EtOAc. The combined organic extracts are washed with brine, dried over MgSO₄ and concentrated. The crude product is purified on silica gel using DCM/MeOH 97/3 as eluent. 1.07 g of 5-(5-Methyl-1H-benzimidazol-2-ylsulfanyl)-furan-2-carbaldehyde is isolated as a black glassy solid (yield=83%). Analytical LC/MS method A: ([M+H]+): 259, RT: 3.64 min (gradient 0 to 50% acetonitrile in 7 min).

Starting with 51.7 mg of the above aldehyde (0.2 mmole) and using the same procedure as in example 3, 48.5 mg of product 70 were obtained after preparative LC/MS (method A, yield=46%). Analytical LC/MS method A: ([M+H]+): 418, RT: 2.48 min (gradient 2 to 80% acetonitrile in 7 min).

Starting from the above aldehyde, the following examples 71 and 72 were obtained and using the procedures described in examples 2 and 4 respectively

TABLE 5

| Examples | Structure | MW of expected compound | EIMS ([M + H]+) | LC/MS RT (min) |
| --- | --- | --- | --- | --- |
| 71 | 4-[5-(5-Methyl-1H-benzimidazol-2-ylsulfanyl)-furan-2-yl]-2,4,6,7,8,9-hexahydro-pyrazolo[3,4-b]-1,7-naphthyridin-5-one; compound with trifluoro-acetic acid | 418.48 | 419 | 2.48 |

TABLE 5-continued

| Examples | Structure | MW of expected compound | EIMS ([M + H]$^+$) | LC/MS RT (min) |
|---|---|---|---|---|
| 72 | 7,7-Dimethyl-4-[5-(5-methyl-1H-benzimidazol-2-ylsulfanyl)-furan-2-yl]-2,4,6,7,8,9-hexahydro-pyrazolo[3,4-b]quinolin-5-one | 445.55 | 446 | 3.39 |

Analytical LC/MS conditions: method A, gradient 2 to 80% acetonitrile in 7 min

EXAMPLE 73

4-[5-(5-Chloro-benzothiazol-2-ylsulfanyl)-furan-2-yl]-2,4,6,7,8,9-hexahydro-pyrazolo[3,4-b]quinolin-5-one; compound with trifluoro-acetic acid

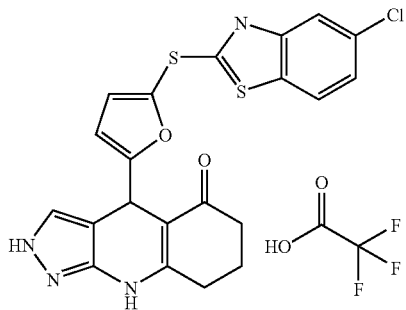

5-(5-Chloro-benzothiazol-2-ylsulfanyl)-furan-2-carbaldehyde (304 mg) was obtained as yellow solid, using the same procedure as described in example 70, starting from 402 mg of 5-chloro-2-mercaptobenzothiazole (2 mmoles) and 282 mg of 5-nitro-2-furaldehyde (2 mmoles) and 80 mg of NaH (Yield=52%)). Analytical LC/MS method A: ([M+H]+): 296, RT: 3.47 min (gradient 30 to 90% acetonitrile in 7 min).

Starting with 50 mg of the above aldehyde (0.17 mmole) and using the same procedure as example 3, 2.6 mg of product 73 were obtained after preparative LC/MS (yield=3%). Analytical LC/MS method A: ([M+H]+): 455, RT: 3.97 min (gradient 2 to 80% acetonitrile in 7 min).

Starting from the above aldehyde, the following examples 74 and 75 were obtained using the procedures described in examples 2 and 4 respectively:

TABLE 6

| Examples | Structure | MW of expected compound | EIMS ([M + H]$^+$) | LC/MS RT (min) |
|---|---|---|---|---|
| 74 | 4-[5-(5-Chloro-benzothiazol-2-ylsulfanyl)-furan-2-yl]-2,4,6,7,8,9-hexahydro-pyrazolo[3,4-b]-1,7-naphthyridin-5-one; compound with trifluoro-acetic acid | 455.95 | 456 | 3.81 |

TABLE 6-continued

| Examples | Structure | MW of expected compound | EIMS ([M + H]+) | LC/MS RT (min) |
|---|---|---|---|---|
| 75 | 4-[5-(5-Chloro-benzothiazol-2-ylsulfanyl)-furan-2-yl]-7,7-dimethyl-2,4,6,7,8,9-hexahydro-pyrazolo[3,4-b]quinolin-5-one | 483.01 | 484 | 4.86 |

Analytical LC/MS conditions: gradient 2 to 80% acetonitrile in 7 min

EXAMPLE 76

4-[5-(5-Difluoromethoxy-1H-benzimidazol-2-ylsulfanyl)-furan-2-yl]-2,4,6,7,8,9-hexahydro-pyrazolo[3,4-b]quinolin-5-one; compound with trifluoro-acetic acid

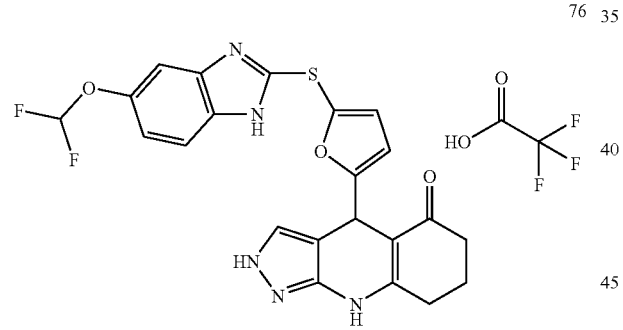

5-(5-Difluoromethoxy-1H-benzimidazol-2-ylsulfanyl)-furan-2-carbaldehyde (417 mg) was obtained using the same procedure as described in example 70, starting from 1.08 g of 5-difluoromethoxy-2-mercaptobenzimidazole (5 mmoles), 0.71 g of 5-nitro-2-furaldehyde (5 mmoles) and 200 mg of NaH (Yield=27%). Analytical LC/MS method A: ([M+H]+): 311, RT: 4.0 min (gradient 0 to 50% acetonitrile in 7 min).

Starting with 63 mg of the above aldehyde (0.2 mmole) and using the same procedure as example 3, 10 mg of product 76 were obtained after preparative LC/MS (method A, yield=9%). Analytial LC/MS method A: ([M+H]+): 470, RT: 3.15 min (gradient 5 to 85% acetonitrile in 7 min).

EXAMPLE 77

4-[5-(6-Methoxy-1H-benzimidazol-2-yloxy)-furan-2-yl]-2,4,6,7,8,9-hexahydro-pyrazolo[3,4-b]quinolin-5-one; compound with trifluoro-acetic acid

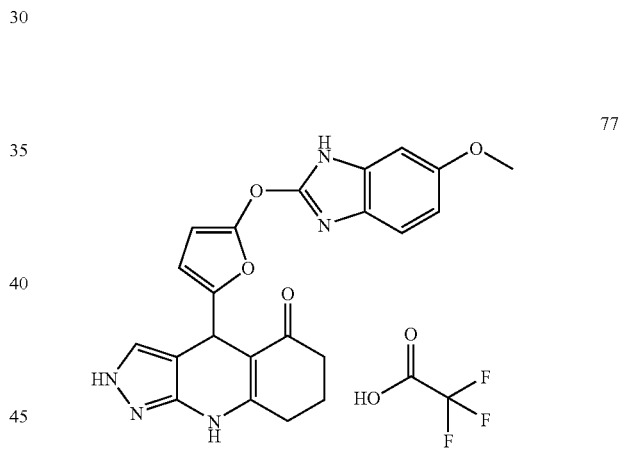

5-(5-Methoxy-1H-benzimidazol-2-yloxy)-furan-2-carbaldehyde (15 mg) was obtained using the same procedure as described in example 70, starting from 0.82 g of 5-methoxy-2-benzimidazolinone (5 mmoles), 0.71 g of 5-nitro-2-furaldehyde (5 mmoles) and 200 mg of NaH (Yield=1.2%). Analytical LC/MS method A: ([M+H]+): 259, RT: 2.53 min (gradient 5 to 85% acetonitrile in 7 min).

Starting with 15 mg of the above aldehyde (0.06 mmole) and using the same procedure as example 3, 2.5 mg of the product 77 were obtained after preparative LC/MS (method A, yield=8%). Analytical LC/MS method A: ([M+H]+): 418, RT: 1.03 min (gradient 10 to 95% acetonitrile in 7 min).

EXAMPLE 78

4-[5-(4-methyl-1H-imidazol-2-ylsulfanyl)-furan-2-yl]-2,4,6,7,8,9-hexahydro-pyrazolo[3,4-b]quinolin-5-one; compound with trifluoro-acetic acid

EXAMPLE 79

4-[5-(5-Methoxy-1H-benzimidazol-2-ylsulfanyl)-furan-2-yl]-2,4,6,7,8,9-hexahydro-pyrazolo[3,4-b]quinolin-5-one; compound with trifluoro-acetic acid

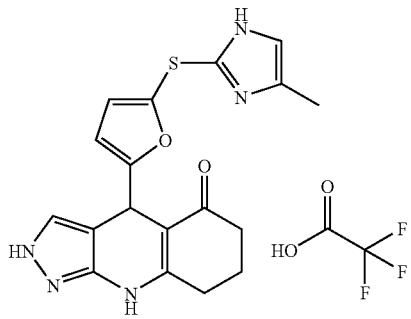

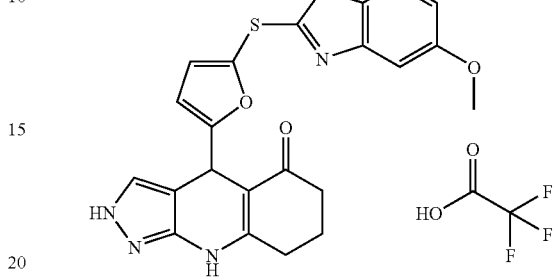

5-(4-Methyl-1H-imidazol-2-ylsulfanyl)-furan-2-carbaldehyde (1.84 g) was obtained using the same procedure as described in example 70, starting from 1 g of 4-methyl-1H-2-mercaptoimidazole (8.75 mmoles), 1.23 g of 5-nitro-2-furaldehyde (8.75 mmoles) and 350 mg of NaH (Yield=100%). Analytical LC/MS method A: ([M+H]+): 209, RT: 0.53 min (gradient 0 to 50% acetonitrile in 7 min).

Starting with 41.7 mg of the above aldehyde (0.2 mmole) and using the same procedure as example 3, 56 mg of product 78 were obtained after preparative LC/MS (method A, yield=58%). Analytical LC/MS method A: ([M+H]+): 368, RT: 2.15 min (gradient 2 to 80% acetonitrile in 7 min).

5-(5-Methoxy-1H-benzimidazol-2-ylsulfanyl)-furan-2-carbaldehyde (1.8 g) was obtained using the same procedure as described in example 70, starting from 1.8 g of 5-methoxy-2-mercaptobenzimidazole (10 mmoles), 1.41 g of 5-nitro-2-furaldehyde (10 mmoles) and 400 mg of NaH (Yield=66%). Analytical LC/MS method A: ([M+H]+): 274, RT: 4.13 min (gradient 0 to 50% acetonitrile in 7 min).

Starting with 54.9 mg of the above aldehyde (0.2 mmole) and using the same procedure as example 3, 45.1 mg of product 79 were obtained after preparative LC/MS (method A, yield=41%). Anlaytical LC/MS method A: ([M+H]+): 434, RT: 2.93 min (gradient 2 to 80% acetonitrile in 7 min).

Starting from the above aldehyde, the following examples 80 and 81 were obtained using the procedures described in examples 2 and 4 respectively:

TABLE 7

| Examples | Structure | MW of expected compound | EIMS ([M + H]+) | LC/MS RT (min) |
| --- | --- | --- | --- | --- |
| 80 | 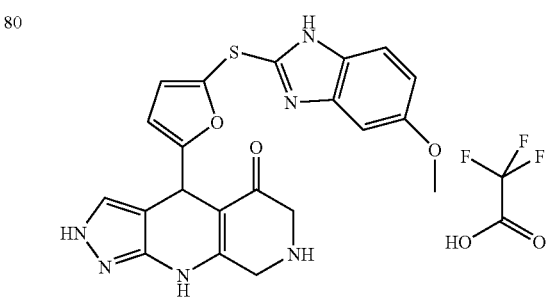<br>4-[5-(5-Methoxy-1H-benzimidazol-2-ylsulfanyl)-furan-2-yl]-2,4,6,7,8,9-hexahydro-pyrazolo[3,4-b]-1,7-naphthyridin-5-one; compound with trifluoro-acetic acid | 434.48 | 435 | 2.34 |

TABLE 7-continued

| Examples | Structure | MW of expected compound | EIMS ([M + H]+) | LC/MS RT (min) |
|---|---|---|---|---|
| 81 | 4-[5-(5-Methoxy-1H-benzimidazol-2-ylsulfanyl)-furan-2-yl]-7,7-dimethyl-2,4,6,7,8,9-hexahydro-pyrazolo[3,4-b]quinolin-5-one | 461.55 | 462 | 3.26 |

Analytical LC/MS conditions: method A, gradient 2 to 80% acetonitrile in 7 min

EXAMPLE 82

4-[5-(1-Methyl-1H-benzimidazol-2-ylsulfanyl)-furan-2-yl]-2,4,6,7,8,9-hexahydro-pyrazolo[3,4-b]quinolin-5-one; compound with trifluoro-acetic acid

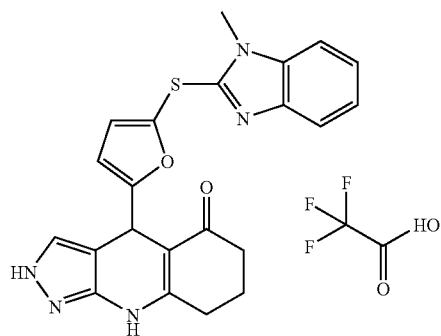

82

5-(1-Methyl-1H-benzimidazol-2-ylsulfanyl)-furan-2-carbaldehyde (1.52 g) was obtained using the same procedure as described in example 70, starting from 0.82 g of 2-mercapto-1-methylbenzimidazole (5 mmoles), 0.71 g of 5-nitro-2-furaldehyde (5 mmoles) and 200 mg of NaH (Yield=85%). Analytical LC/MS method A: ([M+H]+): 259, RT: 1.64 min (gradient 2 to 85% acetonitrile in 7 min).

Starting with 51.7 mg of the above aldehyde (0.2 mmole) and using the same procedure as example 3, 53.3 mg of product 82 were obtained after preparative LC/MS (method A, yield=50%). Analytical LC/MS method A: ([M+H]+): 418, RT: 2.74 min (gradient 2 to 80% acetonitrile in 7 min).

Starting from the above aldehyde, the following examples 83 and 84 were obtained using the procedures described in examples 2 and 4 respectively:

TABLE 8

| Examples | Structure | MW of expected compound | EIMS ([M + H]+) | LC/MS RT (min) |
|---|---|---|---|---|
| 83 | 4-[5-(1-Methyl-1H-benzimidazol-2-ylsulfanyl)-furan-2-yl]-2,4,6,7,8,9-hexahydro-pyrazolo[3,4-b]-1,7-naphthyridin-5-one; compound with trifluoro-acetic acid | 418.12 | 419 | 2.19 |

TABLE 8-continued

| Examples | Structure | MW of expected compound | EIMS ([M + H]⁺) | LC/MS RT (min) |
|---|---|---|---|---|
| 84 | 7,7-Dimethyl-4-[5-(1-methyl-1H-benzimidazol-2-ylsulfanyl)-furan-2-yl]-2,4,6,7,8,9-hexahydro-pyrazolo[3,4-b]quinoline-5-one | 445.16 | 446 | 3.63 |

Analytical LC/MS conditions: method A, gradient 2 to 80% acetonitrile in 7 min

EXAMPLE 85

4-[5-(5,6-Dichloro-1H-benzimidazol-2-ylsulfanyl)-furan-2-yl]-2,4,6,7,8,9-hexahydro-pyrazolo[3,4-b]quinolin-5-one; compound with trifluoro-acetic acid

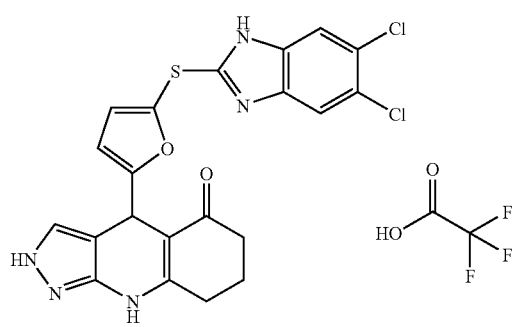

5-(5,6-Dichloro-1H-benzimidazol-2-ylsulfanyl)-furan-2-carbaldehyde (1.24 g) was obtained using the same procedure as described in example 70, starting from 2.2 g of 5,6-dichloro-2-mercaptobenzimidazole (10 mmoles), 1.41 g of 5-nitro-2-furaldehyde (10 mmoles) and 400 mg of NaH (Yield=40%). Analytical LC/MS method A: ([M+H]+): 313, RT: 4.64 min (gradient 0 to 50% acetonitrile in 7 min).

Starting with 62.6 mg of the above aldehyde (0.2 mmole) and using the same procedure as example 3, 26 mg of product 85 were obtained after preparative LC/MS (method A, yield=19%). Analytical LC/MS method A: ([M+H]+): 472, RT 4.13 min (gradient 2 to 80% acetonitrile in 7 min).

The following examples were obtained using the same procedure:

Starting from the above aldehyde, the following examples 86 and 87 were obtained using the procedures described in examples 2 and 4 respectively:

TABLE 9

| Examples | Structure | MW of expected compound | EIMS ([M + H]⁺) | LC/MS RT (min) |
|---|---|---|---|---|
| 86 | 4-[5-(5,6-Dichloro-1H-benzoimidazol-2-ylsulfanyl)-furan-2-yl]-2,4,6,7,8,9-hexahydro-pyrazolo[3,4-b]-1,7-naphthyridin-5-one; compound with trifluoro-acetic acid | 472.03 | 473 | 3.46 |

TABLE 9-continued

| Examples | Structure | MW of expected compound | EIMS ([M + H]+) | LC/MS RT (min) |
|---|---|---|---|---|
| 87 | 4-[5-(5,6-Dichloro-1H-benzoimidazol-2-ylsulfanyl)-furan-2-yl]-7,7-dimethyl-2,4,6,7,8,9-hexahydro-pyrazolo[3,4-b]quinolin-5-one | 499.06 | 500 | 4.49 |

Analytical LC/MS conditions: Method A, gradient 2 to 80% acetonitrile in 7 min

EXAMPLE 88

4-[5-(5-Chloro-benzoxazol-2-ylsulfanyl)-furan-2-yl]-2,4,6,7,8,9-hexahydro-pyrazolo[3,4-b]quinolin-5-one; compound with trifluoro-acetic acid

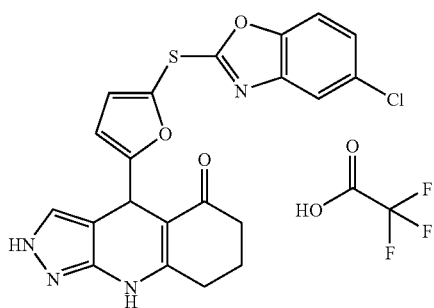

5-(5-Chloro-benzoxazol-2-ylsulfanyl)-furan-2-carbaldehyde (0.58 g) was obtained using the same procedure as described in example 70, starting from 1.03 g of 5-chloro-2-mercaptobenzoxazole (5.5 mmoles), 0.78 g of 5-nitro-2-furaldehyde (5.5 mmoles) and 223 mg of NaH (Yield=37%). Analytical LC/MS method A: ([M+H]+): 280, RT: 4.67 min (gradient 0 to 50% acetonitrile in 7 min).

Starting with 55.9 mg of the above aldehyde (0.2 mmole) and using the same procedure as example 3, 10.2 mg of product 88 were obtained after preparative LC/MS (yield=9%). Analytical LC/MS method A: ([M+H]+): 439, RT: 4.25 min (gradient 2 to 80% acetonitrile in 7 min).

EXAMPLE 89

9-[5-(5-Hydroxy-1H-benzoimidazol-2-ylsulfanyl)-furan-2-yl]-8-oxo-4,5,6,7,8,9-hexahydro-2H-pyrrolo[3,4-b]quinoline-3-carboxylic acid ethyl ester

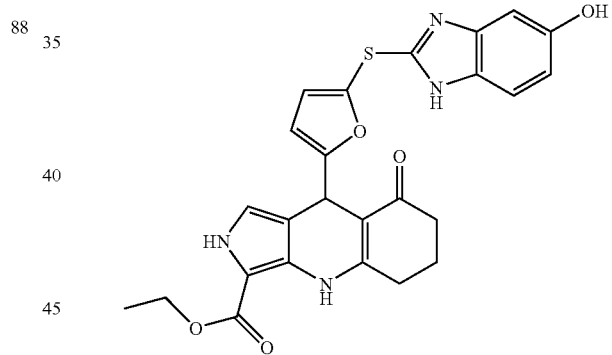

Nitroaniline Intermediate Preparation 4-amino-3-nitrophenol (2 g, 13 mmol) is treated with tert-butyldimethylchlorosilane (2.94 g, 19.5 mmol) in dichloromethane (20 ml) in the presence of triethylamine (2.7 ml, 19.5 mmol) for 16 hours at room temperature. The reaction mixture is washed with water, dried over $MgSO_4$ and concentrated under reduced pressure to yield 1.9 g of 5-(tert-butyl-dimethyl-silanyloxy)-2-nitro-aniline as an orange powder. Yield=55%. Analytical LC/MS (method B): retention time=5.09 min., m/z=269.12 (positive ion mode).

Ortho-Phenylenediamine Intermediate Preparation:

A solution of 5-(tert-butyl-dimethyl-silanyloxy)-2-nitro-aniline (1.9 g, 7.08 mmol) in methanol (40 ml) is introduced in a hydrogenation vessel with 10% palladium on carbon catalyst (0.226 g). The reaction mixture is heated at 80° C. for 3 hours under an hydrogen atmosphere (P=1 bar). The reaction mixture is then filtered on Celite® and concentrated under reduced pressure. The residue is dissolved in 10 ml of ethyl acetate and filtered through a silica gel plug (40 ml) that is washed with 600 ml of ethyl acetate. The organic filtrates are concentrated under vacuum to yield 2.55 g of 4-(tert-butyl-dimethyl-silanyloxy)-ortho-phenylenediamine used without further purification in the following step. Analytical LC/MS (method B): retention time=3.12 min., m/z=239.15 (positive ion mode).

2-Mercaptobenzimidazole Intermediate Preparation:

1,1'-Thiocarbonyldiimidazole (1.87 g, 10.5 mmol) is added by portions to a solution of 4-(tert-butyl-dimethyl-silanyloxy)-ortho-phenylenediamine (2.5 g, 10.5 mmol) in 25 ml of tetrahydrofuran and the mixture is stirred at room temperature for 16 hours. The reaction mixture is then concentrated under reduced pressure, dissolved in 300 ml of ethyl acetate and washed with water (2×100 ml). The organic phase is then dried over MgSO$_4$, filtered and concentrated. The residue is triturated in diisopropylether and pentane and dried under vacuum to yield 2.07 g of 2-mercapto-5-(tert-butyl-dimethyl-silanyloxy)-benzimidazole. Yield=70%. Analytical LC/MS (method B): retention time=4.79 min. m/z=281.36 (positive ion mode).

Aldehyde intermediate preparation: A solution of 2-mercapto-5-(tert-butyl-dimethyl-silanyloxy)-benzimidazole (2.07 g, 7.38 mmol) in tetrahydrofuran (15 ml) is added dropwise to a mixture of sodium hydride (60% dispersion in mineral oil, 0.472 g, 11.8 mmol) and tetrahydrofuran (5 ml) at 0° C. The mixture is stirred at room temperature for 3 hours. A solution of 5-nitro-2-furaldehyde (1.04 g, 7.38 mmol) in tetrahydrofuran (10 ml) is then added dropwise over a 15 minute period and the mixture is stirred for 16 hours at room temperature. Water (10 ml) is then added and the reaction mixture is concentrated under reduced pressure. The residue is dissolved in a minimal volume of ethyl acetate and is filtered through a silica gel plug (20 ml) that is eluted with 500 ml of ethyl acetate. The organic filtrates are concentrated under reduced pressure and are purified on a silicagel column (120 g) eluted with a mixture of cyclohexane and ethyl acetate (7/3, v/v) to yield 1.4 g of 5-[5-(tert-butyl-dimethyl-silanyloxy)-1H-benzimidazol-2-ylsulfanyl]-furan-2-carbaldehyde as a brown oil. Yield=51%. Analytical LC/MS (method B): retention time=4.62 min., m/z=375.05 (positive ion mode).

Tert-Butyldimethylsilyl Protected Intermediate Preparation:

A mixture of 3-amino-2-ethoxycarbonyl-pyrrole (0.412 g, 2.67 mmol), 5-[5-(tert-butyl-dimethyl-silanyloxy)-1H-benzimidazol-2-ylsulfanyl]-furan-2-carbaldehyde (1.0 g, 2.67 mmol) and 1,3-cyclohexanedione (0.299 g, 2.67 mmol) in 10 ml of 1-butanol is heated at reflux temperature for 4 hours. The reaction mixture is then concentrated under reduced pressure. The residue is purified on a silica gel column (50 g) eluted successively with cyclohexane/ethyl acetate (9/1, v/v) and cyclohexane/ethyl acetate (7/3, v/v) to yield 376 mg of 9-{5-[5-(tert-butyl-dimethyl-silanyloxy)-1H-benzimidazol-2-ylsulfanyl]-furan-2-yl}-8-oxo-4,5,6,7,8,9-hexahydro-2H-pyrrolo[3,4-b]quinoline-3-carboxylic acid ethyl ester as an orange solid. Yield=23%. Analytical LC/MS (method B): retention time=4.68 min., m/z=605.11 (positive ion mode).

9-{5-[5-(tert-Butyl-dimethyl-silanyloxy)-1H-benzimidazol-2-ylsulfanyl]-furan-2-yl}-8-oxo-4,5,6,7,8,9-hexahydro-2H-pyrrolo[3,4-b]quinoline-3-carboxylic acid ethyl ester (376 mg, 0.62 mmol) is treated with tetra-N-butylammonium fluoride (162 mg 0.62 mmol) in tetrahydrofuran (5 ml) for 5 hours at room temperature. The reaction mixture is then concentrated under reduced pressure and the residue is purified on a silicagel column (40 g) eluted with a mixture of dichloromethane and methanol (9/1, v/v). The fractions containing the expected product are concentrated under reduced pressure and the residue is washed with acetonitrile (20 ml), pentane (20 ml), diisopropylether (20 ml) and dried under vacuum to yield 154 mg of 9-[5-(5-hydroxy-1H-benzoimidazol-2-ylsulfanyl)-furan-2-yl]-8-oxo-4,5,6,7,8,9-hexahydro-2H-pyrrolo [3,4-b]quinoline-3-carboxylic acid ethyl ester as a light yellow powder. Yield=50%. Analytical LC/MS (method C): m/z=489 (negative ion mode [M−H]$^−$), m/z=491 (positive ion mode [M+H]$^+$).

400 MHz 1H NMR on a BRUKER AVANCE DRX-400 spectrometer, chemical shifts (δ in ppm) in d6 dimethylsufoxyde (DMSO-d6) solvent referenced at 2.50 ppm at 303K temperature:

1.28 (t, J=7.0 Hz, 3H); 1.89 (m, 2H); 2.25 (m, 2H); 2.57 (m, 1H); 2.79 (m, 1H); 4.26 (q, J=7.0 Hz, 2H); 5.13 (s, 1H); 5.94 (d, J=3.5 Hz, 1H); 6.63 (d broad, J=8.5 Hz, 1H); 6.76 (d, J=3.5 Hz, 1H); 6.77 (m broad, 1H); 6.78 (d, J=3.5 Hz, 1H); de 7.10 à 7.39 (m broad, 1H); 8.40 (s, 1H); de 8.92 à 9.28 (m broad, 1H); 11.4 (s broad, 1H); 12.1 (m broad, 1H).

The Following Examples were Obtained Using the Same Procedure:

Starting from the above aldehyde described in example 88, the following examples 90 was obtained using the procedures described in examples 4

TABLE 10

| Examples | Structure | MW of expected compound | EIMS ([M + H]$^+$) | LC/MS RT (min) |
|---|---|---|---|---|
| 90 | 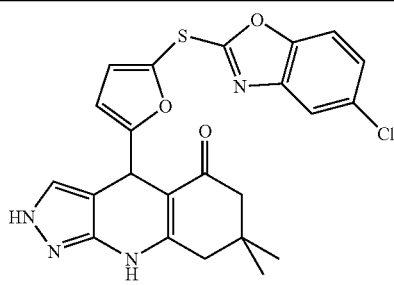<br>4-[5-(5-Chloro-benzoxazol-2-ylsulfanyl)-furan-2-yl]-7,7-dimethyl-2,4,6,7,8,9-hexahydro-pyrazolo[3,4-b]quinoline-5-one | 466.09 | 467 | 4.62 |

Analytical LC/MS conditions: method A, gradient 2 to 80% acetonitrile in 7 min

EXAMPLE 91

7,7-Dimethyl-4-[5-(4-methyl-1H-imidazol-2-ylsulfanyl)-furan-2-yl]-2,4,6,7,8,9-hexahydro-pyrazolo[3,4-b]quinolin-5-one; compound with trifluoro-acetic acid

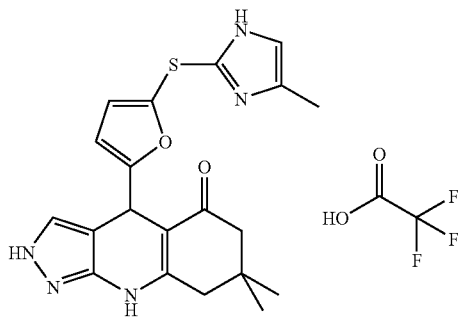

91

Compound 91 was prepared as in example 4 starting with 41.7 mg (0.2 mmole) of 5-(4-Methyl-1H-imidazol-2-ylsulfanyl)-furan-2-carbaldehyde (see preparation in example 78) and 28 mg of dimedone (0.2 mmole). 49.4 mg of desired compound were isolated after preparative LC/MS (method A, yield=49%). Analytical LC/MS method A: ([M+H]+): 396, RT: 2.53 min (gradient 2 to 80% acetonitrile in 7 min).

EXAMPLE 92

4-{5-[5-(4-Chloro-phenyl)-1-methyl-1H-imidazol-2-ylsulfanyl]-furan-2-yl}-2,4,6,7,8,9-hexahydro-pyrazolo[3,4-b]quinolin-5-one

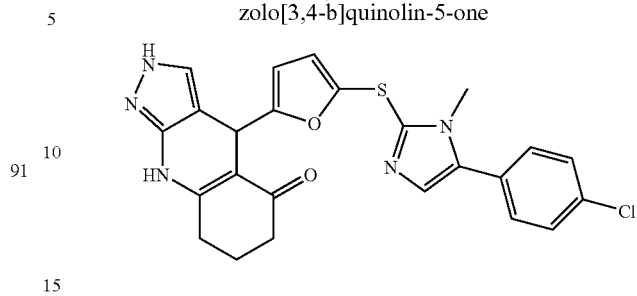

5-[5-(4-Chloro-phenyl)-1-methyl-1H-imidazol-2-ylsulfanyl]-furan-2-carbaldehyde (1.5 g) was obtained using the same procedure as described in example 70, starting from 1 g of 5-(4-chlorophenyl)-1-methyl-1H-imidazol-2-thiol (4.45 mmoles), 0.63 g of 5-nitrofuraldehyde (4.45 mmoles) and 178 mg of sodium hydride (4.45 mmoles). (Yield=100%). Analytical LC/MS method A: ([M+H]+): 319, RT: 3.91 min (gradient 5 to 85% acetonitrile in 7 min).

Starting with 64.2 mg of the above aldehyde (0.2 mmole) and using the same procedure as example 3, 56 mg of product 92 were obtained after chromatography on silica gel using DCM/MeOH 97/3 as eluent (yield=58%). Analytical LC/MS method A: ([M+H]+): 478, RT: 3.48 min (gradient 2 to 80% acetonitrile in 7 min).

Starting from the above aldehyde, the following examples 93 and 94 were obtained using the procedures described in examples 4 and 2 respectively:

TABLE 11

| Examples | Structure | MW of expected compound | EIMS ([M + H]+) | LC/MS RT (min) |
|---|---|---|---|---|
| 93 | 4-{5-[5-(4-Chloro-phenyl)-1-methyl-1H-imidazol-2-ylsulfanyl]-furan-2-yl}-7,7-dimethyl-2,4,6,7,8,9-hexahydro-pyrazolo[3,4-b]quinolin-5-one | 505.13 | 506 | 3.74 |

TABLE 11-continued

| Examples | Structure | MW of expected compound | EIMS ([M + H]+) | LC/MS RT (min) |
|---|---|---|---|---|
| 94 | 4-{5-[5-(4-Chloro-phenyl)-1-methyl-1H-imidazol-2-ylsulfanyl]-furan-2-yl}-2,4,6,7,8,9-hexahydro-pyrazolo[3,4-b]-1,7-naphthyridin-5-one; compound with trifluoro-acetic acid | 478.10 | 479 | 2.87 |

Analytical LC/MS conditions: method A, gradient 2 to 80% acetonitrile in 7 min

EXAMPLE 95

4-[5-(5-Trifluoromethyl-1H-benzimidazol-2-ylsulfanyl)-furan-2-yl]-1,4,6,7,8,9-hexahydro-pyrazolo[3,4-b]quinolin-5-one

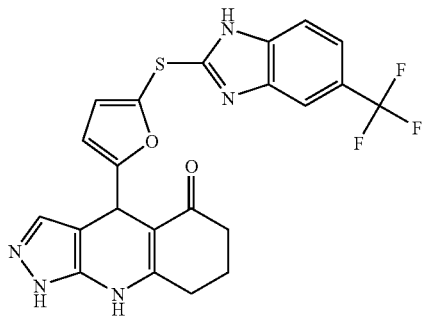

5-(5-Trifluoromethyl-1H-benzimidazol-2-ylsulfanyl)-furan-2-carbaldehyde (1.4 g) was obtained using the same procedure as described in example 70, starting from 1 g of 2-mercapto-5-trifluoromethylbenzimidazole (4.6 mmoles), 0.65 g of 5-nitrofuraldehyde (4.6 mmoles) and 180 mg of sodium hydride (4.6 mmoles). (Yield=99%). Analytical LC/MS method A: ([M+H]+): 313, RT: 4.78 min (gradient 5 to 85% acetonitrile in 7 min).

Starting with 63 mg of the above aldehyde (0.2 mmole) and using the same procedure as example 3, 43 mg of product 95 were obtained after chromatography on silica gel using DCM/MeOH 97/3 as eluent (yield=46%). Analytical LC/MS method A: ([M+H]+): 472, RT: 3.84 min (gradient 2 to 80% acetonitrile in 7 min).

Starting from the above aldehyde, the following examples 96 and 97 were obtained using the procedures described in examples 4 and 2 respectively

TABLE 12

| Examples | Structure | MW of expected compound | EIMS ([M + H]+) | LC/MS RT (min) |
|---|---|---|---|---|
| 96 | 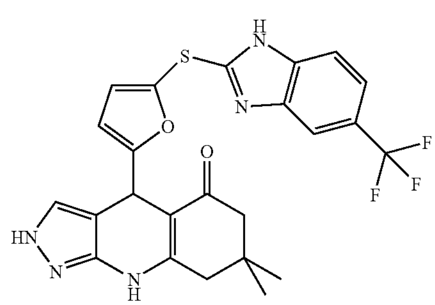 | 499.52 | 500 | 4.22 |

TABLE 12-continued

| Examples | Structure | MW of expected compound | EIMS ([M + H]+) | LC/MS RT (min) |
|---|---|---|---|---|
| 97 | 4-[5-(5-Trifluoromethyl-1H-benzoimidazol-2-ylsulfanyl)-furan-2-yl]-7,7-dimethyl-2,4,6,7,8,9-hexahydro-pyrazolo[3,4-b]quinolin-5-one 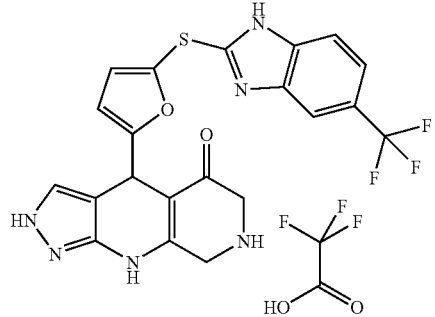 4-[5-(5-Chloro-1H-benzoimidazol-2-ylsulfanyl)-furan-2-yl]-2,4,6,7,8,9-hexahydro-pyrazolo[3,4-b]-1,7-naphthyridin-5-one; compound with trifluoro-acetic acid | 472.09 | 473 | 3.25 |

Analytical LC/MS conditions: method A, gradient 2 to 80% acetonitrile in 7 min

EXAMPLE 98

4-[5-(4,5-Dimethyl-1H-imidazol-2-ylsulfanyl)-furan-2-yl]-2,4,6,7,8,9-hexahydro-pyrazolo[3,4-b]quinolin-5-one

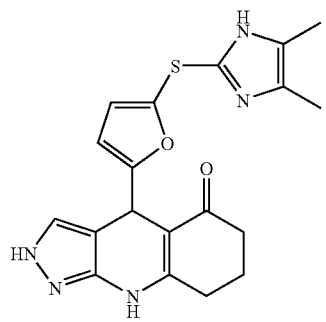

5-(4,5-Dimethyl-1H-imidazol-2-ylsulfanyl)-furan-2-carbaldehyde (2 g) was obtained using the same procedure as described in example 70, starting from 1 g of 4,5-dimethyl-2-mercapto-1H-imidazole (7.96 mmoles), 1.12 g of 5-nitro-furaldehyde (7.96 mmoles) and 320 mg of sodium hydride (7.96 mmoles). (Yield=100%). Analytical LC/MS method A: ([M+H]+): 223, RT: 2.34 min (gradient 5 to 85% acetonitrile in 7 min).

Starting with 44.5 mg of the above aldehyde (0.2 mmole) and using the same procedure as example 3, 36.4 mg of product 98 were obtained after chromatography on silica gel using DCM/MeOH 97/3 as eluent (yield=37%). Analytical LC/MS method A: ([M+H]+): 382, RT: 2.31 min (gradient 2 to 80% acetonitrile in 7 min).

Starting from the above aldehyde, the following examples 99 and 100 were obtained using the procedures described in examples 4 and 2 respectively

TABLE 13

| Examples | Structure | MW of expected compound | EIMS ([M + H]+) | LC/MS RT (min) |
|---|---|---|---|---|
| 99 | 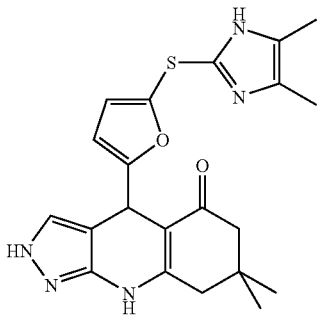 | 409.51 | 410 | 2.69 |

TABLE 13-continued

| Examples | Structure | MW of expected compound | EIMS ([M + H]⁺) | LC/MS RT (min) |
|---|---|---|---|---|
| 100 | 4-[5-(4,5-Dimethyl-1H-imidazol-2-ylsulfanyl)-furan-2-yl]-7,7-dimethyl-2,4,6,7,8,9-hexahydro-pyrazolo[3,4-b]quinolin-5-one<br>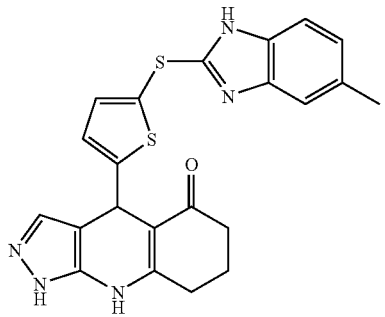<br>4-[5-(4,5-Dimethyl-1H-imidazol-2-ylsulfanyl)-furan-2-yl]-2,4,6,7,8,9-hexahydro-pyrazolo[3,4-b]-1,7-naphthyridin-5-one; compound with trifluoro-acetic acid | 382.45 | 383 | 1.77 |

Analytical LC/MS conditions: method A, gradient 2 to 80% acetonitrile in 7 min

EXAMPLE 101

4-[5-(5-Methyl-1H-benzimidazol-2-ylsulfanyl)-thiophen-2-yl]-1,4,6,7,8,9-hexahydro-pyrazolo[3,4-b]quinolin-5-one Preparation of the aldehyde: a mixture of 0.82 g of 2-mercapto-5-methyl-benzimidazole (5 mmoles), 0.6 ml of 5-bromo-2-thiophenecarboxaldehyde (5 mmoles) and 1.4 g of potassium carbonate in 10 ml of DMF is heated at 110° C. for 2 hours. The mixture is cooled down to room temperature, then poured into 200 ml of water and extracted twice with 50 ml of ethyl acetate. The combined organic extracts are washed with brine, dried over MgSO₄ and concentrated. The crude product is purified on silica gel using DCM/MeOH as eluent to give 0.65 g of 5-(5-methyl-1H-benzimidazol-2-ylsulfanyl)-thiophene-2-carbaldehyde. (Yield=47%). Analytical LC/MS method A: ([M+H]+): 275). RT: 3.42 min (gradient 5 to 85% acetonitrile in 7 min).

Starting with 54.9 mg of the above aldehyde (0.2 mmole) and using the same procedure as example 3, 78.8 mg of product 101 were obtained after chromatography on silica gel using DCM/MeOH 97/3 as eluent (yield=91%). Analytical LC/MS method A: ([M+H]+): 434), RT: 3.07 min (gradient 2 to 80% acetonitrile in 7 min).

The Following Examples were Obtained Using the Same Procedure:

Starting from the above aldehyde, the following examples 102 and 103 were obtained using the procedures described in examples 4 and 2 respectively

TABLE 14

| Examples | Structure | MW of expected compound | EIMS ([M + H]⁺) | LC/MS RT (min) |
|---|---|---|---|---|
| 102 | 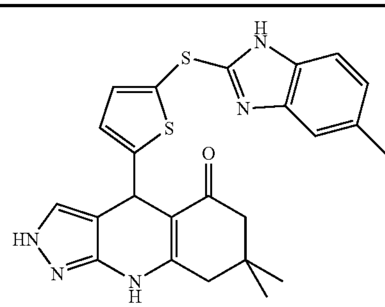 | 461.61 | 462 | 3.44 |

TABLE 14-continued

| Examples | Structure | MW of expected compound | EIMS ([M + H]+) | LC/MS RT (min) |
|---|---|---|---|---|
| 103 | 7,7-Dimethyl-4-[5-(5-methyl-1H-benzoimidazol-2-ylsulfanyl)-thiophen-2-yl]-2,4,6,7,8,9-hexahydro-pyrazolo[3,4-b]quinolin-5-one<br><br>4-[5-(5-Methyl-1H-benzoimidazol-2-ylsulfanyl)-thiophen-2-yl]-2,4,6,7,8,9-hexahydro-pyrazolo[3,4-b]-1,7-naphthyridin-5-one; compound with trifluoro-acetic acid | 434.10 | 435 | 2.5 |

Analytical LC/MS conditions: method A, gradient 2 to 80% acetonitrile in 7 min

EXAMPLE 104

9-[5-(1H-Benzimidazol-2-ylsulfanyl)-furan-2-yl]-8-oxo-4,5,6,7,8,9-hexahydro-2H-pyrrolo[3,4-b]-1,7-naphthyridine-3-carboxylic acid ethyl ester; compound with trifluoro-acetic acid

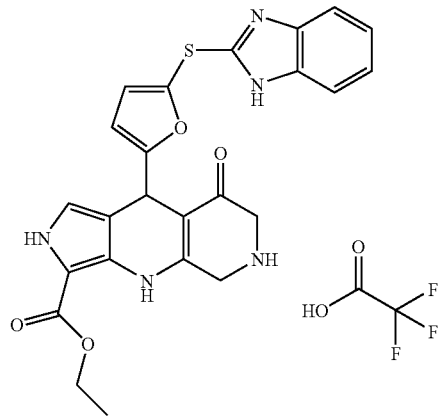

Compound 104 was obtained using the same procedure as example 2, starting from 42 mg of N-Boc-3,5-diketopiperidine (0.2 mmole), 38 mg of 3-amino-2-ethoxycarbonylpyrrole hydrochloride (0.2 mmole), 51 mg of 5-(1H-benzimidazol-2-ylsulfanyl)-furan-2-carbaldehyde (0.2 mmole) and 33 µl of DIEA (0.2 mmole). After preparative LC/MS (method A) 8.5 mg of desired product 104 were isolated (yield=7%). Analytical L/MS method A: ([M+H]+): 476, RT: 2.98 min (gradient 5 to 85% acetonitrile in 7 min).

EXAMPLE 105

9-[5-(1H-Benzimidazol-2-ylsulfanyl)-furan-2-yl]-8-oxo-4,5,6,7,8,9-hexahydro-2H-pyrrolo[3,4-b]quinoline-3-carboxylic acid ethyl ester; compound with trifluoro-acetic acid

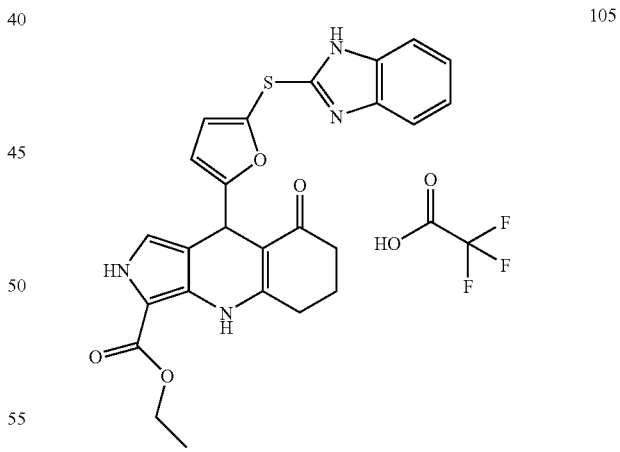

Compound 105 was obtained using the same procedure as example 3, starting from 22.4 mg of 1,3-cyclohexanedione (0.2 mmole), 38 mg of 3-amino-2-ethoxycarbonyl-pyrrole hydrochloride (0.2 mmole), 51 mg of 5-(1H-benzimidazol-2-ylsulfanyl)-furan-2-carbaldehyde (0.2 mmole) and 33 µl of DIEA (0.2 mmole). After preparative LC/MS (method A) 7.7 mg of desired product 105 were isolated (yield=7%). Analytical LC/MS method A: ([M+H]+): 475, RT: 3.94 min (gradient 5 to 85% acetonitrile in 7 min).

Alternative Preparation of Example 105:

Alternatively example 105 can be prepared by reacting 3-amino-2-ethoxycarbonyl-pyrrole (31.5 g, 204 mmol), 5-(1H-benzimidazol-2-ylsulfanyl)-furan-2-carbaldehyde (50 g, 204 mmol) and 1,3-cyclohexanedione (22.95 g 204 mmol) in 2.5 l of 1-butanol at reflux temperature for 3 hours. The reaction mixture is then concentrated under reduced pressure. The residue is resuspended in 1 l of ethanol and heated to reflux temperature for 2 hours and let to cool to room temperature. The formed insoluble material is collected by filtration, washed with ethanol (0.4 l), diisopropyl ether (0.4 l), pentane (0.4 l) and dried under vacuum. The residue is resuspended in 2 l of acetonitrile, heated to reflux temperature for 2 hours and let to cool to room temperature. The insoluble material is collected by filtration, washed with acetonitrile (0.6 l), diisopropyl ether (0.6 l), pentane (0.6 l) and dried under vacuum to yield 41.5 g of 9-[5-(1H-Benzimidazol-2-ylsulfanyl)-furan-2-yl]-8-oxo-4,5,6,7,8,9-hexahydro-2H-pyrrolo[3,4-b]quinoline-3-carboxylic acid ethyl ester in the base form as a light gray powder. Yield=43%. Analytical LC/MS method B: retention time=3.32 min. m/z=475.06 (positive ion mode).

400 MHz 1H NMR on a BRUKER AVANCE DRX-400 spectrometer, chemical shifts (δ in ppm) in d6 dimethylsufoxyde (DMSO-d6) solvent referenced at 2.50 ppm at 303K temperature: 1.28 (t, J=7.0 Hz, 3H); 1.88 (m, 2H); 2.25 (m, 2H); 2.58 (m, 1H); 2.79 (m, 1H); 4.26 (q, J=7.0 Hz, 2H); 5.15 (s, 1H); 5.97 (d, J=3.5 Hz, 1H); 6.79 (d, J=3.5 Hz, 1H); 6.82 (d, J=3.5 Hz, 1H); de 7.12 à 7.17 (m, 2H); 7.47 (m broad, 2H); 8.40 (s, 1H); 11.4 (s, broad, 1H); 12.4 (m broad, 1H).

EXAMPLE 106

9-[5-(1H-Benzimidazol-2-ylsulfanyl)-furan-2-yl]-6,6-dimethyl-8-oxo-4,5,6,7,8,9-hexahydro-2H-pyrrolo[3,4-b]quinoline-3-carboxylic acid ethyl ester

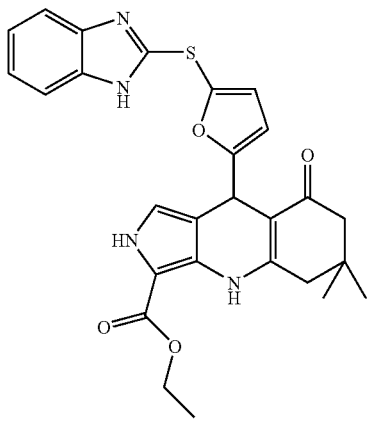

430 mg (1.76 mmol) of 5-(1H-benzimidazol-2-ylsulfanyl)-furan-2-carbaldehyde are combined to 197 mg (1.405 mmol) of dimedone, 335 mg (1.76 mmol) of 3-amino-2-ethoxycarbonylpyrrole hydrochloride, 742 mg (5.741 mmol) of N,N-diisopropylethylamine in 10 ml ethanol. The stirred reaction mixture is refluxed overnight. Upon cooling to room temperature, reaction mixture was half concentrated under reduced pressure and then diluted with water and extracted with ethyl acetate. The organic layer is washed with water and with brine and then dried on magnesium sulfate, filtered and concentrated under reduced pressure giving crude product. The resulting oily residue is dissolved in 10 ml of dichloromethane and purified by chromatography on a prepacked 120 g 15-40 μm silica gel cartridge (eluting solvent: cyclohexane/ethyl acetate from 100/0 to 70/30 v/v; rate: 50 mL/min, in 50 min, from 70/30 to 50/50 v/v in 10 min, and then from 50/50 to 40/60 v/v in 30 min). The fractions containing the desired product are combined and concentrated to dryness under reduced pressure giving 330 mg of expected compound with 47% yield.

Analytical LC/MS method B: [M+H+]=503.3; retention time: 3.61 min; 68% UV.

EXAMPLE 107

10-[5-(1H-Benzoimidazol-2-ylsulfanyl)-furan-2-yl]-9-oxo-2,4,5,6,7,8,9,10-octahydro-2,4-diaza-cyclohepta[f]indene-3-carboxylic acid ethyl ester, compound with trifluoroacetic acid

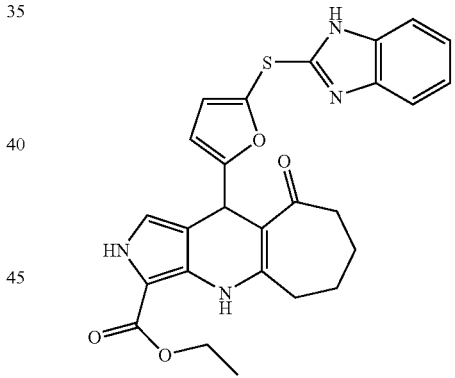

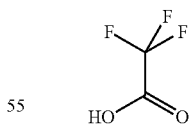

Starting from 51 mg of 5-(1H-benzimidazol-2-ylsulfanyl)-furan-2-carbaldehyde (0.2 mmole), 38 mg of 3-amino-2-ethoxycarbonyl-pyrrole hydrochloride (0.2 mmole) and 28 mg of 1,3-cycloheptane dione (0.2 mmole), product 107 was obtained using the procedure described in example 105. Analytical LC/MS method A: ([M+H]+): 489, RT: 4.69 min (gradient 5 to 85% acetonitrile in 7 min).

EXAMPLE 108

9-[5-(5-Methyl-1H-benzimidazol-2-ylsulfanyl)-furan-2-yl]-8-oxo-4,5,6,7,8,9-hexahydro-2H-pyrrolo[3,4-b]quinoline-3-carboxylic acid ethyl ester

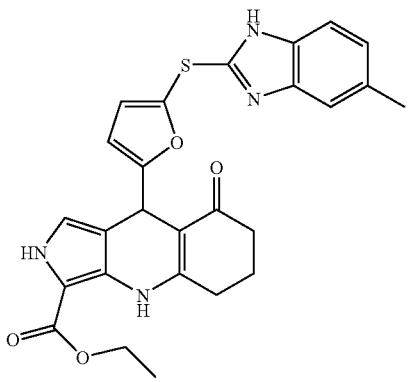

Step 1: 5-(5-Methyl-1H-benzimidazol-2-ylsulfanyl)-furan-2-carbaldehyde 1.16 g of 2-mercapto-5-methylbenzimidazole in 14 mL of tetrahydrofurane (THF) are dropped into a 100 mL three-neck flask, and then 309 mg of sodium hydride is added. The mixture is stirred at reflux temperature for 30 minutes followed by addition of 1 g of 5-nitro furaldehyde in 7 mL of THF. The reaction medium is allowed to cool down to room temperature (ca. 20° C.) and then poured in a mixture of 200 mL of water and 100 mL of ethyl acetate (EtOAc). The organic layer is isolated and the aqueous layer is extracted twice with EtOAc (2×100 mL). The organic layers are combined, dried on magnesium sulfate, and concentrated under reduced pressure. 1.8 g of 5-(5-Methyl-1H-benzimidazol-2-ylsulfanyl)-furan-2-carbaldehyde is collected. Analytical LC/MS method B: RT: 2.98 min; [M+H]$^+$: 259; 80% UV purity

Step 2: 9-[5-(5-Methyl-1H-benzimidazol-2-ylsulfanyl)-furan-2-yl]-8-oxo-4,5,6,7,8,9-hexahydro-2H-pyrrolo[3,4-b]quinoline-3-carboxylic acid ethyl ester (title compound)

774 μmol of 3-amino-2-ethoxycarbonylpyrrole hydrochloride, 774 μmol of 5-(5-Methyl-1H-benzimidazol-2-ylsulfanyl)-furan-2-carbaldehyde (obtained from step 1), 774 μmol of 1,3 cyclohexanedione and 400 μL of N,N-diisopropylethylamine in 3 mL of ethanol are poured into a flask suitable for microwave irradiation (Personal Chemistry model Emrys Optimizer instrument). The flask is locked then irradiation is performed at 100° C. during 700 seconds. After cooling down to 20° C., the reaction mixture is concentrated under reduced pressure. The residue is purified on silica gel (Analogix model Intelliflash 280 instrument, SiO$_2$ 75 g; Eluent EtOAc/cyclohexane; from 10/90 to 80/20. (v/v), rate: 25 mL/min). The fractions containing the expected compound are combined and concentrated under reduced pressure. The remaining oil is solubilized in 0.5 mL of dichloromethane (DCM) then crystallized by addition of small amounts of diisopropyloxide. 60 mg of solid were collected.

400 MHz $^1$H NMR (DMSO-d6), δ (ppm): 1.28 (t, J=7.0 Hz, 3H); 1.89 (m, 2H); 2.25 (m, 2H); 2.38 (s, 3H); 2.57 (m, 1H); 2.79 (m, 1H); 4.26 (q, J=7.0 Hz, 2H); 5.14 (s, 1H); 5.96 (d, J=3.0 Hz, 1H); 6.80 (d large, J=3.0 Hz, 2H); 6.98 (m large, 1H); 7.15-7.45 (m large, 2H); 8.42 (s, 1H); 11.40 (m large, 1H); 12.3 (m large, 1H).

MS: ES, m/z=489=MH$^+$.

EXAMPLE 109

6,6-Dimethyl-9-[5-(5-methyl-1H-benzimidazol-2-ylsulfanyl)-furan-2-yl]-8-oxo-4,5,6,7,8,9-hexahydro-2H-pyrrolo[3,4-b]quinoline-3-carboxylic acid ethyl ester

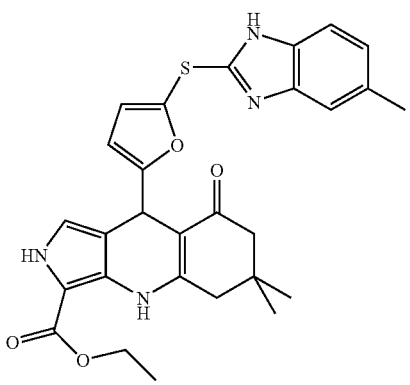

387 μmol of 3-amino-2-ethoxycarbonylpyrrole hydrochloride, 387 μmol of 5-(5-Methyl-1H-benzimidazol-2-ylsulfanyl)-furan-2-carbaldehyde (obtained from example 108, step 1), 387 μmol of dimedone and 202 μL of N,N-diisopropylethylamine in 1.5 mL of ethanol are poured into a flask suitable for microwave irradiation (Personal Chemistry model Emrys Optimizer instrument). The flask is locked then irradiation is performed at 100° C. during 700 seconds. After cooling down to 20° C., the reaction mixture is concentrated under reduced pressure. The residue is purified on silica gel (Analogix model Intelliflash 280 instrument, SiO$_2$ 40 g; Eluent EtOAc/cyclohexane; from 30/70 to 75/25. (v/v), rate: 25 mL/min, during 70 minutes). The fractions containing the expected compound are combined and concentrated under reduced pressure. The remaining oil is solubilized in 0.5 mL of dichloromethane (DCM) then crystallized by addition of small amounts of diisopropyloxide. 62 mg of expected compound are collected as a solid.

300 MHz $^1$H NMR (DMSO-d6), δ (ppm):

The following signals are attributed to one species (abundance 75% over the spectrum): 0.92 (s, 3H); 1.00 (s, 3H); 1.29 (t, J=7.0 Hz, 3H); 2.05 (d, J=16.5 Hz, 1H); 2.18 (d, J=16.5 Hz, 1H); 2.38 (s, 3H); 2.45-2.65 (m hidden in part, 2H); 4.25 (q, J=7.0 Hz, 2H); 5.14 (s, 1H); 5.98 (d, J=3.0 Hz, 1H); 6.77 (d, J=3.0 Hz, 1H); 6.82 (d large, J=3.0 Hz, 1H); 6.98 (dd, J=2.0 et 8.5 Hz, 1H); 7.24 (s large, 1H); 7.34 (d, J=8.5 Hz, 1H); 8.30 (s, 1H); 11.40 (m large, 1H).

MS: ES, m/z=517=MH$^+$.

EXAMPLE 110

9-[5-(5-Methoxy-1H-benzimidazol-2-ylsulfanyl)-furan-2-yl]-8-oxo-4,5,6,7,8,9-hexahydro-2H-pyrrolo[3,4-b]quinoline-3-carboxylic acid ethyl ester

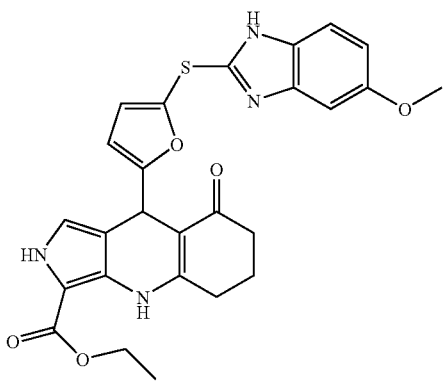

Step 1: 5-(5-Methoxy-1H-benzimidazol-2-ylsulfanyl)-furan-2-carbaldehyde

2-Mercapto-5-methoxybenzimidazole (1.8 g, 10.0 mmol) is suspended into 25 mL of tetrahydrofuran (THF) under argon. Then, 575 mg (12.0 mmol) of sodium hydride are added. The reaction mixture is stirred at room temperature until gas evolution has ceased. A solution of 5-nitro-2-furaldehyde (1.4 g, 10.0 mmol) in 30 mL of THF is then added dropwise and the reaction mixture is stirred at room temperature for 2 h, upon which it is poured on ice and extracted 3 times with 50 mL of ethyl acetate. The organic extracts are combined, washed with brine, dried on magnesium sulfate, filtered and concentrated under reduced pressure. The residue is triturated in diisopropyl ether and the resulting suspension is stirred for 1 h. The solid is filtered, washed twice with diisopropyl ether and dried. 0.75 g of 5-(5-methoxy-1H-benzimidazol-2-ylsulfanyl)-furan-2-carbaldehyde is obtained as a pale yellow powder. The filtrate is concentrated under reduced pressure and the residue is purified by chromatography on a prepacked 90 g 15-40 µm silica gel cartridge (eluting solvent: ethyl acetate). The fractions containing the desired product are combined and concentrated to dryness under reduced pressure. 0.92 g of additional 5-(5-methoxy-1H-benzimidazol-2-ylsulfanyl)-furan-2-carbaldehyde is obtained as a pale yellow powder. mp: 94-99° C.

Step 2: 9-[5-(5-Methoxy-1H-benzimidazol-2-ylsulfanyl)-furan-2-yl]-8-oxo-4,5,6,7,8,9-hexahydro-2H-pyrrolo[3,4-b]quinoline-3-carboxylic acid ethyl ester A suspension of 462.5 mg (3.0 mmol) of 3-amino-2-ethoxycarbonylpyrrole and 822.9 mg (3.0 mmol) of 5-(5-methoxy-1H-benzimidazol-2-ylsulfanyl)-furan-2-carbaldehyde (obtained from step 1) in 15 mL of ethanol under argon is stirred at room temperature for 1 hour. 1,3-Cyclohexanedione (336.4 mg, 3.0 mmol) is then added and the reaction mixture is heated at reflux temperature for 16 h. The mixture is then cooled to 0° C., filtered and the precipitate is washed with diisopropyl ether. The solid is then purified by chromatography on a prepacked 90 g 15-40 µm silica gel cartridge (eluting solvent: ethyl acetate/methanol/trifluoroacetic acid 98/1/1 v/v/v; rate: 40 mL/min). The fractions containing the desired product are combined and concentrated to dryness under reduced pressure. The residue is purified by chromatography on a prepacked 90 g 15-40 µm silica gel cartridge (eluting solvent: ethyl acetate/cyclohexane from 50/50 to 75/25 v/v; rate: 40 mL/min). The fractions containing the desired product are combined and concentrated to dryness under reduced pressure. 330 mg of 9-[5-(5-methoxy-1H-benzimidazol-2-ylsulfanyl)-furan-2-yl]-8-oxo-4,5,6,7,8,9-hexahydro-2H-pyrrolo[3,4-b]quinoline-3-carboxylic acid ethyl ester are obtained as a yellow powder. mp: 140° C. LCMS: m/z 505: [M+H]$^+$ (base peak); m/z 503: [M−H]$^−$ (base peak).

3-Amino-2-ethoxycarbonylpyrrole can be prepared as follows:

3-Amino-2-ethoxycarbonylpyrrole, hydrochloride (5.0 g, 26.2 mmol) is dissolved into 25 mL of dichloromethane under argon and 13.1 mL (26.2 mmol) of a 2N sodium hydroxide solution is added dropwise. The reaction mixture is stirred vigorously for 1 h and then decanted. The aqueous phase is extracted with 25 mL of dichloromethane. The organic extracts are combined, dried on magnesium sulfate, filtered and concentrated under reduced pressure. The residue is triturated in diisopropylether and concentrated to dryness. 3-Amino-2-ethoxycarbonylpyrrole (3.93 g) is obtained as an off-white powder. EI: m/z 154: [M]$^+$ m/z 126: [M]$^+$ —C2H5 m/z 108: [M]$^+$ —OC$_2$H$_5$ (base peak) m/z 80: 108 —CO.

EXAMPLE 111

9-[5-(6-Methoxy-1H-benzimidazol-2-ylsulfanyl)-furan-2-yl]-8-oxo-4,5,6,7,8,9-hexahydro-2H-pyrrolo[3,4-b][1,7]naphthyridine-3-carboxylic acid ethyl ester

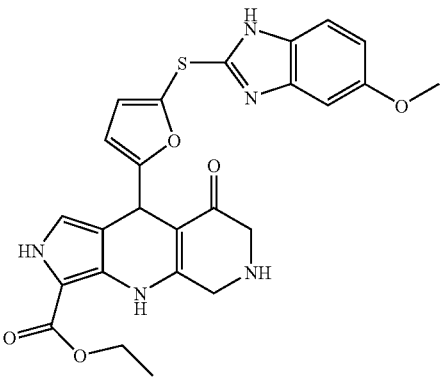

Step 1: 6-tert-Butyloxy-9-[5-(5-methoxy-1H-benzimidazol-2-ylsulfanyl)-furan-2-yl]-8-oxo-2,4,5,7,8,9-hexahydro-2H-pyrrolo[3,4-b][1,7]naphthyridine-3-carboxylic acid ethyl ester A suspension of 385.4 mg (2.5 mmol) of 3-amino-2-ethoxycarbonylpyrrole and 685.8 mg (2.5 mmol) of 5-(5-methoxy-1H-benzimidazol-2-ylsulfanyl)-furan-2-carbaldehyde in 15 mL of ethanol under argon is stirred at room temperature for 1 hour. N-Boc-3,5-diketopiperidine (533.1 mg, 2.5 mmol) is then added and the reaction mixture is heated at reflux temperature for 16 h. The mixture is then cooled to room temperature and concentrated to dryness under reduced pressure. The residue is purified by chromatography on a prepacked 90 g 15-40 μm silica gel cartridge (eluting solvent: ethyl acetate/methanol/triethylamine 92/4/4 v/v/v; rate: 40 mL/min). The fractions containing the desired product are combined and concentrated to dryness under reduced pressure. The residue is purified by chromatography on a prepacked 90 g 15-40 μm silica gel cartridge (eluting solvent: dichloromethane/methanol 80/20 v/v; rate: 40 mL/min). The fractions containing the desired product are combined and concentrated to dryness under reduced pressure. The residue is purified by chromatography on a prepacked 90 g 15-40 μm silica gel cartridge (eluting solvent: ethyl acetate/cyclohexane from 50/50 to 75/25 v/v; rate: 40 mL/min). The fractions containing the desired product are combined and concentrated to dryness under reduced pressure. 500 mg of 6-tert-butyloxy-9-[5-(5-methoxy-1H-benzimidazol-2-ylsulfanyl)-furan-2-yl]-8-oxo-2,4,5,7,8,9-hexahydro-2H-pyrrolo[3,4-b][1,7]naphthyridine-3-carboxylic acid ethyl ester are obtained as a yellow powder. mp: 156-166° C. LCMS: m/z 606: [M+H]+ (base peak); m/z 604: [M−H]− (base peak).

Step 2: 9-[5-(6-Methoxy-1H-benzimidazol-2-ylsulfanyl)-furan-2-yl]-8-oxo-4,5,6,7,8,9-hexahydro-2H-pyrrolo[3,4-b][1,7]naphthyridine-3-carboxylic acid ethyl ester 6-tert-Butyloxy-9-[5-(5-methoxy-1H-benzimidazol-2-ylsulfanyl)-furan-2-yl]-8-oxo-2,4,5,7,8,9-hexahydro-2H-pyrrolo[3,4-b][1,7]naphthyridine-3-carboxylic acid ethyl ester (470.0 mg, 0.78 mmol) is dissolved into 10 mL of dioxane. Then, 10.0 mL (40.0 mmol) of a 4N solution of hydrochloric acid in dioxane is added slowly. The reaction mixture is stirred at room temperature for 3 h, upon which it is concentrated to dryness under reduced pressure. The residue is diluted into dichloromethane, treated with water and decanted. The organic phase is separated and the aqueous phase is treated with a 1N sodium hydroxide solution up to pH 10. After extraction with dichloromethane followed by extraction with ethyl acetate, the ethyl acetate extracts are combined, dried on magnesium sulfate, filtered and concentrated under reduced pressure. 150 mg of 9-[5-(6-methoxy-1H-benzimidazol-2-ylsulfanyl)-furan-2-yl]-8-oxo-4,5,6,7,8,9-hexahydro-2H-pyrrolo[3,4-b][1,7]naphthyridine-3-carboxylic acid ethyl ester are obtained as a pale yellow powder. mp: 248° C. LCMS: m/z 506: [M+H]+ (base peak); m/z 504: [M−H]− (base peak). The dichloromethane extracts are combined, dried on magnesium sulfate, filtered and concentrated under reduced pressure. The residue is purified by chromatography on a prepacked 90 g 15-40 μm silica gel cartridge (eluting solvent: dichloromethane/methanol 90/10 v/v). The fractions containing the desired product are combined and concentrated to dryness under reduced pressure. 124 mg of additional 9-[5-(6-methoxy-1H-benzimidazol-2-ylsulfanyl)-furan-2-yl]-8-oxo-4,5,6,7,8,9-hexahydro-2H-pyrrolo[3,4-b][1,7]naphthyridine-3-carboxylic acid ethyl ester are obtained as a pale yellow powder.

EXAMPLE 112

9-[5-(3H-Imidazo[4,5-b]pyridin-2-ylsulfanyl)-furan-2-yl]-8-oxo-4,5,6,7,8,9-hexahydro-2H-pyrrolo[3,4-b]quinoline-3-carboxylic acid ethyl ester

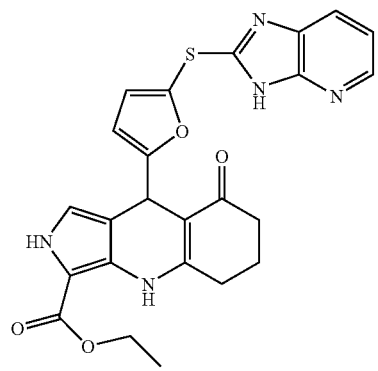

Step 1: 5-(1H-Imidazo[4,5-b]pyridin-2-ylsulfanyl)-furan-2-carbaldehyde

1H-Imidazo[4,5-b]pyridine-2-thiol (1.51 g, 10.0 mmol) is suspended into 80 mL of tetrahydrofuran under argon. Then, 0.72 g (15.0 mmol) of sodium hydride is added. The reaction mixture is stirred at room temperature until gas evolution has ceased. 5-Nitro-2-furaldehyde (1.41 g, 10.0 mmol) is then added and the reaction mixture is stirred at room temperature for 2.5 h, upon which it is poured on ice and extracted 3 times with ethyl acetate. The organic extracts are combined, washed with brine, dried on magnesium sulfate, filtered and concentrated under reduced pressure. The residue is recrystallized from ethyl acetate, filtered, washed with ethyl acetate and dried under reduced pressure. 1.34 g of 5-(1H-imidazo[4,5-b]pyridin-2-ylsulfanyl)-furan-2-carbaldehyde is obtained as a crystalline light-brown powder. mp: 188° C.

Step 2: 9-[5-(3H-Imidazo[4,5-b]pyridin-2-ylsulfanyl)-furan-2-yl]-8-oxo-4,5,6,7,8,9-hexahydro-2H-pyrrolo[3,4-b]quinoline-3-carboxylic acid ethyl ester A suspension of 69.2 mg (0.45 mmol) of 3-amino-2-ethoxycarbonylpyrrole and 110.0 mg (0.45 mmol) of 5-(1H-imidazo[4,5-b]pyridin-2-ylsulfanyl)-furan-2-carbaldehyde (obtained from step 1) in 5 mL of ethanol under argon is stirred at room temperature for 1 hour. 1,3-Cyclohexanedione (50.3 mg, 0.45 mmol) is then added and the reaction mixture is heated at reflux temperature for 16 h. The mixture is then cooled to room temperature and concentrated under reduced pressure. The residue is purified by chromatography on a prepacked 30 g 15-40 μm silica gel cartridge (eluting solvent: dichloromethane/methanol from 100/0 to 90/10 v/v). The fractions containing the desired product are combined and concentrated to dryness under reduced pressure. The residue is purified by chromatography on a prepacked 30 g 15-40 μm silica gel cartridge (eluting solvent: toluene/2-propanol 85/15 v/v). The fractions containing the desired product are combined and concentrated to dryness under reduced pressure. The residue is purified by chromatography on a prepacked 25 g 15-40 μm silica gel cartridge (eluting solvent: toluene/2-propanol 85/15 v/v). The fractions containing the desired product are combined and concentrated to dryness under reduced pressure. The residue is purified by chromatography on a prepacked 15 g 15-40 μm silica gel cartridge (eluting solvent: ethyl acetate/methanol/triethylamine 92/4/4 v/v/v). The fractions containing the desired product are combined and concentrated to dryness under reduced pressure. 37 mg of 9-[5-(3H-imidazo[4,5-b]pyridin-2-ylsulfanyl)-furan-2-yl]-8-oxo-4,5,6,7,8,9-hexahydro-2H-pyrrolo[3,4-b]quinoline-3-carboxylic acid ethyl ester are obtained as a yellow powder. mp: 190-202° C. LCMS: m/z 476: [M+H]$^+$ (base peak); m/z 474: [M−H]$^-$ (base peak).

3-Amino-2-ethoxycarbonylpyrrole can be prepared according to example 110.

EXAMPLE 113

9-[5-(3H-Imidazo[4,5-b]pyridin-2-ylsulfanyl)-furan-2-yl]-8-oxo-4,5,6,7,8,9-hexahydro-2H-pyrrolo[3,4-b][1,7]naphthyridine-3-carboxylic acid ethyl ester

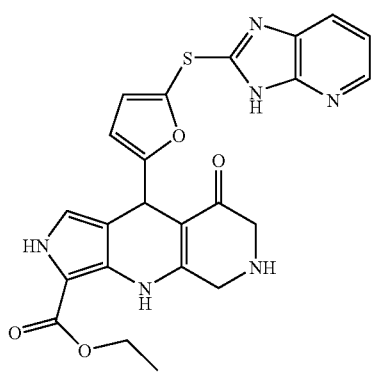

Step 1: 6-tert-Butyloxy-9-[5-(3H-Imidazo[4,5-b]pyridin-2-ylsulfanyl)-furan-2-yl]-8-oxo-2,4,5,7,8,9-hexahydro-2H-pyrrolo[3,4-b][1,7]naphthyridine-3-carboxylic acid ethyl ester A suspension of 308.3 mg (2.0 mmol) of 3-amino-2-ethoxycarbonylpyrrole and 490.5 mg (2.0 mmol) of 5-(1H-imidazo[4,5-b]pyridin-2-ylsulfanyl)-furan-2-carbaldehyde in 10 mL of n-butanol under argon is stirred at room temperature for 0.5 hour. N-Boc-3,5-diketopiperidine (426.5 mg, 2.0 mmol) is then added and the reaction mixture is heated at reflux temperature for 2 h. The mixture is then cooled to room temperature and concentrated to dryness under reduced pressure. The residue is purified by chromatography on a prepacked 90 g 15-40 μm silica gel cartridge (eluting solvent: dichloromethane/methanol from 100/0 to 90/10 v/v; rate: 40 mL/min). The fractions containing the desired product are combined and concentrated to dryness under reduced pressure. The residue is purified by chromatography on a prepacked 70 g 15-40 μm silica gel cartridge (eluting solvent: dichloromethane/acetonitrile/methanol from 60/40/0 to 75/20/5 v/v/v; rate: 40 mL/min). The fractions containing the desired product are combined and concentrated to dryness under reduced pressure. The residue is triturated in diethylether, filtered and dried under reduced pressure. 320 mg of 6-tert-butyloxy-9-[5-(3H-Imidazo[4,5-b]pyridin-2-ylsulfanyl)-furan-2-yl]-8-oxo-2,4,5,7,8,9-hexahydro-2H-pyrrolo[3,4-b][1,7]naphthyridine-3-carboxylic acid ethyl ester are obtained as a yellow powder. 400 MHz $^1$H NMR (DMSO-d$_6$) δ (ppm): 1.29 (t, J=7.0 Hz, 3H); 1.41 (large s, 9H); 3.75 (large m, 1H); 4.13 (d, J=17.5 Hz, 1H); 4.15 (masked m, 1H); 4.28 (q, J=7.0 Hz, 2H); 4.97 (d, J=17.5 Hz, 1H); 5.21 (s, 1H); 5.95 (d, J=3.5 Hz, 1H); 6.82 (d, J=3.5 Hz, 1H); 6.88 (d, J=3.5 Hz, 1H); 7.17 (dd, J=5.0, 8.0 Hz, 1H); 7.86 (large d, J=8.0 Hz, 1H); 8.25 (large d, J=5.0 Hz, 1H); 9.20 (large m, 1H); 11.5 (s, 1H); 13.1 (broad m, 1H).

Step 2: 9-[5-(3H-Imidazo[4,5-b]pyridin-2-ylsulfanyl)-furan-2-yl]-8-oxo-4,5,6,7,8,9-hexahydro-2H-pyrrolo[3,4-b][1,7]naphthyridine-3-carboxylic acid ethyl ester 6-tert-Butyloxy-9-[5-(5-methoxy-1H-benzimidazol-2-ylsulfanyl)-furan-2-yl]-8-oxo-2,4,5,7,8,9-hexahydro-2H-pyrrolo[3,4-b][1,7]naphthyridine-3-carboxylic acid ethyl ester (307.0 mg, 0.53 mmol) is dissolved into 10 mL of dioxane. Then, 10.0 mL (40.0 mmol) of a 4N solution of hydrochloric acid in dioxane is added slowly. The reaction mixture is stirred at room temperature for 3 h, upon which it is concentrated to dryness under reduced pressure. The residue is diluted into 80 mL of dichloromethane, treated with 50 mL of a 1N sodium hydroxide solution and decanted. The aqueous phase is extracted twice with dichloromethane and filtered. The solid is triturated in acetonitrile and filtered (operation repeated once), then dried under reduced pressure. 226 mg of 9-[5-(3H-imidazo[4,5-b]pyridin-2-ylsulfanyl)-furan-2-yl]-8-oxo-4,5,6,7,8,9-hexahydro-2H-pyrrolo[3,4-b][1,7]naphthyridine-3-carboxylic acid ethyl ester are obtained as a beige powder. LCMS: m/z 477: [M+H]$^+$ (base peak); m/z 475: [M−H]$^-$ (base peak). Anal. Calcd for $C_{23}H_{20}N_6O_4S$: C, 57.97; H, 4.23; N, 17.64; O, 13.43; S, 6.73. Found: C, 56.08; H, 4.49; N, 17.26; S, 6.13; $H_2O$, 3.26%.

3-Amino-2-ethoxycarbonylpyrrole can be prepared according to example 110.

EXAMPLE 114

9-[5-(5,6-Difluoro-1H-benzimidazol-2-ylsulfanyl)-furan-2-yl]-8-oxo-4,5,6,7,8,9-hexahydro-2H-pyrrolo[3,4-b]quinoline-3-carboxylic acid ethyl ester

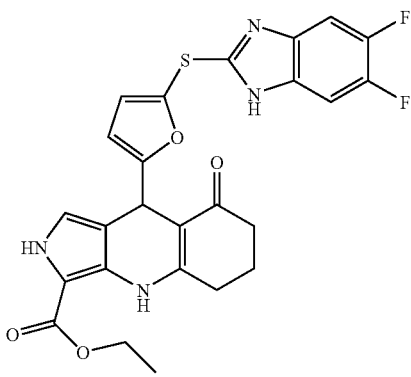

Step 1: 5-(5,6-Difluoro-1H-benzimidazol-2-ylsulfanyl)-furan-2-carbaldehyde 5,6-Difluoro-1,3-dihydro-benzimidazole-2-thione (1.0 g, 5.37 mmol) is suspended into 50 mL of tetrahydrofuran under argon. Then, 0.39 g (8.06 mmol) of sodium hydride is added. The reaction mixture is stirred at room temperature until gas evolution has ceased. 5-Nitro-2-furaldehyde (0.76 g, 5.37 mmol) is then added and the reaction mixture is stirred at room temperature for 16 h, upon which it is poured on ice and extracted 3 times with ethyl acetate. The organic extracts are combined, washed with brine, dried on magnesium sulfate, filtered and concentrated under reduced pressure. The residue is purified by chromatography on a prepacked 200 g 15-40 μm silica gel cartridge (eluting solvent: dichloromethane/methanol 95/5 v/v; rate: 40 mL/min). The fractions containing the desired product are combined and concentrated to dryness under reduced pressure. The residue is recrystallized from ethyl acetate/n-heptane, filtered, washed with n-heptane and dried under reduced pressure. 1.16 g of 5-(5,6-difluoro-1H-benzimidazol-2-ylsulfanyl)-furan-2-carbaldehyde is obtained as a crystalline brown powder. mp: 133° C.

Step 2: 9-[5-(5,6-Difluoro-1H-benzimidazol-2-ylsulfanyl)-furan-2-yl]-8-oxo-4,5,6,7,8,9-hexahydro-2H-pyrrolo[3,4-b]quinoline-3-carboxylic acid ethyl ester A suspension of 308.3 mg (2.0 mmol) of 3-amino-2-ethoxycarbonylpyrrole and 560.5 mg (2.0 mmol) of 5-(5,6-difluoro-1H-benzimidazol-2-ylsulfanyl)-furan-2-carbaldehyde (obtained from step 1) in 10 mL of ethanol under argon is stirred at room temperature for 1 hour. 1,3-Cyclohexanedione (224.3 mg, 2.0 mmol) is then added and the reaction mixture is heated at reflux temperature for 16 h. The mixture is then cooled in an ice bath and the precipitate is filtered. The filtrate is concentrated to dryness under reduced pressure and the residue is purified by chromatography on a prepacked 90 g 15-40 μm silica gel cartridge (eluting solvent: ethyl acetate/cyclohexane 50/50 v/v; rate: 40 mL/min). The fractions containing the desired product are combined and concentrated to dryness under reduced pressure. The residue is recrystallized from ethyl acetate/n-heptane and then from ethyl acetate, filtered and dried under reduced pressure. 189 mg of 9-[5-(5,6-difluoro-1H-benzimidazol-2-ylsulfanyl)-furan-2-yl]-8-oxo-4,5,6,7,8,9-hexahydro-2H-pyrrolo[3,4-b]quinoline-3-carboxylic acid ethyl ester are obtained as an off-white crystalline powder. mp: 160-170° C. LCMS: m/z 511: [M+H]+ (base peak); m/z 509: [M−H]− (base peak). The filtrate is concentrated to dryness under reduced pressure and the residue is purified by chromatography on a prepacked 90 g 15-40 μm silica gel cartridge (eluting solvent: ethyl acetate; rate: 40 mL/min). The fractions containing the desired product are combined and concentrated to dryness under reduced pressure. 220 mg of additional 9-[5-(5,6-difluoro-1H-benzimidazol-2-ylsulfanyl)-furan-2-yl]-8-oxo-4,5,6,7,8,9-hexahydro-2H-pyrrolo[3,4-b]quinoline-3-carboxylic acid ethyl ester are obtained as an off-white powder. mp: 160-170° C. LCMS: m/z 511: [M+H]+ (base peak); m/z 509: [M−H]− (base peak).

3-Amino-2-ethoxycarbonylpyrrole can be prepared according to example 110.

EXAMPLE 115

9-[5-(5,6-Difluoro-1H-benzimidazol-2-ylsulfanyl)-furan-2-yl]-8-oxo-4,5,6,7,8,9-hexahydro-2H-pyrrolo[3,4-b][1,7]naphthyridine-3-carboxylic acid ethyl ester

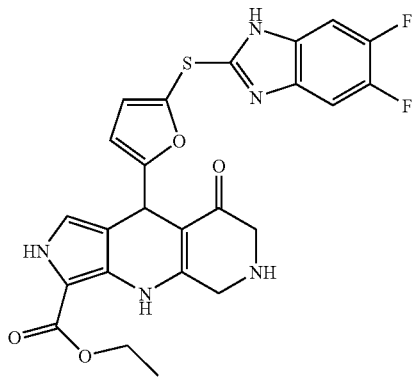

Step 1: 6-tert-Butyloxy-9-[5-(5,6-difluoro-1H-benzimidazol-2-ylsulfanyl)-furan-2-yl]-8-oxo-2,4,5,7,8,9-hexahydro-2H-pyrrolo[3,4-b][1,7]naphthyridine-3-carboxylic acid ethyl ester A suspension of 308.3 mg (2.0 mmol) of 3-amino-2-ethoxycarbonylpyrrole and 560.5 mg (2.0 mmol) of 5-(5,6-difluoro-1H-benzimidazol-2-ylsulfanyl)-furan-2-carbaldehyde in 10 mL of ethanol under argon is stirred at room temperature for 1 hour. N-Boc-3,5-diketopiperidine (426.5 mg, 2.0 mmol) is then added and the reaction mixture is heated at reflux temperature for 16 h. The mixture is then cooled to room temperature and concentrated to dryness under reduced pressure. The residue is purified by chromatography on a prepacked 90 g 15-40 μm silica gel cartridge (eluting solvent: ethyl acetate/cyclohexane 50/50 v/v; rate: 40 mL/min). The fractions containing the desired product are combined and concentrated to dryness under reduced pressure. The residue is recrystallized from ethyl acetate, filtered, washed with ethyl acetate and dried under reduced pressure. 420 mg of 6-tert-butyloxy-9-[5-(5-methoxy-1H-benzimidazol-2-ylsulfanyl)-furan-2-yl]-8-oxo-2,4,5,7,8,9-hexahydro-2H-pyrrolo[3,4-b][1,7]naphthyridine-3-carboxylic acid ethyl ester are obtained as a yellow powder. LCMS: m/z 612: [M+H]+ (base peak); m/z 610: [M−H]− (base peak).

Step 2: 9-[5-(5,6-Difluoro-1H-benzimidazol-2-ylsulfanyl)-furan-2-yl]-8-oxo-4,5,6,7,8,9-hexahydro-2H-pyrrolo[3,4-b][1,7]naphthyridine-3-carboxylic acid ethyl ester 6-tert-Butyloxy-9-[5-(5,6-difluoro-1H-benzimidazol-2-ylsulfanyl)-furan-2-yl]-8-oxo-2,4,5,7,8,9-hexahydro-2H-pyrrolo[3,4-b][1,7]naphthyridine-3-carboxylic acid ethyl ester (420.0 mg, 0.69 mmol) is dissolved into 10 mL of dioxane. Then, 10.0 mL (40.0 mmol) of a 4N solution of hydrochloric acid in dioxane is added slowly. The reaction mixture is stirred at room temperature for 3 h, upon which it is concentrated to dryness under reduced pressure. The residue is diluted into dichloromethane, treated with water and decanted. The organic phase is separated and the aqueous phase is treated with a 1N sodium hydroxide solution up to pH 10. After 3 extractions with ethyl acetate, the organic extracts are combined, dried on magnesium sulfate, filtered and concentrated under reduced pressure. 194 mg of 9-[5-(5,6-difluoro-1H-benzimidazol-2-ylsulfanyl)-furan-2-yl]-8-oxo-4,5,6,7,8,9-hexahydro-2H-pyrrolo[3,4-b][1,7]naphthyridine-3-carboxylic acid ethyl ester are obtained as a beige powder. mp: 190-196° C. LCMS: m/z 512: [M+H]$^+$ (base peak); m/z 510: [M−H]$^−$ (base peak).

3-Amino-2-ethoxycarbonylpyrrole can be prepared according to example 110.

EXAMPLE 116

9-[5-(5,6-Dichloro-1H-benzimidazol-2-ylsulfanyl)-furan-2-yl]-8-oxo-4,5,6,7,8,9-hexahydro-2H-pyrrolo[3,4-b]quinoline-3-carboxylic acid ethyl ester

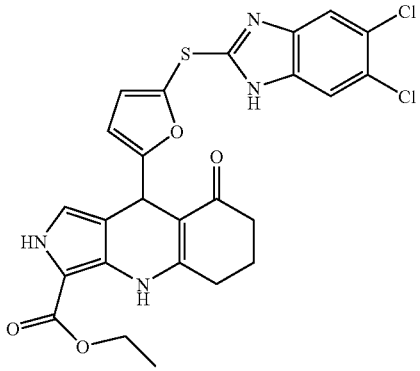

Step 1: 5-(5,6-Dichloro-1H-benzimidazol-2-ylsulfanyl)-furan-2-carbaldehyde 5,6-Dichloro-1H-benzimidazole-2-thiol (1.0 g, 4.56 mmol) is suspended into 50 mL of tetrahydrofuran under argon. Then, 0.33 g (6.85 mmol) of sodium hydride is added. The reaction mixture is stirred at room temperature until gas evolution has ceased. 5-Nitro-2-furaldehyde (0.64 g, 4.57 mmol) is then added and the reaction mixture is stirred at room temperature for 1 h, upon which it is poured on ice and extracted 3 times with ethyl acetate. The organic extracts are combined, washed with brine, dried on magnesium sulfate, filtered and concentrated under reduced pressure. The residue is purified by chromatography on a prepacked 200 g 15-40 µm silica gel cartridge (eluting solvent: ethyl acetate/cyclohexane 50/50 v/v; rate: 50 mL/min). The fractions containing the desired product are combined and concentrated to dryness under reduced pressure. The residue is triturated in diisopropyl ether, filtered and dried under reduced pressure. 0.93 g of 5-(5,6-dichloro-1H-benzimidazol-2-ylsulfanyl)-furan-2-carbaldehyde is obtained as a yellow powder. mp: 170° C.

Step 2: 9-[5-(5,6-Dichloro-1H-benzimidazol-2-ylsulfanyl)-furan-2-yl]-8-oxo-4,5,6,7,8,9-hexahydro-2H-pyrrolo[3,4-b]quinoline-3-carboxylic acid ethyl ester A suspension of 231.3 mg (1.5 mmol) of 3-amino-2-ethoxycarbonylpyrrole and 469.7 mg (1.5 mmol) of 5-(5,6-dichloro-1H-benzimidazol-2-ylsulfanyl)-furan-2-carbaldehyde (obtained from step 1) in 7.5 mL of n-butanol under argon is stirred at room temperature until complete dissolution. 1,3-Cyclohexanedione (168.2 mg, 1.5 mmol) is then added and the reaction mixture is heated at reflux temperature for 1.5 h. The mixture is then cooled to room temperature and concentrated under reduced pressure. The residue is purified by chromatography on a prepacked 90 g 15-40 µm silica gel cartridge (eluting solvent: dichloromethane/methanol 100/0 to 90/10 v/v; rate: 40 mL/min). The fractions containing the desired product are combined and concentrated to dryness under reduced pressure. The residue is recrystallized from ethanol and the solid is filtered, washed with ethanol and dried under reduced pressure. 431 mg of 9-[5-(5,6-dichloro-1H-benzimidazol-2-ylsulfanyl)-furan-2-yl]-8-oxo-4,5,6,7,8,9-hexahydro-2H-pyrrolo[3,4-b]quinoline-3-carboxylic acid ethyl ester are obtained as a beige crystalline powder. mp: 180° C. LCMS: m/z 543: [M+H]$^+$ (base peak). EA.

3-Amino-2-ethoxycarbonylpyrrole can be prepared according to example 110.

EXAMPLE 117

9-[5-(3H-Imidazo[4,5-c]pyridin-2-ylsulfanyl)-furan-2-yl]-8-oxo-4,5,6,7,8,9-hexahydro-2H-pyrrolo[3,4-b]quinoline-3-carboxylic acid ethyl ester

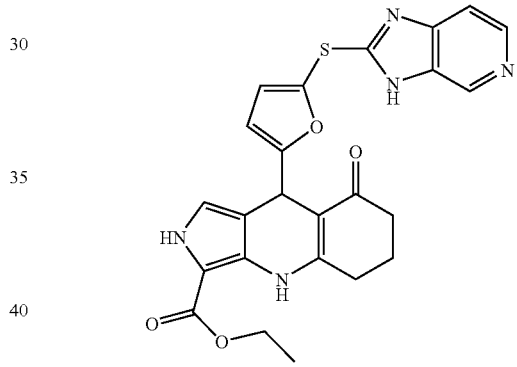

Step 1: 5-(3H-Imidazo[4,5-c]pyridin-2-ylsulfanyl)-furan-2-carbaldehyde

3H-Imidazo[4,5-c]pyridine-2-thiol (1.51 g, 10.0 mmol) is suspended into 80 mL of tetrahydrofuran under argon. Then, 0.72 g (15.0 mmol) of sodium hydride is added. The reaction mixture is stirred at room temperature until gas evolution has ceased. 5-Nitro-2-furaldehyde (1.41 g, 10.0 mmol) is then added and the reaction mixture is stirred at room temperature for 16 h, upon which it is poured on ice and extracted 3 times with ethyl acetate. The organic extracts are combined and filtered. The filtrate is washed with brine, dried on magnesium sulfate, filtered and concentrated under reduced pressure. The residue is purified by chromatography on a prepacked 70 g 15-40 µm silica gel cartridge (eluting solvent: dichloromethane/acetonitrile/methanol from 75/20/5 to 90/0/10 v/v/v; rate: 40 mL/min). The fractions containing the desired product are combined and concentrated to dryness under reduced pressure. The residue is triturated in diethyl ether, filtered and dried under reduced pressure. 270 mg of 5-(3H-imidazo[4,5-c]pyridin-2-ylsulfanyl)-furan-2-carbaldehyde are obtained as a crystalline yellow powder. LCMS: m/z 246: [M+H]$^+$ (base peak); m/z 244: [M−H]$^−$ (base peak).

3H-Imidazo[4,5-c]pyridine-2-thiol can be prepared according to patent WO 2004/052288.

Step 2: 9-[5-(3H-Imidazo[4,5-c]pyridin-2-ylsulfanyl)-furan-2-yl]-8-oxo-4,5,6,7,8,9-hexahydro-2H-pyrrolo[3,4-b]quinoline-3-carboxylic acid ethyl ester A suspension of 154.2 mg (1.0 mmol) of 3-amino-2-ethoxycarbonylpyrrole and 245.3 mg (1.0 mmol) of 5-(3H-imidazo[4,5-c]pyridin-2-ylsulfanyl)-furan-2-carbaldehyde (obtained from step 1) in 10 mL of n-butanol under argon is stirred at room temperature for 15 min. 1,3-Cyclohexanedione (112.1 mg, 1.0 mmol) is then added and the reaction mixture is heated at reflux temperature for 2 h. The mixture is then cooled to room temperature and concentrated under reduced pressure. The residue is triturated in ethanol, filtered and washed with diethyl ether. The solid is purified by chromatography on a prepacked 70 g 15-40 μm silica gel cartridge (eluting solvent: dichloromethane/methanol from 100/0 to 80/20 v/v; rate: 40 mL/min). The fractions containing the desired product are combined and concentrated to dryness under reduced pressure. 178 mg of 9-[5-(3H-imidazo[4,5-c]pyridin-2-ylsulfanyl)-furan-2-yl]-8-oxo-4,5,6,7,8,9-hexahydro-2H-pyrrolo[3,4-b]quinoline-3-carboxylic acid ethyl ester are obtained as a beige powder. LCMS: m/z 476: [M+H]$^+$ (base peak). Anal. Calcd for $C_{24}H_{21}N_5O_4S$: C, 60.62; H, 4.45; N, 14.73; O, 13.46; S, 6.74. Found: C, 59.41; H, 4.47; N, 14.33; S, 6.41; $H_2O$, 2.11%.

3-Amino-2-ethoxycarbonylpyrrole can be prepared according to example 110.

EXAMPLE 118

9-[2-(1H-Benzimidazol-2-ylsulfanyl)-thiazol-5-yl]-8-oxo-4,5,6,7,8,9-hexahydro-2H-pyrrolo[3,4-b]quinoline-3-carboxylic acid ethyl ester

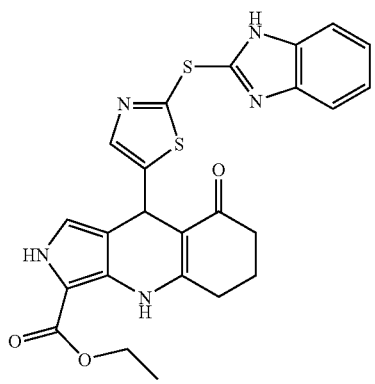

Step 1: 2-(1H-Benzimidazol-2-ylsulfanyl)-thiazole-5-carbaldehyde 1,3-Dihydro-benzimidazole-2-thione (1.0 g, 6.66 mmol) is suspended into 50 mL of tetrahydrofuran under argon. Then, 479 mg (9.99 mmol) of sodium hydride is added. The reaction mixture is stirred at room temperature until gas evolution has ceased. 2-Chloro-1,3-thiazole-5-carbaldehyde (983 mg, 6.66 mmol) is then added and the reaction mixture is stirred at room temperature for 2 h, upon which it is filtered. The solid is washed with tetrahydrofuran and dried under reduced pressure. The residue is diluted with water and extracted twice with ethyl acetate and once with dichloromethane. The organic extracts are combined, dried on magnesium sulfate, filtered and concentrated under reduced pressure. 1.23 g of 2-(1H-benzimidazol-2-ylsulfanyl)-thiazole-5-carbaldehyde is obtained as a pale yellow powder. mp: 188° C.

Step 2: 9-[2-(1H-Benzimidazol-2-ylsulfanyl)-thiazol-5-yl]-8-oxo-4,5,6,7,8,9-hexahydro-2H-pyrrolo[3,4-b]quinoline-3-carboxylic acid ethyl ester A suspension of 308.3 mg (2.0 mmol) of 3-amino-2-ethoxycarbonylpyrrole and 522.7 mg (2.0 mmol) of 2-(1H-benzimidazol-2-ylsulfanyl)-thiazole-5-carbaldehyde (obtained from step 1) in 10 mL of n-butanol under argon is stirred at room temperature for 0.5 hour. 1,3-Cyclohexanedione (224.3 mg, 2.0 mmol) is then added and the reaction mixture is heated at reflux temperature for 2 h. The mixture is then cooled to room temperature and concentrated under reduced pressure. The residue is purified by chromatography on a prepacked 70 g 15-40 μm silica gel cartridge (eluting solvent: ethyl acetate; rate: 40 mL/min). The fractions containing the desired product are combined and concentrated to dryness under reduced pressure. The residue is triturated in ethanol, filtered, washed with diethylether and dried under reduced pressure. 313 mg of 9-[2-(1H-benzimidazol-2-ylsulfanyl)-thiazol-5-yl]-8-oxo-4,5,6,7,8,9-hexahydro-2H-pyrrolo[3,4-b]quinoline-3-carboxylic acid ethyl ester are obtained as a yellow powder. mp: 194° C. LCMS: m/z 492: [M+H]$^+$ (base peak); m/z 490: [M−H]$^-$ (base peak).

3-Amino-2-ethoxycarbonylpyrrole can be prepared according to example 110.

EXAMPLE 119

(+)-9-[5-(1H-Benzimidazol-2-ylsulfanyl)-furan-2-yl]-8-oxo-4,5,6,7,8,9-hexahydro-2H-pyrrolo[3,4-b]quinoline-3-carboxylic acid ethyl ester and (−)-9-[5-(1H-Benzimidazol-2-ylsulfanyl)-furan-2-yl]-8-oxo-4,5,6,7,8,9-hexahydro-2H-pyrrolo[3,4-b]quinoline-3-carboxylic acid ethyl ester

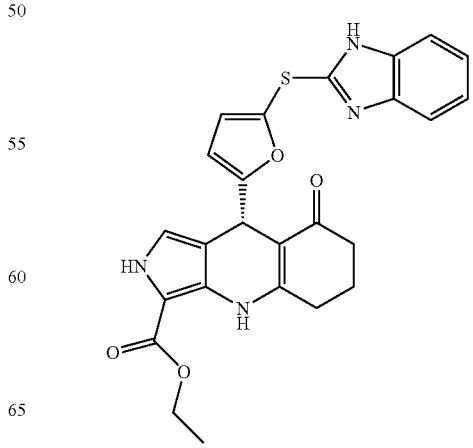

and

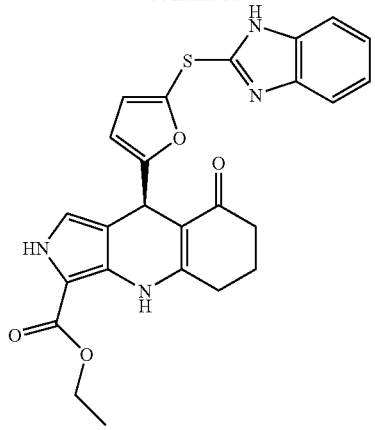

9-[5-(1H-Benzimidazol-2-ylsulfanyl)-furan-2-yl]-8-oxo-4,5,6,7,8,9-hexahydro-2H-pyrrolo[3,4-b]quinoline-3-carboxylic acid ethyl ester (304 mg) was resolved via preparative chiral HPLC (column: Pirkle Whelk 01 SS 10 μm 730 g 360×60 mm; eluting solvent: n-heptane/ethanol 70/30 v/v+ 0.1% diisopropylethylamine; rate: 90-125 mL/min; detection=254 nm). 118 mg of (+)-9-[5-(1H-benzimidazol-2-yl-sulfanyl)-furan-2-yl]-8-oxo-4,5,6,7,8,9-hexahydro-2H-pyrrolo[3,4-b]quinoline-3-carboxylic acid ethyl ester were obtained as a yellow powder. LCMS: m/z 475: [M+H]$^+$ (base peak); m/z 473: [M−H]$^−$ (base peak). Enantiomeric purity (chiral HPLC column: Pirkle Whelk 01 SS 10 μm 250×4.6 mm; eluting solvent: n-heptane/ethanol 70/30 v/v+0.1% diisopropylethylamine; rate: 1 mL/min; detection=254 nm): >99%. $\alpha_D$=+192.80° +/−2.7 (c=1.822 mg/0.5 mL CH$_3$OH). 110 mg of (−)-9-[5-(1 H-benzimidazol-2-ylsulfanyl)-furan-2-yl]-8-oxo-4,5,6,7,8,9-hexahydro-2H-pyrrolo[3,4-b]quinoline-3-carboxylic acid ethyl ester were obtained as a yellow powder. LCMS: m/z 475: [M+H]$^+$ (base peak); m/z 473: [M−H]$^−$ (base peak). Enantiomeric purity: >98%. $\alpha_D$=−160.10° +/−2.1. (c=2.590 mg/0.5 mL CH$_3$OH).

EXAMPLE 120

(+)-9-[5-(1H-Benzimidazol-2-ylsulfanyl)-furan-2-yl]-8-oxo-4,5,6,7,8,9-hexahydro-2H-pyrrolo[3,4-b]quinoline-3-carboxylic acid ethyl ester and (−)-9-[5-(1H-Benzimidazol-2-ylsulfanyl)-furan-2-yl]-8-oxo-4,5,6,7,8,9-hexahydro-2H-pyrrolo[3,4-b]quinoline-3-carboxylic acid ethyl ester

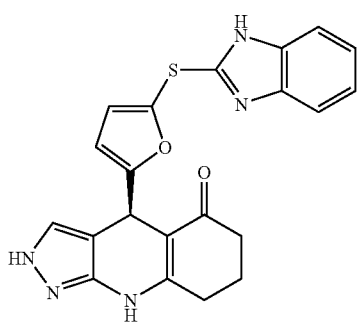

and

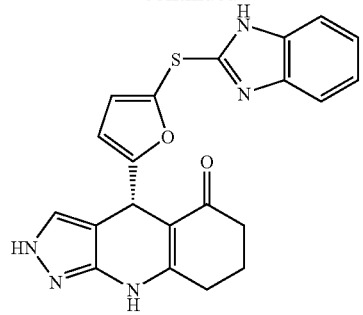

4-[5-(1H-Benzimidazol-2-ylsulfanyl)-furan-2-yl]-1,4,6,7,8,9-hexahydro-pyrazolo[3,4-b]quinolin-5-one (162 mg) was resolved via preparative chiral HPLC (column: Pirkle Whelk 01 SS 10 μm 730 g 350×60 mm; eluting solvent: n-heptane/2-propanol/methanol 50/40/10 v/v/v+0.1% triethylamine; rate: 90-125 mL/min; detection=254 nm). 69 mg of (+)-9-[5-(1H-benzimidazol-2-ylsulfanyl)-furan-2-yl]-8-oxo-4,5,6,7,8,9-hexahydro-2H-pyrrolo[3,4-b]quinoline-3-carboxylic acid ethyl ester were obtained as a crystalline pale-yellow powder. MS El: m/z 403: [M]$^+$ m/z 187: [M]$^+$ —C$_{11}$H$_7$N$_2$OS (base peak) m/z 159: 187 —CO. Enantiomeric purity (chiral HPLC column: Pirkle Whelk 01 SS 10 μm 250×4.6 mm; eluting solvent: n-heptane/2-propanol/methanol 50/40/10 v/v/v+0.1% triethylamine; rate: 1 mL/min; detection=254 nm): >99%. $\alpha_D$=+215.50° +/−2.9 (c=1.991 mg/0.5 mL CH$_3$OH). 84 mg of (−)-9-[5-(1H-benzimidazol-2-ylsulfanyl)-furan-2-yl]-8-oxo-4,5,6,7,8,9-hexahydro-2H-pyrrolo[3,4-b]quinoline-3-carboxylic acid ethyl ester were obtained as a crystalline pale-yellow powder. MS El: m/z 403: [M]$^+$ m/z 254: [M]$^+$ —C$_7$H$_5$N$_2$S (base peak); m/z 187: 254 —C$_4$H$_2$O. Enantiomeric purity: >98%. $\alpha_D$=−204.70° +/−2.7 (c=2.190 mg/0.5 mL CH$_3$OH).

EXAMPLE 121

9-[5-(6,7-Difluoro-1H-benzimidazol-2-ylsulfanyl)-furan-2-yl]-8-oxo-4,5,6,7,8,9-hexahydro-2H-pyrrolo[3,4-b]quinoline-3-carboxylic acid ethyl ester

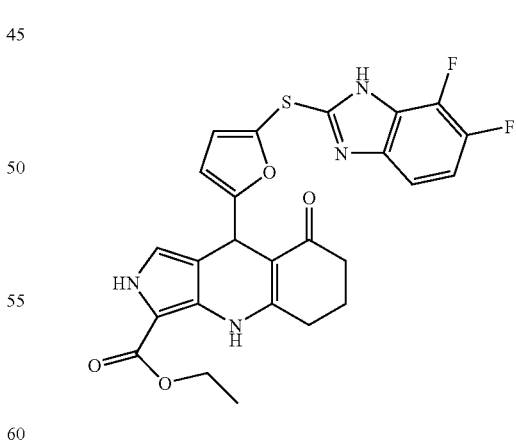

Step 1: 6,7-Difluoro-1H-benzimidazole-2-thiol

To a solution of 1,2-diamino-3,4-difluoro-benzene (996 mg, 6.9 mmol) in 20 mL of ethanol in a 25 mL microwave tube, are added 2.0 mL (33.3 mmol) of carbon disulfide. The tube is capped and the reaction mixture is heated under microwaves at 120° C. twice for 20 minutes, upon which 1.0 mL (16.6 mmol) of carbon disulfide is added and heating under microwaves is pursued for 20 minutes. Carbon disulfide 2.0 mL (33.3 mmol) is added and heating is pursued for 30 minutes under microwaves at 150° C. The reaction mixture is then cooled to room temperature and concentrated to dryness under reduced pressure. The residue is dissolved into ethyl acetate and concentrated to dryness under reduced pressure. The residue is triturated into diisopropylether, filtered and washed once with diisopropylether. The solid is dried under reduced pressure. 0.35 g of 6,7-difluoro-1H-benzimidazole-2-thiol is obtained as mauve solid. LCMS-DAD-ELSD: 185 (−): [M−H]⁻; 186(+): [M+H]⁺.

Step 2: 5-(6,7-Difluoro-1H-benzimidazol-2-ylsulfanyl)-furan-2-carbaldehyde 6,7-Difluoro-1H-benzimidazole-2-thiol (0.34 g, 1.81 mmol) is suspended into 20 mL of tetrahydrofuran (THF) under argon. Then, 130 mg (2.71 mmol) of sodium hydride are added. The reaction mixture is stirred at room temperature until gas evolution has ceased. 5-Nitro-2-furaldehyde (0.25 g, 1.81 mmol) is then added and the reaction mixture is stirred at room temperature for 3 h, upon which it is poured on ice and extracted twice with ethyl acetate. The organic extracts are combined, washed with brine, dried on magnesium sulfate, filtered and concentrated under reduced pressure. The residue is purified by chromatography on a prepacked 70 g 15-40 μm silica gel cartridge (eluting solvent: dichloromethane/THF from 100/0 to 80/20 v/v; rate: 40 mL/min). The fractions containing the desired product are combined and concentrated to dryness under reduced pressure. The residue is purified by chromatography on a prepacked 30 g 15-40 μm silica gel cartridge (eluting solvent: dichloromethane/methanol from 100/0 to 95/5 v/v; rate: 20 mL/min). The fractions containing the desired product are combined and concentrated to dryness under reduced pressure. 0.28 g of 5-(6,7-difluoro-1H-benzimidazol-2-ylsulfanyl)-furan-2-carbaldehyde is obtained as a pale yellow meringue. LCMS-DAD-ELSD: 281(+): [M+H]⁺.

Step 3: 9-[5-(6,7-Difluoro-1H-benzimidazol-2-ylsulfanyl)-furan-2-yl]-8-oxo-4,5,6,7,8,9-hexahydro-2H-pyrrolo[3,4-b]quinoline-3-carboxylic acid ethyl ester A suspension of 148.5 mg (0.96 mmol) of 3-amino-2-ethoxycarbonylpyrrole and 269.9 mg (0.96 mmol) of 5-(6,7-difluoro-1H-benzimidazol-2-ylsulfanyl)-furan-2-carbaldehyde (obtained from step 2) in 10 mL of n-butanol under argon is stirred at room temperature for 20 minutes. 1,3-Cyclohexanedione (108.0 mg, 0.96 mmol) is then added and the reaction mixture is heated at reflux temperature for 2 h. The mixture is then cooled to room temperature and concentrated under reduced pressure. The residue is taken up in ethanol, cooled to 0° C., triturated, filtered and washed 3 times with ethanol. 127 mg of 9-[5-(6,7-difluoro-1H-benzimidazol-2-ylsulfanyl)-furan-2-yl]-8-oxo-4,5,6,7,8,9-hexahydro-2H-pyrrolo[3,4-b]quinoline-3-carboxylic acid ethyl ester are obtained as a light-yellow crystalline powder. mp: 144-148° C. LCMS-DAD-ELSD: 509(−): [M−H]⁻; 511 (+): [M+H]⁺.

3-Amino-2-ethoxycarbonylpyrrole can be prepared according to example 110.

EXAMPLE 122

8-Oxo-9-[5-(4,5,6-trifluoro-1H-benzimidazol-2-ylsulfanyl)-furan-2-yl]-4,5,6,7,8,9-hexahydro-2H-pyrrolo[3,4-b]quinoline-3-carboxylic acid ethyl ester

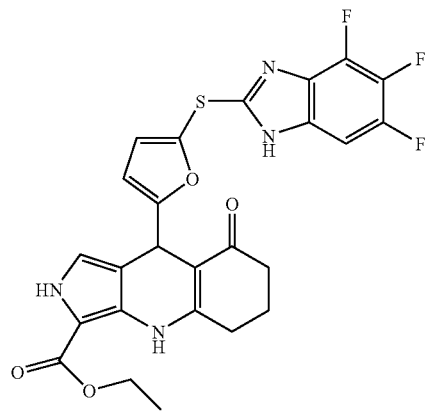

Step 1: 4,5,6-Trifluoro-1,3-dihydro-benzimidazole-2-thione

To a solution of 1,2-diamino-3,4,5-trifluoro-benzene (2.5 g, 15.4 mmol) in 20 mL of tetrahydrofuran under argon, are added 2.3 mL (38.6 mmol) of carbon disulfide. The reaction mixture is heated at reflux temperature for 3 h, upon which 2.3 mL (38.6 mmol) of carbon disulfide are added and reflux is maintained for 16 h. Carbon disulfide 2.3 mL (38.6 mmol) is added and reflux is maintained for 8 h, upon which 2.3 mL (38.6 mmol) of carbon disulfide are added and reflux is maintained for 16 h. The reaction mixture is then cooled to room temperature and concentrated to dryness under reduced pressure. The residue is purified by chromatography on a prepacked 90 g 15-40 μm silica gel cartridge (eluting solvent: cyclohexane/ethyl acetate 90/10 v/v; rate: 35 mL/min). The fractions containing the desired product are combined and concentrated to dryness under reduced pressure. The residue is purified by chromatography on a prepacked 90 g 15-40 μm silica gel cartridge (eluting solvent: dichloromethane/methanol 100/0, then 98/2 v/v; rate: 40 mL/min). The fractions containing the desired product are combined and concentrated to dryness under reduced pressure. 0.72 g of 4,5,6-trifluoro-1,3-dihydro-benzimidazole-2-thione is obtained as an off-white solid. LCMS-DAD-ELSD: 203(−): [M−H]⁻; 205(+): [M+H]⁺.

Step 2: 5-(4,5,6-Trifluoro-1H-benzimidazol-2-ylsulfanyl)-furan-2-carbaldehyde 4,5,6-Trifluoro-1,3-dihydro-benzimidazole-2-thione (0.72 g, 3.52 mmol) is suspended into 40 mL of tetrahydrofuran under argon. Then, 0.3 g (7.1 mmol) of sodium hydride are added. The reaction mixture is stirred at room temperature until gas evolution has ceased. 5-Nitro-2-furaldehyde (0.5 g, 3.5 mmol) is then added and the reaction mixture is stirred at room temperature for 88 h, upon which it is poured on 40 mL of ice-water and extracted 3 times with 60 mL of ethyl acetate.

The organic extracts are combined, washed with 150 mL of brine, dried on magnesium sulfate, filtered and concentrated under reduced pressure. The residue is diluted into 50 mL of water and 100 mL of dichloromethane. The aqueous phase is extracted twice with 100 mL of dichloromethane. The organic extracts are combined, washed with 100 mL of water, dried on magnesium sulfate, filtered and concentrated under reduced pressure. The residue is purified by chromatography on a prepacked 30 g 15-40 μm silica gel cartridge (eluting solvent: dichloromethane/methanol from 100/0 to 98/2 v/v; rate: 30 mL/min). The fractions containing the desired product are combined and concentrated to dryness under reduced pressure. The residue is taken up in diethyl ether and concentrated to dryness under reduced pressure. 0.28 g of 5-(4,5,6-trifluoro-1H-benzimidazol-2-ylsulfanyl)-furan-2-carbaldehyde is obtained as a pale yellow meringue. mp: 152° C.

Step 3: 8-oxo-9-[5-(4,5,6-trifluoro-1H-benzimidazol-2-ylsulfanyl)-furan-2-yl]-4,5,6,7,8,9-hexahydro-2H-pyrrolo[3,4-b]quinoline-3-carboxylic acid ethyl ester A suspension of 190 mg (1.23 mmol) of 3-amino-2-ethoxycarbonylpyrrole and 367 mg (1.23 mmol) of 5-(4,5,6-trifluoro-1H-benzimidazol-2-ylsulfanyl)-furan-2-carbaldehyde (obtained from step 2) in 6.5 mL of n-butanol under argon is stirred at room temperature for 15 minutes. 1,3-Cyclohexanedione (138 mg, 1.23 mmol) is then added and the reaction mixture is heated at reflux temperature for 2 h. The mixture is then cooled to room temperature and concentrated under reduced pressure. The residue is taken up in 5 mL of ethanol, cooled to 0° C. and triturated. The solid is filtered, washed with 1 mL of ethanol and 3 times with 5 mL of diisopropylether and dried under reduced pressure. 144 mg of 8-oxo-9-[5-(4,5,6-trifluoro-1H-benzimidazol-2-ylsulfanyl)-furan-2-yl]-4,5,6,7,8,9-hexahydro-2H-pyrrolo[3,4-b]quinoline-3-carboxylic acid ethyl ester are obtained as a yellow crystalline powder. mp: 186° C. LCMS-DAD-ELSD: 527(−): [M−H]⁻; 529(+): [M+H]⁺.

3-Amino-2-ethoxycarbonylpyrrole can be prepared according to example 110

EXAMPLE 123

9-[5-(5-Hydroxy-1H-benzimidazol-2-ylsulfanyl)-furan-2-yl]-8-oxo-4,5,6,7,8,9-hexahydro-2H-pyrrolo[3,4-b]-1,7-naphthyridine-3-carboxylic acid ethyl ester hydrochloride

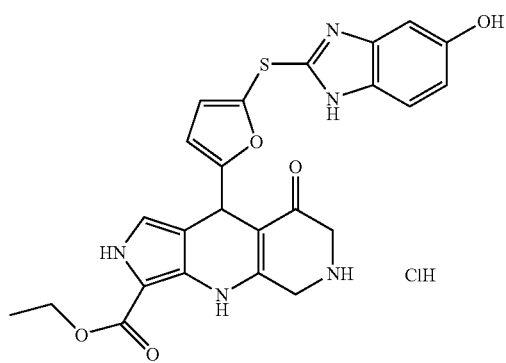

tert-Butyldimethylsilyl-, Boc-Protected Intermediate Preparation

A mixture of 3-amino-2-ethoxycarbonyl-pyrrole (0.165 g, 107 mmol), 5-[5-(tert-butyl-dimethyl-silanyloxy)-1H-benzimidazol-2-ylsulfanyl]-furan-2-carbaldehyde (described in example 89), 0.400 g, 1.068 mmol) and N-Boc-3,5-diketopiperidine (0.228 g, 1.07 mmol) in 4 ml of 1-butanol is heated at reflux temperature for 3 hours. The reaction mixture is then concentrated under reduced pressure and the residue is purified on a silica gel column (50 g) eluted successively with cyclohexane/ethyl acetate (9/1, v/v) and cyclohexane/ethyl acetate (7/3, v/v) to yield 500 mg of 6-tert-butyloxy-9-{5-[5-(tert-butyl-dimethyl-silanyloxy)-1H-benzimidazol-2-ylsulfanyl]-furan-2-yl}-8-oxo-2,4,5,7,8,9-hexahydro-pyrrolo[3,4-b]-1,7-naphthyridine-3-carboxylic acid ethyl ester as an orange solid. Yield=66%. Analytical LC/MS (method B): retention time=5.03 min., m/z=706.9 (positive ion mode).

Boc-Protected Intermediate Preparation:

6-tert-Butyloxy-9-{5-[5-(tert-butyl-dimethyl-silanyloxy)-1H-benzimidazol-2-ylsulfanyl]-furan-2-yl}-8-oxo-2,4,5,7,8,9-hexahydro-pyrrolo[3,4-b]-1,7-naphthyridine-3-carboxylic acid ethyl ester (0.5 g, 0.71 mmol) is treated with tetra-N-butylammonium fluoride (0.185 g, 0.71 mmol) in tetrahydrofuran (5 ml) for 4 hours at room temperature. The reaction mixture is concentrated under reduced pressure and the residue is purified on a silica gel column (40 g) eluted with a mixture of dichloromethane and methanol (9/1, v/v). The fractions containing the expected product are concentrated under reduced pressure and the solid obtained is washed with actonitrile (30 ml), pentane (30 ml) and dried under vacuum to yield 270 mg of 6-tert-butyloxy-9-[5-(5-Hydroxy-1H-benzimidazol-2-ylsulfanyl)-furan-2-yl]-8-oxo-2,4,5,7,8,9-hexahydro-pyrrolo[3,4-b]-1,7-naphthyridine-3-carboxylic acid ethyl ester. Yield=64%. Analytical LC/MS (method B): retention time=3.34 min., m/z=592.31 (positive ion mode).

A solution of 6-tert-butyloxy-9-[5-(5-hydroxy-1H-benzimidazol-2-ylsulfanyl)-furan-2-yl]-8-oxo-2,4,5,7,8,9-hexahydro-pyrrolo[3,4-b]-1,7-naphthyridine-3-carboxylic acid ethyl ester (0.27 g, 0.46 mmol) in dioxane (20 ml) is combined with 4N HCl in dioxane (1.7 ml). The reaction mixture is stirred at room temperature for 16 hours. The formed insoluble material is collected by filtration, washed with dioxane (50 ml), pentane (20 ml), diisopropylether (20 ml) and dried under vacuum to yield 176 mg of 9-[5-(5-hydroxy-1H-benzimidazol-2-ylsulfanyl)-furan-2-yl]-8-oxo-4,5,6,7,8,9-hexahydro-2H-pyrrolo[3,4-b]-1,7-naphthyridine-3-carboxylic acid ethyl ester hydrochloride as a white powder. Yield=73%. Analytical L/MS (method C): m/z=490 (negative ion mode [M−H]⁻), m/z=492 (positive ion mode [M+H]⁺).

500 Mz 1H NMR on a BRUKER AVANCE DRX-500 spectrometer, chemical shifts (δ in ppm) in d6 dimethylsufoxyde (DMSO-d6) solvent referenced at 2.50 ppm at 303K temperature: 1.28 (t, J=7.0 Hz, 3H); 3.72 (d broad, J=16.0 Hz, 1H); 3.82 (d broad, J=16.0 Hz, 1H); 4.22 (m, 1H); 4.27 (m, 2H); 4.45 (d broad, J=16.0 Hz, 1H); 5.20 (s, 1H); 6.37 (d, J=3.5 Hz, 1H); 6.77 (d broad, J=9.0 Hz, 1H); 6.88 (m, 2H); 6.92 (d, J=3.5 Hz, 1H); 7.38 (d, J=9.0 Hz, 1H); 9.40 (s, 1H); 9.56 (m broad, 1H); 9.90 (s broad, 1H); 10.2 (m broad, 1H); 11.7 (s broad, 1H).

EXAMPLE 124

9-[5-(1H-Benzimidazol-2-ylsulfanyl)-furan-2-yl]-6,6-dimethyl-8-oxo-4,5,6,7,8,9-hexahydro-2H-pyrrolo[3,4-b]quinoline-3-carboxylic acid

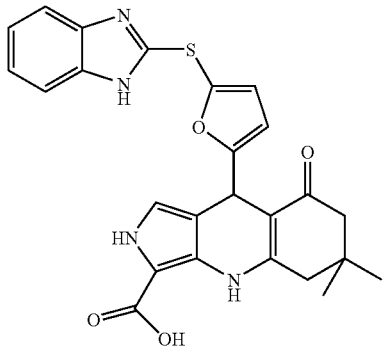

To a solution of 330 mg (0.657 mmol) of 9-[5-(1H-benzimidazol-2-ylsulfanyl)-furan-2-yl]-6,6-dimethyl-8-oxo-4,5,6,7,8,9-hexahydro-2H-pyrrolo[3,4-b]quinoline-3-carboxylic acid ethyl ester in 10 ml ethanol and 1 ml water was added 263 mg of sodium hydroxide in a round bottom flask. The reaction mixture was heated at 40° C. with stirring for 8 hours, and at 30° C. overnight. Water was added to the reaction mixture and it was extracted twice with ethyl acetate. The organic layers were washed with water and brine and dried over magnesium sulfate, filtered and concentrated under reduced pressure. The resulting oily residue was dissolved in 1 ml methanol and 14 ml of dichloromethane and purified by chromatography on a prepacked 75 g 15-40 µm silica gel cartridge (eluting solvent: dichloromethane/methanol from 98/2 to 92/8 v/v in 50 min; rate: 40 mL/min). The fractions containing the desired product were combined and concentrated to dryness under reduced pressure giving 106 mg of 9-[5-(1H-benzimidazol-2-ylsulfanyl)-furan-2-yl]-6,6-dimethyl-8-oxo-4,5,6,7,8,9-hexahydro-2H-pyrrolo[3,4-b]quinoline-3-carboxylic acid (34% yield). Analytical LC/MS method B: [M+H]+=475.5; retention time: 3.01 min; 95% UV purity. 300 MHz $^1$H NMR (DMSO-d$_6$) δ (ppm): 0.91 (s, 3H); 0.98 (s, 3H); 2.05 (d, J=17.0 Hz, 1H); 2.16 (d, J=17.0 Hz, 1H); 2.50 (d partially masked, J=17.0 Hz, 1H); 2.61 (d, J=17.0 Hz, 1H); 5.14 (s, 1H); 5.97 (d, J=3.5 Hz, 1H); 6.73 (d, J=3.0 Hz, 1H); 6.83 (d, J=3.5 Hz, 1H); de 7.10 à 7.20 (m, 2H); 7.40 (d large, J=8.0 Hz, 1H); 7.52 (d large, J=8.0 Hz, 1H); 8.32 (s large, 1H); 11.3 (s large, 1H); 12.25 (m wide, 1H); 12.3 (s large, 1H).

EXAMPLE 125

9-[5-(1H-Benzimidazol-2-ylsulfanyl)-furan-2-yl]-6,6-dimethyl-8-oxo-4,5,6,7,8,9-hexahydro-2H-pyrrolo[3,4-b]quinoline-3-carboxamide

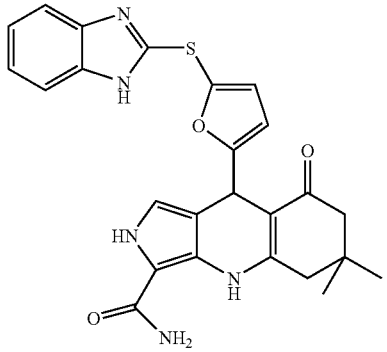

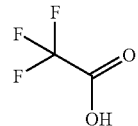

To a solution of 60 mg (0.126 mmol) of 9-[5-(1H-benzimidazol-2-ylsulfanyl)-furan-2-yl]-6.6 dimethyl-8-oxo-4,5,6,7,8,9-hexahydro-2H-pyrrolo[3,4-b]quinoline-3-carboxylic acid in 2 ml dimethylformamide was added successively 72 mg (0.189 mmol) of HBTU, 14 mg (0.253 mmol) of ammonium chloride, 74 mg (0.574 mmol) of N,N-diisopropylethylamine in a round bottom flask. The reaction mixture was stirred overnight at room temperature. Water was then added and the reaction mixture was extracted with ethyl acetate. The organic layer was washed with brine, dried on magnesium sulfate, filtered and concentrated to dryness under reduced pressure. The residue was purified by preparative LCMS (method C) giving 8.9 mg of 9-[5-(1H-benzimidazol-2-ylsulfanyl)-furan-2-yl]-6,6-dimethyl-8-oxo-4,5,6,7,8,9-hexahydro-2H-pyrrolo[3,4-b]quinoline-3-carboxamide (12% yield). Analytical LC/MS method B: [M+H]+=474.5; retention time: 2.90 min; 70% UV (DAD) purity.

EXAMPLE 126

9-[5-(5-Difluoromethoxy-1H-benzimidazol-2-ylsulfanyl)-furan-2-yl]-8-oxo-4,5,6,7,8,9-hexahydro-2H-pyrrolo[3,4-b]quinoline-3-carboxylic acid ethyl ester

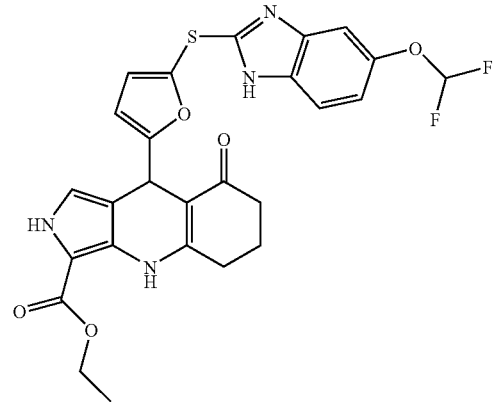

Aldehyde intermediate preparation: a solution 1.5 g of 5-(difluoromethoxy)-2-1H-benzimidazole (6.94 mmol) in 20 ml of anhydrous tetrahydrofuran is added over a 15 minute period to a mixture of 0.294 g of sodium hydride (60% dispersion in mineral oil, 7.35 mmol) and anhydrous tetrahydrofuran at 10° C. The reaction mixture is stirred at room temperature for 2 hours and then a solution of 0.979 g of 5-nitro-2-furaldehyde in 20 ml of anhydrous tetrahydrofuran is added dropwise over a 15 minutes period. The reaction mixture is stirred for 16 hours at room temperature and then poured into 300 ml of water. The mixture is extracted twice with 150 ml of ethyl acetate. The combined organic extracts are dried over MgSO$_4$ and concentrated under reduced pressure. The residue is then triturated with isopropylether and dried under vacuum. 1.9 g of 5-(6-difluoromethoxy-1H-benzimidazol-2-ylsulfanyl)-furan-2-carbaldehyde are isolated as a beige powder. Yield=89%. Analytical LC/MS (method B): retention time=3.38 min., m/z=310.99 (positive ion mode).

A mixture of 3-amino-2-ethoxycarbonyl-pyrrole (0.248 g, 1.61 mmol), 5-(6-difluoromethoxy-1H-benzimidazol-2-yl-sulfanyl)-furan-2-carbaldehyde (0.5 g, 1.61 mmol) and 1,3-cyclohexanedione (0.181 g 1.61 mmol) in 5 ml of ethanol is heated at reflux temperature for 2 hours. The reaction mixture is then concentrated under reduced pressure and dissolved in 5 ml of ethyl acetate. The organic phase is washed twice with 2 ml of water, dried over MgSO$_4$ and concentrated under reduced pressure. The residue is purified on a silica gel column (120 g) eluted with a mixture of dichloromethane and methanol (99/1, v/v). The fractions containing the expected products are pooled and concentrated under reduced pressure. The residue is resuspended in 20 ml of acetonitrile, the mixture is heated at reflux temperature for 15 minutes and then let to cool to room temperature. The insoluble material is collected by filtration and dried under vacuum for 1 hour at 30° C. to yield 203 mg of 9-[5-(5-difluoromethoxy-1H-benzimidazol-2-ylsulfanyl)-furan-2-yl]-8-oxo-4,5,6,7,8,9-hexahydro-2H-pyrrolo[3,4-b]quinoline-3-carboxylic acid ethyl ester as a white powder. Yield=23%. Analytical LC/MS method B: m/z=541 (positive ion mode [M+H]$^+$), m/z=539 (negative ion mode [M−H]$^−$)

400 MHz 1H NMR on a BRUKER AVANCE DRX-400 spectrometer, chemical shifts (δ in ppm) in d6 dimethylsu-foxyde (DMSO-d6) solvent referenced at 2.50 ppm at 303K temperature: 1.28 (t, J=7.0 Hz, 3H); 1.89 (m, 2H); 2.26 (m, 2H); 2.59 (m, 1H); 2.79 (m, 1H); 4.25 (q, J=7.0 Hz, 2H); 5.14 (s, 1H); 5.96 (d, J=3.5 Hz, 1H); 6.79 (d, J=3.5 Hz, 1H); 6,81 (d, J=3.5 Hz, 1H); 6.97 (d broad, J=8.5 Hz, 1H); 7.15 (t, J=74.5 Hz, 1H); 7.25 (s broad 1H); 7.47 (d broad, J=8.5 Hz, 1H); 8.42 (s, 1H); 11.4 (s broad, 1H); 12.55 (m broad, 1H).

EXAMPLE 127

6-tert-Butyloxy-9-[5-(5-Difluoromethoxy-1H-benz-imidazol-2-ylsulfanyl)-furan-2-yl]-8-oxo-2,4,5,7,8,9-hexahydro-pyrrolo[3,4-b]-1,7-naphthyridine-3-carboxylic acid ethyl ester

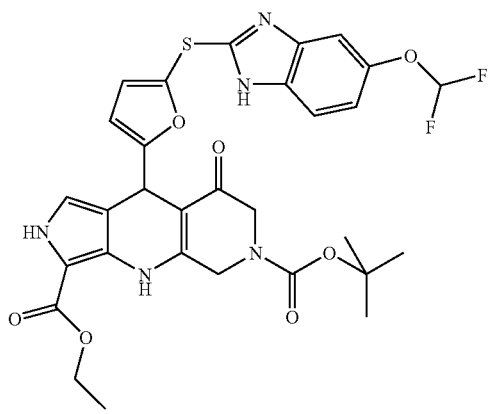

A mixture of 3-amino-2-ethoxycarbonyl-pyrrole (0.497 g, 3.22 mmol), 5-(6-difluoromethoxy-1H-benzimidazol-2-yl-sulfanyl)-furan-2-carbaldehyde (1 g, 3.22 mmol, described in example 126) and N-Boc-3,5-diketopiperidine (0.687 g, 3.22 mmol) in 10 ml of ethanol is heated at reflux temperature for 2 hours. The reaction mixture is then concentrated under reduced pressure and purified on a silica gel column (120 g) eluted with a mixture of dichloromethane and methanol (99/1, v/v). The fractions containing the expected product are pooled and repurified successively by LC/MS method B on a C18 Sunfire column (30*100 mm, 5 µm, Waters) eluted with a gradient from 20 to 95% of acetonitrile containing 0.07% trifluoroacetic acid (v/v) in water containing 0.07% trifluoroacetic acid at a 30 ml/min. flow rate and then on a silica gel column (40 g) eluted with a mixture of dichloromethane and methanol (95/5 v/v) to obtain 250 mg of 6-tert-butyloxy-9-[5-(5-difluoromethoxy-1H-benzimidazol-2-ylsulfanyl)-furan-2-yl]-8-oxo-2,4,5,7,8,9-hexahydro-pyrrolo[3,4-b]-1,7-naphthyridine-3-carboxylic acid ethyl ester as an orange powder. Yield=12%. Analytical LC/MS (method B): retention time=4.20 min., m/z=642.0 (positive ion mode).

400 MHz 1H NMR on a BRUKER AVANCE DRX-400 spectrometer, chemical shifts (δ in ppm) in d6 dimethylsu-foxyde (DMSO-d6) solvent referenced at 2.50 ppm at 303K temperature: 1.29 (t, J=7.0 Hz, 3H); 1.41 (m broad, 9H); de 3.47 à 4.23 (m broad partially masked, 2H); 4.13 (d broad, J=17.5 Hz, 1H); 4.27 (q, J=7.0 Hz, 2H); 4.96 (d, J=17.5 Hz, 1H); 5.20 (s, 1H); 5.93 (d, J=3.5 Hz, 1H); 6.81 (d, J=3.5 Hz, 1H); 6.86 (d, J=3.5 Hz, 1H); 6.99 (dd, J=2.5 et 8.5 Hz, 1H); 7.16 (t, J=74.5 Hz, 1H); 7.27 (d, J=2.5 Hz, 1H); 7.48 (d, J=8.5 Hz, 1H); 9.20 (m broad, 1H); 11.5 (s broad, 1H).

EXAMPLE 128

9-[5-(5-Difluoromethoxy-1H-benzimidazol-2-ylsul-fanyl)-furan-2-yl]-8-oxo-4,5,6,7,8,9-hexahydro-2H-pyrrolo[3,4-b]-1,7-naphthyridine-3-carboxylic acid ethyl ester hydrochloride

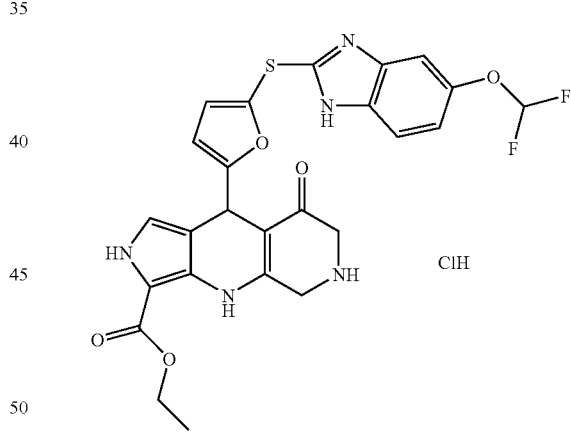

230 mg of 6-tert-butyloxy-9-[5-(5-difluoromethoxy-1H-benzimidazol-2-ylsulfanyl)-furan-2-yl]-8-oxo-2,4,5,7,8,9-hexahydro-pyrrolo[3,4-b]-1,7-naphthyridine-3-carboxylic acid ethyl ester (example 127) are dissolved in 1.4 ml of dioxane and combined with 1.434 ml of 4N HCl in dioxane. The reaction mixture is stirred for 16 hours at room temperature. The formed insoluble material is then collected by filtration, washed successively with 2×2 ml of dioxane and 2×2 ml of diisopropylether, and dried under vacuum to yield 107 mg of 9-[5-(5-difluoromethoxy-1H-benzimidazol-2-ylsulfa-nyl)-furan-2-yl]-8-oxo-4,5,6,7,8,9-hexahydro-2H-pyrrolo[3,4-b]-1,7-naphthyridine-3-carboxylic acid ethyl ester hydrochloride as a brown powder. Yield=55%. Analytical LC/MS (method B): retention time=2.90 min., m/z=541.96 (positive ion mode).

400 MHz 1H NMR on a BRUKER AVANCE DRX-400 spectrometer, chemical shifts (δ in ppm) in d6 dimethylsufoxyde (DMSO-d6) solvent referenced at 2.50 ppm at 303K temperature: 1.29 (t, J=7.0 Hz, 3H); 3.79 (m, 2H); 4.22 (m, 1H); 4.28 (q, J=7.0 Hz, 2H); 4.44 (d broad, J=16.5 Hz, 1H); 5.22 (s, 1H); 6.27 (d, J=3.5 Hz, 1H); 6.86 (d, J=3.5 Hz, 1H); 6.89 (d, J=3.5 Hz, 1H); 7.01 (d broad, J=8.5 Hz, 1H); 7.16 (t, J=74.5 Hz, 1H); 7.29 (m broad, 1H); 7.50 (m broad, 1H); 9.39 (s, 1H); 9.63 (m broad, 1H); 9.73 (m broad, 1H); 11.65 (s broad, 1H); 12.65 (m broad, 1H).

EXAMPLE 129

9-[5-(5-Chloro-1H-benzimidazol-2-ylsulfanyl)-furan-2-yl]-8-oxo-4,5,6,7,8,9-hexahydro-2H-pyrrolo[3,4-b]quinoline-3-carboxylic acid ethyl ester

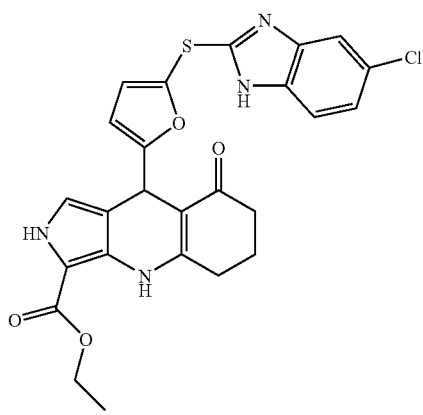

Aldehyde intermediate preparation: 5-Chloro-2-mercaptobenzimidazole (1.5 g, 8.12 mmol) dissolved in 10 ml of anhydrous tetrahydrofuran is added dropwise to a suspension of sodium hydride (60% dispersion in mineral oil, 0.325 g, 8.12 mmol) in anhydrous tetrahydrofuran (20 ml) at 10° C. over a 15 minute period. The reaction mixture is stirred for 2 hours at room temperature. Then 5-nitro-2-furaldehyde (1.146 g, 8.12 mmol) dissolved in 20 ml of anhydrous tetrahydrofuran is added dropwise over a 15 minute period and the reaction mixture is stirred at room temperature for an additional 16 hour period. The reaction mixture is then poured into 300 ml of water and extracted twice with 150 ml of ethyl acetate. The combined organic extracts are dried over MgSO$_4$ and concentrated under reduced pressure. The residue is purified on a silica gel column (120 g) eluted with a mixture of cyclohexane and ethyl acetate (80/20, v/v) to yield 1.9 g of 5-(6-chloro-1H-benzimidazol-2-ylsulfanyl)-furan-2-carbaldehyde. Yield=88%. Analytical LC/MS (method B): retention time=3.40 min., m/z=278.95/1Cl (positive ion mode).

A mixture of 3-amino-2-ethoxycarbonyl-pyrrole (0.276 g 1.79 mmol), 5-(6-chloro-1H-benzimidazol-2-ylsulfanyl)-furan-2-carbaldehyde (0.5 g, 1.79 mmol) and 1,3-cyclohexanedione (0.201 g, 1.79 mmol) in 5 ml of ethanol is heated at reflux temperature for 2 hours. The reaction mixture is then concentrated under reduced pressure and purified on a silica gel column (120 g) eluted with a mixture of dichloromethane and methanol (99/1, v/v). The fractions containing the expected products are concentrated under reduced pressure and then purified using preparative LC/MS method B on a Xbridge C18 column (Waters, 30*100 mm) eluted with a 0 to 50% gradient of acetonitrile in aqueous 10 mM ammonium formate pH=9.0 at a 30 ml/min. flow rate in 12 min. The fraction containing the expected product are concentrated under reduced pressure. The residue is resuspended in 2 ml of acetonitrile, heated at reflux temperature and cold to room temperature. The insoluble material is collected by filtration, washed with diisopropyl ether (2×2 ml) and dried under vacuum to yield 115 mg of 9-[5-(5-chloro-1H-benzimidazol-2-ylsulfanyl)-furan-2-yl]-8-oxo-4,5,6,7,8,9-hexahydro-2H-pyrrolo[3,4-b]quinoline-3-carboxylic acid ethyl ester as a white powder. Yield=12%. Analytical LC/MS (method B): m/z=509 (positive ion mode, [M+H]$^+$, 1 Cl present), m/z=507 (negative ion mode, [M−H]$^-$, 1 Cl present)

400 MHz 1H NMR on a BRUKER AVANCE DRX-400 spectrometer, chemical shifts (δ in ppm) in d6 dimethylsufoxyde (DMSO-d6) solvent referenced at 2.50 ppm at 303K temperature: 1.28 (t, J=7.0 Hz, 3H); 1.89 (m, 2H); 2.25 (m, 2H); 2.58 (m, 1H); 2.79 (m, 1H); 4.26 (q, J=7.0 Hz, 2H); 5.15 (s, 1H); 5.98 (d, J=3.5 Hz, 1H); 6.79 (s, 1H); 6.83 (d, J=3.5 Hz, 1H); 7.16 (dd, J=2.5 et 8.5 Hz, 1H); 7.46 (d, J=8.5 Hz, 1H); 7.52 (s broad, 1H); 8.43 (s, 1H); 11.0 (m broad, 1H); 11.4 (s broad, 1H).

EXAMPLE 130

6-tert-Butyloxy-9-[5-(5-chloro-1H-benzimidazol-2-ylsulfanyl)-furan-2-yl]-8-oxo-2,4,5,7,8,9-hexahydropyrrolo[3,4-b]-1,7-naphthyridine-3-carboxylic acid ethyl ester

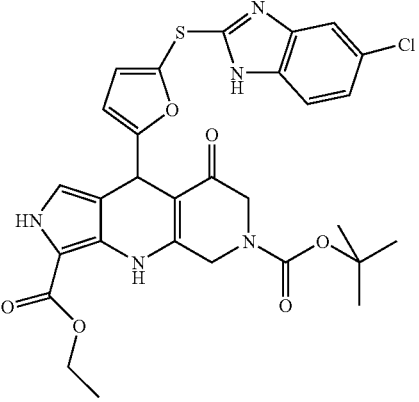

A mixture of 3-amino-2-ethoxycarbonyl-pyrrole (0.553 g 3.59 mmol), 5-(6-chloro-1H-benzimidazol-2-ylsulfanyl)-furan-2-carbaldehyde (1 g, 3.59 mmol, described in example 129) and N-Boc-3,5-diketopiperidine (0.75 g, 3.59 mmol) in 10 ml ethanol is heated at reflux temperature for 2 hours. The reaction mixture is then concentrated under reduced pressure and purified on a silica gel column (120 g) eluted with a mixture of dichloromethane and methanol (99/1, v/v). The fractions containing the expected products are concentrated under reduced pressure and then purified using preparative LC/MS method B on a Sunfire C18 column (Waters, 30*100 mm) eluted with a 20 to 95% gradient of acetonitrile containing 0.07% trifluoroacetic acid in water containing 0.07% trifluoroacetic acid at a flow rate of 30 ml/min in 12 minutes. The fraction containing the expected product are concentrated under reduced pressure to deliver 230 mg of 6-tert-butyloxy-9-[5-(5-chloro-1H-benzimidazol-2-ylsulfanyl)-furan-2-yl]-8-oxo-2,4,5,7,8,9-hexahydro-pyrrolo[3,4-b]-1,7- naphthyridine-3-carboxylic acid ethyl ester as a light-orange powder. Yield=11%. LC/MS (method B): m/z=608 (negative ion mode, [M−H]⁻, 1 Cl), m/z=610 (positive ion mode, [M+H]⁺, 1 Cl)

400 MHz 1H NMR on a BRUKER AVANCE DRX-400 spectrometer, chemical shifts (δ in ppm) in d6 dimethylsufoxyde (DMSO-d6) solvent referenced at 2.50 ppm at 303K temperature: 1.28 (t, J=7.0 Hz, 3H); 1.41 (m broad, 9H); de 3.21 à 4.23 (m broad partially masked, 2H); 4.13 (d broad, J=17.5 Hz, 1H); 4.28 (q, J=7.0 Hz, 2H); 4.96 (d, J=17.5 Hz, 1H); 5.20 (s, 1H); 5.95 (d, J=3.5 Hz, 1H); 6.81 (d, J=3.5 Hz, 1H); 6.87 (d, J=3.5 Hz, 1H); 7.17 (dd, J=2.0 et 8.5 Hz, 1H); 7.47 (d, J=8.5 Hz, 1H); 7.52 (d, J=2.0 Hz, 1H); 9.18 (m broad, 1H); 11.5 (s broad, 1H).

EXAMPLE 131

9-[5-(5-Chloro-1H-benzimidazol-2-ylsulfanyl)-furan-2-yl]-8-oxo-4,5,6,7,8,9-hexahydro-2H-pyrrolo[3,4-b]-1,7-naphthyridine-3-carboxylic acid ethyl ester hydrochloride

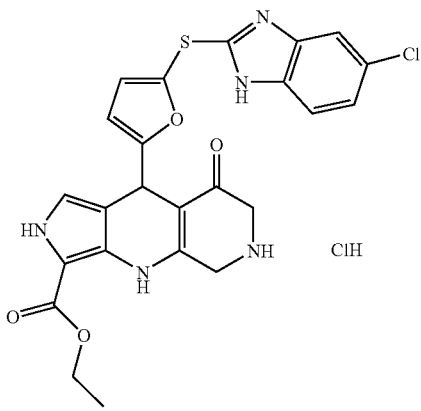

210 mg of 6-tert-butyloxy-9-[5-(5-chloro-1H-benzimidazol-2-ylsulfanyl)-furan-2-yl]-8-oxo-2,4,5,7,8,9-hexahydropyrrolo[3,4-b]-1,7-naphthyridine-3-carboxylic acid ethyl ester (example 130) are dissolved in 1.4 ml of dioxane and combined with 1.415 ml of 4N HCl in dioxane. The reaction mixture is stirred for 16 hours at room temparature. The formed insoluble material is then collected by filtration, washed with 2×1 ml of dioxane and 2×1 ml of diisopropylether. The residue is then purified on a silica gel column (12 g) eluted with a mixture of dichloromethane and methanol (95/5, v/v). The fraction containing the expected product are concentrated under reduced pressure to yield 135 mg of 9-[5-(5-chloro-1H-benzimidazol-2-ylsulfanyl)-furan-2-yl]-8-oxo-4,5,6,7,8,9-hexahydro-2H-pyrrolo[3,4-b]-1,7-naphthyridine-3-carboxylic acid ethyl ester hydrochloride as an orange powder. Yield=77%. Analytical LC/MS (method B): m/z=508 (negative ion mode, [M−H]⁻, 1 Cl present), m/z=510 (positive ion mode, [M+H]⁺)

400 MHz 1H NMR on a BRUKER AVANCE DRX-400 spectrometer, chemical shifts (δ in ppm) in d6 dimethylsufoxyde (DMSO-d6) solvent referenced at 2.50 ppm at 303K temperature: 1.29 (t, J=7.0 Hz, 3H); de 3.67 à 3.86 (m, 2H); 4.22 (m, 1H); 4.28 (q, J=7.0 Hz, 2H); 4.45 (d, J=16.5 Hz, 1H); 5.20 (s, 1H); 6.39 (d, J=3.5 Hz, 1H); 6.86 (d, J=3.5 Hz, 1H); 6.89 (d, J=3.5 Hz, 1H); 7.19 (d broad, J=8.5 Hz, 1H); 7.49 (d, J=8.5 Hz, 1H); 7.56 (s broad, 1H); 9.36 (s, 1H); 10.05 (m broad, 1H); 10.35 (m broad, 1H); 11.65 (s broad, 1H).

EXAMPLE 132

8-Oxo-9-[5-(5-trifluoromethyl-1H-benzimidazol-2-ylsulfanyl)-furan-2-yl]-4,5,6,7,8,9-hexahydro-2H-pyrrolo[3,4-b]quinoline-3-carboxylic acid ethyl ester

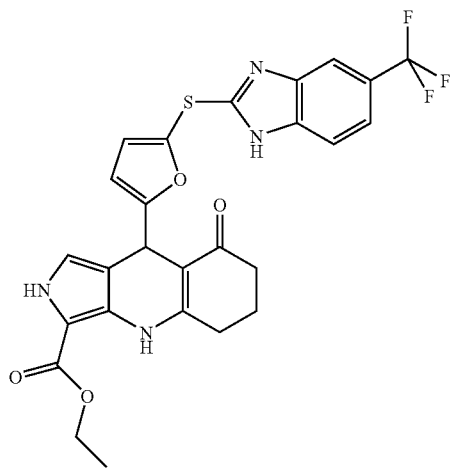

2-Mercaptobenzimidazole Intermediate Preparation:

4-trifluoromethyl-benzene-1,2-diamine (0.5 g, 2.84 mmol) and 1,1'-thiocarbonyldiimidazole (0.84 g, 4.73 mmol) in 5 ml of tetrahydrofuran are stirred at room temperature for 48 hours. The reaction mixture is concentrated under reduced pressure and the residue is dissolved in 10 ml ethyl acetate and washed with water (2×3 ml). The organic phase is dried over MgSO₄ and concentrated under reduced pressure. The residue is then purified on a silica gel column (32 g) eluted with dichloromethane. The fractions containing the expected product are concentrated under reduced pressure to yield 400 mg of 2-mercapto-6-trifluoromethyl-1H-benzimidazole. Yield=65%. Analytical LC/MS (method B): retention time=3.14 min., m/z=218.98 (positive ion mode).

Aldehyde intermediate preparation: 2-mercapto-6-trifluoromethyl-1H-benzimidazole (0.65 g, 2.98 mmol) dissolved in 5 ml of anhydrous tetrahydrofuran is added dropwise to a suspension of sodium hydride (60% dispersion in mineral oil, 0.095 g, 3.16 mmol) in anhydrous tetrahydrofuran (2 ml) over a 20 minutes period. The reaction mixture is stirred for 2 hours at room temperature. Then 5-nitro-2-furaldehyde (0.42 g, 2.98 mmol) dissolved in 5 ml of anhydrous tetrahydrofuran is added dropwise over a 15 minutes period and the reaction mixture is stirred at room temperature for an additional 16 hours period. Sodium hydride (67 mg, 2.23 mmol) is then added and the reaction mixture is stirred for an additional 2 hours period at room temperature. The reaction mixture is then concentrated under reduced pressure, dissolved in ethyl acetate (50 ml) and washed with water (2×10 ml). The organic phase is dried over MgSO₄, concentrated under reduced pressure and the residue is triturated in diisopropylether, collected by filtration and dried under vacuum to yield 720 mg of 5-(6-trifluoromethyl-1H-benzimidazol-2-ylsulfanyl)-furan-2-carbaldehyde as a beige powder. Yield=77%, Analytical LC/MS (method B): retention time=3.73 min., m/z=313.01 (positive ion mode).

A mixture of 3-amino-2-ethoxycarbonyl-pyrrole (0.355 g 2.31 mmol), 5-(6-trifluoromethyl-1H-benzimidazol-2-ylsulfanyl)-furan-2-carbaldehyde (0.72 g, 2.31 mmol) and 1,3-cyclohexanedione (0.259 g, 2.31 mmol) in 5 ml ethanol is heated at reflux temperature for 1 hour. The formed insoluble material is filtered off, the filtrate is concentrated under reduced pressure and purified on a silica gel column (120 g) eluted with a mixture of cyclohexane and ethylacetate (7/3, v/v). The fractions containing the expected product are concentrated under reduced pressure and purified via preparative LC/MS method B on a XBridge C18 column (Waters, 30*100 mm) eluted with a 0 to 50% in 12 min. gradient of acetonitrile in 10 mM aqueous ammonium formate pH=9.0 at a 30 ml/min. flow rate to deliver 56 mg of 8-oxo-9-[5-(5-trifluoromethyl-1H-benzimidazol-2-ylsulfanyl)-furan-2-yl]-4,5,6,7,8,9-hexahydro-2H-pyrrolo[3,4-b]quinoline-3-carboxylic acid ethyl ester. Yield=4%.

400 MHz 1H NMR on a BRUKER AVANCE DRX-400 spectrometer, chemical shifts (δ in ppm) in d6 dimethylsufoxyde (DMSO-d6) solvent referenced at 2.50 ppm at 303K temperature: 1.28 (t, J=7.0 Hz, 3H); 1.89 (m, 2H); 2.24 (m, 2H); 2.57 (m, 1H); 2.79 (m, 1H); 4.25 (q, J=7.0 Hz, 2H); 5.16 (s, 1H); 6.00 (d, J=3.5 Hz, 1H); 6.79 (d, J=3.5 Hz, 1H); 6.86 (d, J=3.5 Hz, 1H); 7.45 (d broad, J=8.5 Hz, 1H); 7.64 (d broad, J=8.5 Hz, 1H); 7.81 (s broad, 1H); 8.43 (s, 1H); 11.4 (s broad, 1H); 12.8 (m broad, 1H).

EXAMPLE 133

9-[5-(5-Chloro-6-methyl-1H-benzimidazol-2-ylsulfanyl)-furan-2-yl]-8-oxo-4,5,6,7,8,9-hexahydro-2H-pyrrolo[3,4-b]quinoline-3-carboxylic acid ethyl ester

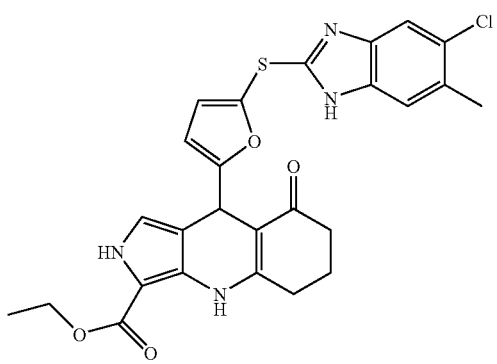

2-Mercaptobenzimidazole Intermediate Preparation:

A mixture of 4-chloro-5-methylbenzene-1,2-diamine (1 g, 6.38 mmol) and di-2-pyridylthionocarbonate (2.46 g, 10.6 mmol) in 5 ml of tetrahydrofuran is stirred at room temperature for 72 hours. The reaction mixture is diluted with 100 ml of ethyl acetate and washed with 2×30 ml of water. The organic phase is dried over MgSO$_4$, filtered and concentrated under reduced pressure. The residue is triturated in diisopropylether and pentane and finally dried under vacuum to yield 1.05 g of 2-mercapto-5-chloro-6-methyl-1H-benzimidazole as a yellow powder. Yield=83%. Analytical LC/MS (method B): retention time=3.10 min., m/z=198.97 (positive ion mode).

Aldehyde intermediate preparation: A mixture of sodium hydride (60% dispersion in mineral oil, 0.338 g, 8.46 mmol) and 2-mercapto-5-chloro-6-methyl-1H-benzimidazole (1.05 g, 5.29 mmol) in 35 ml of tetrahydrofuran is stirred at room temperature for 2 hours. 5-nitro-2-furaldehyde (0.746 g, 5.29 mmol) in 7 ml of tetrahydrofuran is then added dropwise over a 15 minute period and the mixture is stirred for 16 hours at room temperature. The reaction mixture is then concentrated under reduced pressure and dissolved in 100 ml ethyl acetate and washed with water (2×30 ml). The organic phase is dried over MgSO$_4$ and concentrated under reduced pressure. The residue is triturated in diisopropylether and pentane and dried under vacuum to yield 854 mg of 5-(5-chloro-6-methyl-1H-benzimidazol-2-ylsulfanyl)-furan-2-carbaldehyde.
Yield=55%. Analytical LC/MS (method B): retention time=3.64 min, m/z=272.97 (1Cl, positive ion mode).

A mixture of 3-amino-2-ethoxycarbonyl-pyrrole (0.204 g, 1.32 mmol), 5-(5-chloro-6-methyl-1H-benzimidazol-2-ylsulfanyl)-furan-2-carbaldehyde (0.388 g, 1.32 mmol) and 1,3-cyclohexanedione (0.149 g, 1.32 mmol) in 10 ml of 1-butanol is heated at reflux temperature for 4 h. The reaction mixture is then concentrated under reduced pressure and purified on a silica gel column (34 g) eluted with a mixture of cyclohexane and ethylacetate (7/3, v/v). The fractions containing the expected product are concentrated under reduced pressure, and the residue is resuspended in 5 ml of acetonitrile and heated at reflux temperature for 15 minutes. After cooling to room temperature, the insoluble material is collected by filtration and dried under vacuum to yield 76 mg of 9-[5-(5-chloro-6-methyl-1H-benzimidazol-2-ylsulfanyl)-furan-2-yl]-8-oxo-4,5,6,7,8,9-hexahydro-2H-pyrrolo[3,4-b]quinoline-3-carboxylic acid ethyl ester. Yield=11%. Analytical LC/MS (method B): m/z=523 (positive ion mode, [M+H]$^+$, 1 Cl present), m/z=521 (negative ion mode, [M−H]$^−$, 1 Cl present).

400 MHz 1H NMR on a BRUKER AVANCE DRX-400 spectrometer, chemical shifts (δ in ppm) in d6 dimethylsufoxyde (DMSO-d6) solvent referenced at 2.50 ppm at 303K temperature: 1.28 (t, J=7.0 Hz, 3H); 1.89 (m, 2H); 2.26 (m, 2H); 2.39 (s, 3H); 2.58 (m, 1H); 2.79 (m, 1H); 4.26 (q, J=7.0 Hz, 2H); 5.14 (s, 1H); 5.97 (d, J=3.5 Hz, 1H); 6.78 (d, J=3.5 Hz, 1H); 6.82 (d broad, J=3.5 Hz, 1H); 7.42 (s broad, 1H); 7.52 (s broad, 1H); 8.42 (s, 1H); 11.4 (s broad, 1H); 12.5 (m broad, 1H).

EXAMPLE 134

6-tert-Butyloxy-9-[5-(5-chloro-6-methyl-1H-benzimidazol-2-ylsulfanyl)-furan-2-yl]-8-oxo-2,4,5,7,8,9-hexahydro-pyrrolo[3,4-b]-1,7-naphthyridine-3-carboxylic acid ethyl ester

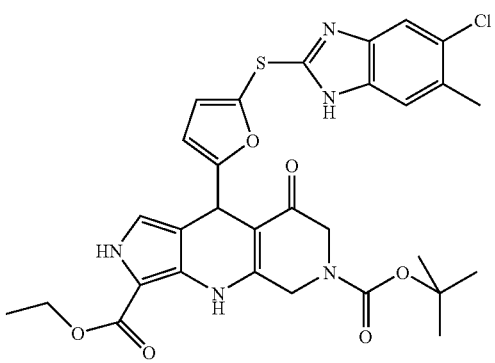

A mixture of 3-amino-2-ethoxycarbonyl-pyrrole (0.21 g, 1.36 mmol), 5-(5-chloro-6-methyl-1H-benzimidazol-2-ylsulfanyl)-furan-2-carbaldehyde (0.400 g, 1.36 mmol, described in example 133) and N-Boc-3,5-diketopiperidine (0.291 g, 1.36 mmol) in 10 ml of 1-butanol is heated at reflux temperature for 4 h. The reaction mixture is then concentrated under reduced pressure and the residue is purified on a silica gel column (34 g) eluted with a mixture of cyclohexane and ethyl acetate (7/3, v/v). The fractions containing the expected product are concentrated under reduced pressure. The solid is then washed with diisopropylether and pentane and dried under vacuum to yield 338 mg of 6-tert-butyloxy-9-[5-(5-chloro-6-methyl-1H-benzimidazol-2-ylsulfanyl)-furan-2-yl]-8-oxo-2,4,5,7,8,9-hexahydro-pyrrolo[3,4-b]-1,7-naphthyridine-3-carboxylic acid ethyl ester. Yield=40%. Analytical LC/MS (method B): m/z=624 (positive ion mode [M+H]+, 1 Cl present), m/z=622 (negative ion mode [M−H]−, 1 Cl present)

400 MHz 1H NMR on a BRUKER AVANCE DRX-400 spectrometer, chemical shifts (δ in ppm) in d6 dimethylsufoxyde (DMSO-d6) solvent referenced at 2.50 ppm at 303K temperature: 1.29 (t, J=7.0 Hz, 3H); 1.41 (s broad, 9H); 2.38 (s, 3H); 3.76 (m broad, 1H); 4.13 (m broad, 2H); 4.27 (q, J=7.0 Hz, 2H); 4.96 (d, J=18.0 Hz, 1H); 5.19 (s, 1H); 5.93 (d, J=3.5 Hz, 1H); 6.81 (d, J=3.5 Hz, 1H); 6.84 (d, J=3.5 Hz, 1H); 7.40 (s broad, 1H); 7.50 (s broad, 1H); 9.19 (m broad, 1H); 11.5 (s broad, 1H); 12.5 (m broad, 1H).

EXAMPLE 135

9-[5-(5-Chloro-6-methyl-1H-benzimidazol-2-ylsulfanyl)-furan-2-yl]-8-oxo-4,5,6,7,8,9-hexahydro-2H-pyrrolo[3,4-b]-1,7-naphthyridine-3-carboxylic acid ethyl ester hydrochloride

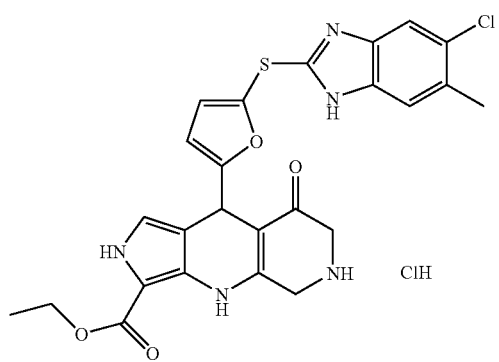

328 mg 6-tert-butyloxy-9-[5-(5-chloro-6-methyl-1H-benzimidazol-2-ylsulfanyl)-furan-2-yl]-8-oxo-2,4,5,7,8,9-hexahydro-pyrrolo[3,4-b]-1,7-naphthyridine-3-carboxylic acid ethyl ester (example 134) are dissolved in 10 ml of dioxane and combined with 2.16 ml of 4N HCl in dioxane. The mixture is stirred for 16 hours at room temperature. The insoluble material is collected by filtration, washed with dioxane (10 ml), diisopropylether (10 ml) and pentane (10 ml) and dried under vacuum to yield 290 mg of 9-[5-(5-chloro-6-methyl-1H-benzimidazol-2-ylsulfanyl)-furan-2-yl]-8-oxo-4,5,6,7,8,9-hexahydro-2H-pyrrolo[3,4-b]-1,7-naphthyridine-3-carboxylic acid ethyl ester hydrochloride. Yield=98%.

Analytical LC/MS: m/z=524 (positive ion mode [M+H]+, 1 Cl present), m/z=522 (negative ion mode [M−H]−, 1 Cl present)

400 MHz 1H NMR on a BRUKER AVANCE DRX-400 spectrometer, chemical shifts (δ in ppm) in d6 dimethylsufoxyde (DMSO-d6) solvent referenced at 2.50 ppm at 303K temperature: 1.29 (t, J=7.0 Hz, 3H); 2.39 (s, 3H); de 3.50 à 3.85 (m partially masked, 2H); 4.22 (m, 1H); 4.28 (q, J=7.0 Hz, 2H); 4.47 (d broad, J=16.5 Hz, 1H); 5.21 (s, 1H); 6.32 (d, J=3.5 Hz, 1H); 6.86 (d, J=3.5 Hz, 1H); 6.89 (d, J=3.5 Hz, 1H); 7.44 (s, 1H); 7.55 (s, 1H); 9.38 (s, 1H); 9.80 (m broad, 1H); 9.98 (m broad, 1H); 11.65 (s broad, 1H).

EXAMPLE 136

9-[5-(5-Chloro-7-methyl-1H-benzimidazol-2-ylsulfanyl)-furan-2-yl]-8-oxo-4,5,6,7,8,9-hexahydro-2H-pyrrolo[3,4-b]quinoline-3-carboxylic acid ethyl ester

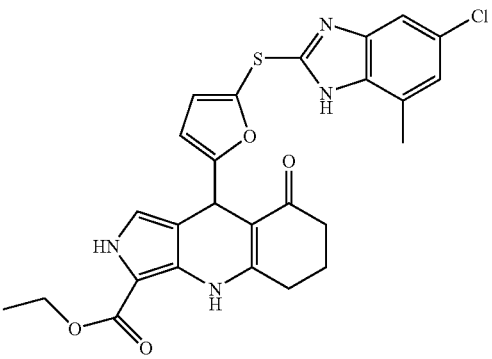

2-Mercaptobenzimidazole Intermediate Preparation:

A mixture of 5-chloro-3-methylbenzene-1,2-diamine (1 g, 6.38 mmol) and di-2-pyridylthionocarbonate (2.37 g, 10.2 mmol) in 10 ml of tetrahydrofuran is stirred at room temperature for 16 hours. The formed insoluble material is then collected by filtration and dried on the filter to yield 945 mg of 2-mercapto-5-chloro-7-methyl-1H-benzimidazole. Yield=75%. Analytical LC/MS (method B): retention time=3.10 min., m/z=198.93 (1 Cl, positive ion mode).

Aldehyde intermediate preparation: A mixture of sodium hydride (60% dispersion in mineral oil, 0.304 g, 7.61 mmol) and 2-mercapto-5-chloro-7-methyl-1H-benzimidazole (0.945 g, 4.76 mmol) in 15 ml of tetrahydrofuran is stirred at room temperature for 2 hours. 5-nitro-2-furaldehyde (0.671 g, 4.56 mmol) in 7 ml of tetrahydrofuran is then added dropwise over a 15 minute period and the mixture is stirred for 16 hours at room temperature. The reaction mixture is then concentrated under reduced pressure and the residue is dissolved in 100 ml of ethyl acetate and washed with water (2×30 ml). The organic phase is dried over MgSO4 and concentrated under reduced pressure. The residue is triturated in diisopropylether and pentane and dried under vacuum to yield 911 mg of 5-(5-chloro-7-methyl-1H-benzimidazol-2-ylsulfanyl)-furan-2-carbaldehyde. Yield=65%. Analytical LC/MS (method B): retention time: 3.67 min., m/z=292.98 (1 Cl, positive ion mode).

A mixture of 3-amino-2-ethoxycarbonyl-pyrrole (0.158 g, 1.02 mmol), 5-(5-chloro-7-methyl-1H-benzimidazol-2-yl-sulfanyl)-furan-2-carbaldehyde (0.30 g, 1.02 mmol) and 1,3-cyclohexanedione (0.115 g, 1.02 mmol) in 5 ml of 1-butanol is heated at reflux temperature for 4 h. The reaction mixture is then concentrated under reduced pressure and the residue is purified on a silica gel column (34 g) eluted with a mixture of cyclohexane and ethylacetate (7/3, v/v). The fractions containing the expected product are concentrated under reduced pressure and the residue is triturated in diisopropylether and pentane. The obtained solid is then resuspended in 5 ml acetonitrile, heated at reflux temperature for 30 minutes and let to cool to room temperature. The insoluble material is collected by filtration and dried under vacuum to deliver 100 mg of 9-[5-(5-chloro-7-methyl-1H-benzimidazol-2-ylsulfanyl)-furan-2-yl]-8-oxo-4,5,6,7,8,9-hexahydro-2H-pyrrolo[3,4-b]quinoline-3-carboxylic acid ethyl ester. Yield=20%. Analytical LC/MS (method B): m/z=523 (positive ion mode [M+H]$^+$, 1 Cl present), m/z=521 (negative ion mode [M−H]$^-$, 1 Cl present).

400 MHz 1H NMR on a BRUKER AVANCE DRX-400 spectrometer, chemical shifts (δ in ppm) in d6 dimethylsu-foxyde (DMSO-d6) solvent referenced at 2.50 ppm at 303K temperature: 1.28 (t, J=7.0 Hz, 3H); 1.89 (m, 2H); 2.25 (m, 2H); 2.44 (s, 3H); 2.59 (m, 1H); 2.79 (m, 1H); 4.25 (q, J=7.0 Hz, 2H); 5.14 (s, 1H); 5.96 (d, J=3.5 Hz, 1H); 6.77 (d, J=3.5 Hz, 1H); 6.79 (d broad, J=2.5 Hz, 1H); 6.99 (s broad, 1H); 7.31 (m broad, 1H); 8.41 (s, 1H); 11.4 (s broad, 1H); 12.6 (m broad, 1H).

EXAMPLE 137

6-tert-Butyloxy-9-[5-(5-chloro-7-methyl-1H-benzimidazol-2-ylsulfanyl)-furan-2-yl]-8-oxo-2,4,5,7,8,9-hexahydro-pyrrolo[3,4-b]-1,7-naphthyridine-3-carboxylic acid ethyl ester

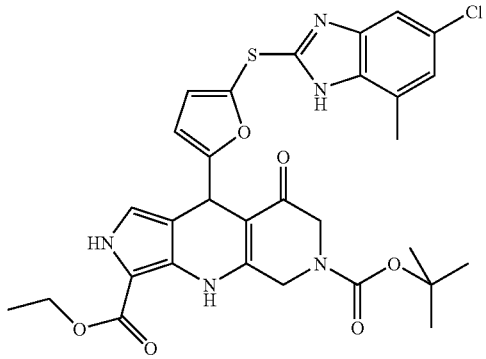

A mixture of 3-amino-2-ethoxycarbonyl-pyrrole (0.211 g, 1.37 mmol), 5-(5-chloro-7-methyl-1H-benzimidazol-2-yl-sulfanyl)-furan-2-carbaldehyde (0.40 g, 1.37 mmol, described in example 136) and N-Boc-3,5-diketopiperidine (0.291 g, 1.37 mmol) in 10 ml of 1-butanol is heated at reflux temperature for 4 h. The reaction mixture is then concentrated under reduced pressure and the residue is purified on a silica gel column (34 g) eluted with a mixture of cyclohexane and ethylacetate (7/3, v/v). The fractions containing the expected product are concentrated under reduced pressure and the residue is triturated in diisopropylether and pentane. 306 mg of 6-tert-butyloxy-9-[5-(5-chloro-7-methyl-1H-benzimidazol-2-ylsulfanyl)-furan-2-yl]-8-oxo-2,4,5,7,8,9-hexahydro-pyrrolo[3,4-b]-1,7-naphthyridine-3-carboxylic acid-ethyl ester are obtained. Yield=36%. Analytical LC/MS (method B): m/z=624 (positive ion mode [M+H]$^+$, 1 Cl present), m/z=622 (negative ion mode [M−H]$^-$, 1 Cl present).

400 MHz 1H NMR on a BRUKER AVANCE DRX-400 spectrometer, chemical shifts (δ in ppm) in d6 dimethylsu-foxyde (DMSO-d6) solvent referenced at 2.50 ppm at 303K temperature: 1.29 (t, J=7.0 Hz, 3H); 1.41 (s broad, 9H); 2.43 (s, 3H); 3.75 (m broad, 1H); 4.14 (m broad, 2H); 4.28 (q, J=7.0 Hz, 2H); 5.96 (d, J=17.5 Hz, 1H); 5.19 (s, 1H); 5.92 (d, J=3.5 Hz, 1H); 6.79 (d, J=3.5 Hz, 1H); 6.82 (d, J=3.5 Hz, 1H); 6.98 (s broad, 1H); 7.30 (m broad, 1H); 9.19 (m broad, 1H); 11.5 (s broad, 1H); 12.6 (m broad, 1H).

EXAMPLE 138

9-[5-(5-Chloro-7-methyl-1H-benzimidazol-2-ylsulfanyl)-furan-2-yl]-8-oxo-4,5,6,7,8,9-hexahydro-2H-pyrrolo[3,4-b]-1,7-naphthyridine-3-carboxylic acid ethyl ester hydrochloride

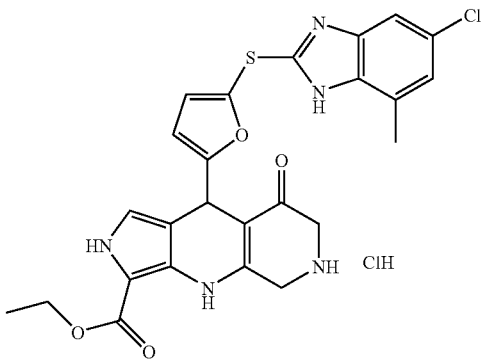

290 mg of 6-tert-butyloxy-9-[5-(5-chloro-7-methyl-1H-benzimidazol-2-ylsulfanyl)-furan-2-yl]-8-oxo-2,4,5,7,8,9-hexahydro-pyrrolo[3,4-b]-1,7-naphthyridine-3-carboxylic acid ethyl ester (example 137) are dissolved in 10 ml of dioxane and combined with 1.912 ml of 4N HCl in dioxane. The reaction mixture is stirred for 16 hours at room temperature. The formed insoluble material is collected by filtration, washed with dioxane (10 ml), diisopropylether (10 ml) and pentane (10 ml) and dried under vacuum to yield 268 mg of 9-[5-(5-chloro-7-methyl-1H-benzimidazol-2-ylsulfanyl)-furan-2-yl]-8-oxo-4,5,6,7,8,9-hexahydro-2H-pyrrolo[3,4-b]-1,7-naphthyridine-3-carboxylic acid ethyl ester hydrochloride. Yield=93%. Analytical LC/MS (method B): m/z=524 (positive ion mode [M+H]$^+$, 1 Cl present), m/z=522 (negative ion mode [M−H]$^-$, 1 Cl present).

400 MHz 1H NMR on a BRUKER AVANCE DRX-400 spectrometer, chemical shifts (δ in ppm) in d6 dimethylsu-foxyde (DMSO-d6) solvent referenced at 2.50 ppm at 303K temperature: 1.29 (t, J=7.0 Hz, 3H); 2.44 (s, 3H); de 3.50 à 3.90 (m partially masked, 2H); 4.23 (m, 1H); 4.28 (q, J=7.0

Hz, 2H); 4.45 (d broad, J=16.5 Hz, 1H); 5.20 (s, 1H); 6.31 (d, J=3.5 Hz, 1H); 6.84 (d, J=3.5 Hz, 1H); 6.87 (d, J=3.5 Hz, 1H); 7.03 (s broad, 1H); 7.35 (s broad, 1H); 9.38 (s, 1H); 9.80 (m broad, 1H); 9.96 (m broad, 1H); 11.65 (s broad, 1H).

EXAMPLE 139

9-[5-(2,2-Difluoro-5H-[1,3]dioxolo[4',5':4,5]benzo[1,2-d]imidazol-6-ylsulfanyl)-furan-2-yl]-8-oxo-4,5,6,7,8,9-hexahydro-2H-pyrrolo[3,4-b]quinoline-3-carboxylic acid ethyl ester

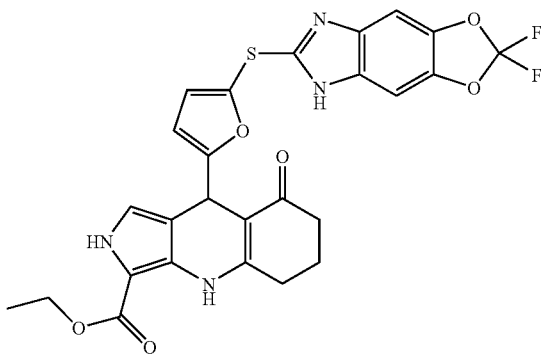

2-Mercaptobenzimidazole Intermediate Preparation

A mixture of 5,6-diamino-2,2-difluoro-1,3-benzodioxole (1 g, 5.31 mmol) and di-2-pyridylthionocarbonate (2.05 g, 8.82 mmol) in 10 ml of tetrahydrofuran is stirred at room temperature for 72 hours. The reaction mixture is then diluted with 100 ml of ethyl acetate and washed with water (2×30 ml). The organic phase is then dried over MgSO₄, filtered and concentrated under reduced pressure. The residue is triturated in diisopropylether and pentane and dried under vacuum to yield 763 mg of 2,2-difluoro-5,7-dihydro-[1,3]dioxolo[4',5':4,5]benzo[1,2-d]imidazole-6-thione as a black powder. Yield=62%. Analytical LC/MS (method B): retention time=3.10 min. m/z=230.97 (positive ion mode).

Aldehyde intermediate preparation: Sodium hydride (60% dispersion in mineral oil, 0.212 g, 5.3 mmol) in tetrahydrofuran (3 ml) is added dropwise over a 15 minute period to a solution of 2,2-difluoro-5,7-dihydro-[1,3]dioxolo[4',5':4,5]benzo[1,2-d]imidazole-6-thione (0.763 g, 3.31 mmol) in tetrahydrofuran (5 ml). The mixture is stirred at room temperature for 2 hours. 5-nitro-2-furaldehyde (0.468 g, 3.31 mmol) in 7 ml of tetrahydrofuran is then added dropwise over a 15 minute period and the mixture is stirred for 2 hours at room temperature. The reaction mixture is then concentrated under reduced pressure and the residue is dissolved in 100 ml of ethyl acetate and washed with water (2×30 ml). The organic phase is dried over MgSO₄ and concentrated under reduced pressure. The residue is purified on a silica gel column (120 g) eluted with a mixture of dichloromethane and methanol (92/5, v/v). The fractions containing the expected product are concentrated under reduced pressure and the residue is triturated in diisopropylether and pentane and dried under vacuum to yield 5-(2,2-difluoro-5H-[1,3]dioxolo[4',5':4,5]benzo[1,2-d]imidazol-6-ylsulfanyl)-furan-2-carbaldehyde as a brown powder. Yield=56%. Analytical LC/MS (method B): retention time=3.66 min., m/z=324.97 (positive ion mode).

A mixture of 3-amino-2-ethoxycarbonyl-pyrrole (0.095 g, 0.62 mmol), 5-(2,2-difluoro-5H-[1,3]dioxolo[4',5':4,5]benzo[1,2-d]imidazol-6-ylsulfanyl)-furan-2-carbaldehyde (0.20 g, 0.62 mmol) and 1,3-cyclohexanedione (0.069 g, 0.62 mmol) in 10 ml of 1-butanol is heated at reflux temperature for 4 h. The reaction mixture is then concentrated under reduced pressure and the residue is purified on a silica gel column (34 g) eluted with a mixture of cyclohexane and ethyl acetate (7/3, v/v). The fractions containing the expected product are concentrated under reduced pressure. The residue is resuspended in 2 ml of acetonitrile, heated at reflux temperature for 30 minutes and let to cool to room temperature. The insoluble material is collected by filtration and dried under vacuum to yield 19 mg of 9-[5-(2,2-difluoro-5H-[1,3]dioxolo[4',5':4,5]benzo[1,2-d]imidazol-6-ylsulfanyl)-furan-2-yl]-8-oxo-4,5,6,7,8,9-hexahydro-2H-pyrrolo[3,4-b]quinoline-3-carboxylic acid ethyl ester. Yield=6%. Analytical LC/MS (method B): m/z=555 (positive ion mode [M+H]⁺), m/z=553 (negative ion mode [M−H]⁻).

400 MHz 1H NMR on a BRUKER AVANCE DRX-400 spectrometer, chemical shifts (δ in ppm) in d6 dimethylsufoxyde (DMSO-d6) solvent referenced at 2.50 ppm at 303K temperature: 1.28 (t, J=7.0 Hz, 3H); 1.91 (m, 2H); 2.26 (m, 2H); 2.60 (m partially masked, 1H); 2.81 (m, 1H); 4.26 (q, J=7.0 Hz, 2H); 5.13 (s, 1H); 5.94 (s broad, 1H); 6.79 (m broad, 2H); 7.48 (m broad, 2H); 8.41 (s broad, 1H); 11.4 (s broad, 1H); 12.8 (m broad, 1H).

EXAMPLE 140

6-tert-Butyloxy-9-[5-(2,2-difluoro-5H-[1,3]dioxolo[4',5':4,5]benzo[1,2-d]imidazol-6-ylsulfanyl)-furan-2-yl]-8-oxo-2,4,5,7,8,9-hexahydro-pyrrolo[3,4-b]-1,7-naphthyridine-3-carboxylic acid ethyl ester

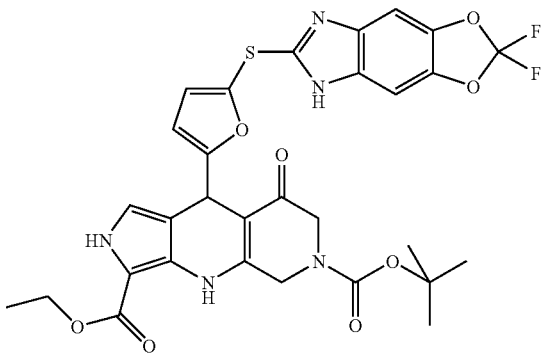

A mixture of 3-amino-2-ethoxycarbonyl-pyrrole (0.142 g, 0.92 mmol), 5-(2,2-difluoro-5H-[1,3]dioxolo[4', 5':4,5]benzo[1,2-d]imidazol-6-ylsulfanyl)-furan-2-carbaldehyde (0.30 g, 0.92 mmol, described in example 139) and N-Boc-3,5-diketopiperidine (0.197 g, 0.92 mmol) in 10 ml of 1-butanol is heated at reflux temperature for 4 h. The reaction mixture is then concentrated under reduced pressure and purified on a silica gel column (34 g) eluted with a mixture of cyclohexane and ethyl acetate (7/3, v/v). The fractions containing the expected product are concentrated under reduced pressure. The residue is triturated in diisopropylether and pentane and dried under vacuum to yield 185 mg of 6-tert-butyloxy-9-[5-(2,2-difluoro-5H-[1,3]dioxolo[4',5':4,5]benzo[1,2-d]imidazol-6-ylsulfanyl)-furan-2-yl]-8-oxo-2,4,5,7,8,9-hexahydro-pyrrolo[3,4-b]-1,7-naphthyridine-3-carboxylic acid ethyl ester. Yield=31%. Analytical LC/MS: m/z=656 (positive ion mode [M+H]$^+$), m/z=654 (negative ion mode [M−H]$^−$).

400 MHz 1H NMR on a BRUKER AVANCE DRX-400 spectrometer, chemical shifts (δ in ppm) in d6 dimethylsufoxyde (DMSO-d6) solvent referenced at 2.50 ppm at 303K temperature: 1.28 (t, J=7.0 Hz, 3H); 1.41 (s broad, 9H); 3.72 (m broad, 1H); 4.13 (m, 2H); 4.27 (q, J=7.0 Hz, 2H); 4.95 (d, J=17.5 Hz, 1H); 5.18 (s, 1H); 5.91 (d, J=3.5 Hz, 1H); 6.82 (s broad, 2H); 7.49 (s broad, 2H); 9.17 (m broad, 1H); 11.5 (s broad, 1H); 12.75 (m broad, 1H).

EXAMPLE 141

9-[5-(2,2-Difluoro-5H-[1,3]dioxolo[4',5':4,5]benzo[1,2-d]imidazol-6-ylsulfanyl)-furan-2-yl]-8-oxo-4,5,6,7,8,9-hexahydro-2H-pyrrolo[3,4-b]-1,7-naphthyridine-3-carboxylic acid ethyl ester hydrochloride

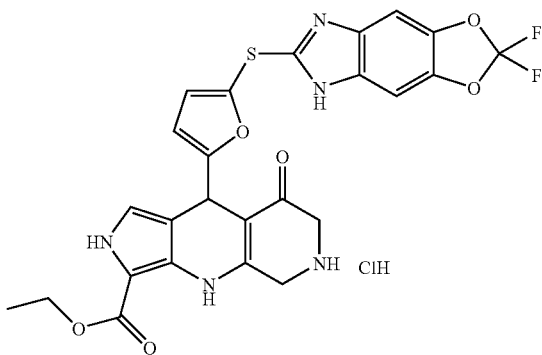

170 mg of 6-tert-butyloxy-9-[5-(2,2-difluoro-5H-[1,3]dioxolo[4',5':4,5]benzo[1,2-d]imidazol-6-ylsulfanyl)-furan-2-yl]-8-oxo-2,4,5,7,8,9-hexahydro-pyrrolo[3,4-b]-1,7-naphthyridine-3-carboxylic acid ethyl ester (example 140) are dissolved in 10 ml of dioxane and combined with 0.94 ml of 4N HCl in dioxane. The reaction mixture is stirred for 16 hours at room temperature. The formed insoluble material is collected by filtration, washed with dioxane (10 ml), diisopropyl ether (10 ml) and pentane (10 ml) and dried under vacuum to yield 150 mg of 9-[5-(2,2-difluoro-5H-[1,3]dioxolo[4',5':4,5]benzo[1,2-d]imidazol-6-ylsulfanyl)-furan-2-yl]-8-oxo-4,5,6,7,8,9-hexahydro-2H-pyrrolo[3,4-b]-1,7-naphthyridine-3-carboxylic acid ethyl ester hydrochloride. Yield=98%. Analytical LC/MS (method B): m/z=554 (negative ion mode [M−H]$^−$), m/z=556 (positive ion mode [M+H]$^+$)

400 MHz 1H NMR on a BRUKER AVANCE DRX-400 spectrometer, chemical shifts (δ in ppm) in d6 dimethylsufoxyde (DMSO-d6) solvent referenced at 2.50 ppm at 303K temperature: 1.29 (t, J=7.0 Hz, 3H); de 3.65 à 3.90 (m partially masked, 2H); 4.23 (m, 1H); 4.29 (q, J=7.0 Hz, 2H); 4.45 (d broad, J=17.0 Hz, 1H); 5.19 (s, 1H); 6.31 (s broad, 1H); 6.86 (m, 2H); 7.54 (s, 2H); 9.36 (s, 1H); 9.84 (m broad, 1H); 10.05 (m broad, 1H); 11.65 (s broad, 1H).

EXAMPLE 142

9-[5-(4,6-Difluoro-1H-benzimidazol-2-ylsulfanyl)-furan-2-yl]-8-oxo-4,5,6,7,8,9-hexahydro-2H-pyrrolo[3,4-b]quinoline-3-carboxylic acid ethyl ester

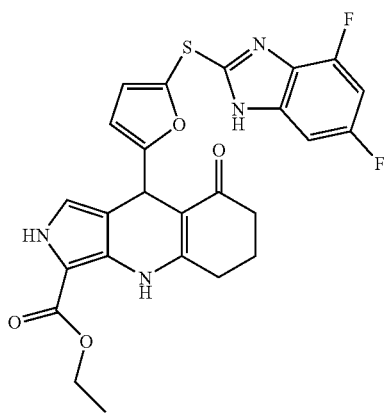

2-Mercaptobenzimidazole Intermediate Preparation:
A mixture of 1,2-diamino-3,5-difluorobenzene (1 g, 6.94 mmol) and 1,1'-thiocarbonyldiimidazole (2.05 g, 11.52 mmol) in 10 ml of tetrahydrofuran is stirred at room temperature for 16 hours. The reaction mixture is then concentrated under reduced pressure and the residue is dissolved in 100 ml of ethyl acetate and washed with water (2×30 ml). The organic phase is then dried over MgSO$_4$, filtered and concentrated under reduced pressure to yield 763 mg of 2-mercapto-4,6-difluorobenzimidazole. Yield=61%. Analytical LC/MS (method B): retention time=2.49 min. m/z=186.95 (positive ion mode).

Aldehyde Intermediate Preparation:
2-mercapto-4,6-difluorobenzimidazole (16 g, 86 mmol), in tetrahydrofuran (80 ml) is added dropwise to a mixture of sodium hydride (60% dispersion in mineral oil, 5.5 g, 86 mmol) and tetrahydrofuran (20 ml) at 0° C. The mixture is stirred at room temperature for 3 hours. 5-nitro-2-furaldehyde (12.1 g, 86 mmol) in 50 ml of tetrahydrofuran is then added dropwise over a 15 minute period and the mixture is stirred for 16 hours at room temperature. Water (10 ml) is then added and the reaction mixture is stirred for 30 min. The reaction mixture is then concentrated under reduced pressure. The residue is dissolved in a minimal volume of ethyl acetate and the solution is filtered on a plug (50 ml) of silica gel. The silica gel plug is washed with ethyl acetate (1 l) and the filtrate is concenterated under reduced pressure. The residue is purified on a silica gel column (300 g) eluted successively with cyclohexane/ethyl acetate (9/1 v/v) and cyclohexane/ethyl acetate (7/3 v/v).

The fractions containing the expected product are concentrated under reduced pressure to yield 6.7 g of 5-(4,6-difluoro-1H-benzimidazol-2-ylsulfanyl)-furan-2-carbaldehyde as an orange powder. Yield=28%. Analytical LC/MS (method B): retention time=3.34 min., m/z=281.0 (positive ion mode).

A mixture of 3-amino-2-ethoxycarbonyl-pyrrole (3.19 g, 20.7 mmol), 5-(4,6-difluoro-1H-benzimidazol-2-ylsulfanyl)-furan-2-carbaldehyde (5.80 g, 20.7 mmol) and 1,3-cyclohexanedione (2.32 g, 20.7 mmol) in 80 ml of 1-butanol is heated at reflux temperature for 3 hours. The reaction mixture is then concentrated under reduced pressure and the residue is purified on a silica gel column (150 g) eluted successively with cyclohexane/ethyl acetate (9/1, v/v) and cyclohexane/ethyl acetate (7/3, v/v). The fractions containing the expected product are concentrated under reduced pressure. The residue is resuspended in 100 ml of acetonitrile and heated at reflux temperature for 30 minutes. The mixture is allowed to cool to room temperature and the insoluble material is collected by filtration. The solid is washed with acetonitrile (400 ml), diisopropyl ether (100 ml) and pentane (100 ml) and dried under vacuum to yield 3.8 g of 9-[5-(4,6-difluoro-1H-benzimidazol-2-ylsulfanyl)-furan-2-yl]-8-oxo-4,5,6,7,8,9-hexahydro-2H-pyrrolo[3,4-b]quinoline-3-carboxylic acid ethyl ester as a white powder. Yield=36%. Analytical LC/MS method B: m/z=509 (negative ion mode [M−H]⁻), m/z=511 (positive ion mode [M+H]⁺).

500 MHz 1H NMR on a BRUKER AVANCE DRX-500 spectrometer, chemical shifts (δ in ppm) in d6 dimethylsufoxyde (DMSO-d6) solvent referenced at 2.50 ppm at 303K temperature: 1.28 (t, J=7.0 Hz, 3H); 1.89 (m, 2H); 2.24 (m, 2H); 2.57 (m, 2H); 2.79 (m, 1H); 4.25 (q, J=7.0 Hz, 2H); 5.14 (s, 1H); 5.98 (d, J=3.5 Hz, 1H); 6.78 (d, J=3.5 Hz, 1H); 6.84 (d, J=3.5 Hz, 1H); 7.02 (m broad, 1H); 7.13 (m broad, 1H); 8.45 (s, 1H); 11.4 (s broad, 1H); 13.0 (m broad, 1H).

EXAMPLE 143

9-[5-(5,7-Difluoro-1H-benzimidazol-2-ylsulfanyl)-furan-2-yl]-8-oxo-4,5,6,7,8,9-hexahydro-2H-pyrrolo[3,4-b]-1,7-naphthyridine-3-carboxylic acid ethyl ester hydrochloride

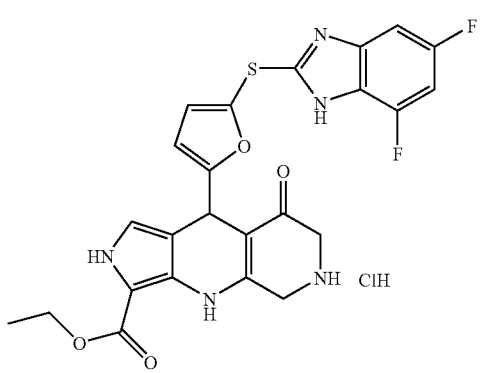

Preparation of the Boc-Protected Intermediate:

A mixture of 3-amino-2-ethoxycarbonyl-pyrrole (0.165 g, 1.07 mmol), 5-(4,6-difluoro-1H-benzimidazol-2-ylsulfanyl)-furan-2-carbaldehyde (described in example 142, 0.30 g, 1.07 mmol) and N-Boc-3,5-diketopiperidine (0.228 g, 1.07 mmol) in 5 ml of 1-butanol is heated at reflux temperature for 3 hours. The reaction mixture is then concentrated under reduced pressure and the residue is purified on a silica gel column (40 g) eluted successively with cyclohexane/ethyl acetate (9/1, v/v) and cyclohexane/ethyl acetate (1/1, v/v). The fractions containing the expected product are concentrated under reduced pressure. The residue is triturated in diisopropylether (20 ml) and pentane (20 ml), collected by filtration and dried under vacuum to yield 300 mg of 6-tert-butyloxy-9-[5-(5,7-difluoro-1H-benzimidazol-2-ylsulfanyl)-furan-2-yl]-8-oxo-2,4,5,7,8,9-hexahydro-pyrrolo[3,4-b]-1,7-naphthyridine-3-carboxylic acid ethyl ester. Yield=46%. Analytical LC/MS (method B): retention time=4.31 min., m/z=612.21 (positive ion mode).

A solution of 300 mg of 6-tert-butyloxy-9-[5-(5,7-difluoro-1H-benzimidazol-2-ylsulfanyl)-furan-2-yl]-8-oxo-2,4,5,7,8,9-hexahydro-pyrrolo[3,4-b]-1,7-naphthyridine-3-carboxylic acid ethyl ester in 10 ml of dioxane is combined with 1.8 ml of 4N HCl in dioxane and the reaction mixture is stirred for 16 hours at room temperature. The formed insoluble material is collected by filtration, washed with dioxane (70 ml), pentane (50 ml), diisopropylether (50 ml) and dried under vacuum to yield 227 mg of 9-[5-(5,7-difluoro-1H-benzimidazol-2-ylsulfanyl)-furan-2-yl]-8-oxo-4,5,6,7,8,9-hexahydro-2H-pyrrolo[3,4-b]-1,7-naphthyridine-3-carboxylic acid ethyl ester hydrochloride as a light brown powder. Yield=84%. Analytical LC/MS (method C): m/z=511 (negative ion mode [M−H]⁻), m/z=512 (positive ion mode [M+H]⁺) 500 MHz 1H NMR on a BRUKER AVANCE DRX-500 spectrometer, chemical shifts (δ in ppm) in d6 dimethylsufoxyde (DMSO-d6) solvent referenced at 2.50 ppm at 303K temperature: 1.28 (t, J=7.0 Hz, 3H); 3.72 (d broad, J=16.0 Hz, 1H); 3.81 (m, 1H); 4.22 (m, 1H); 4.28 (q, J=7.0 Hz, 2H); 4.45 (d broad, J=16.0 Hz, 1H); 5.20 (s, 1H); 6.40 (d, J=3.5 Hz, 1H); 6.85 (d, J=3.5 Hz, 1H); 6.90 (d, J=3.5 Hz, 1H); 7.06 (dt, J=2.0 et 11.0 Hz, 1H); 7.17 (dd, J=2.0 et 8.5 Hz, 1H); 9.39 (s, 1H); 10.1 (m broad, 1H); 10.4 (m broad, 1H); 11.65 (d, J=3.5 Hz, 1H).

EXAMPLE 144

4-[5-(5,7-Difluoro-1H-benzimidazol-2-ylsulfanyl)-furan-2-yl]-2,4,6,7,8,9-hexahydro-pyrazolo[3,4-b]quinolin-5-one

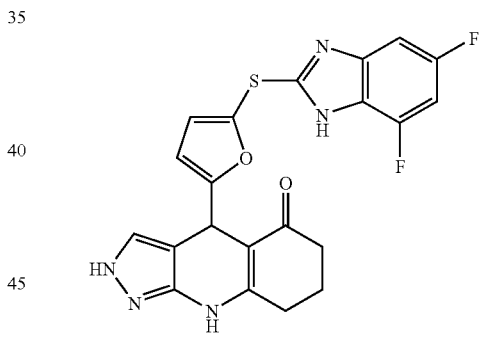

A mixture of 3-aminopyrazole (0.089 g, 1.07 mmol), 5-(4,6-difluoro-1H-benzimidazol-2-ylsulfanyl)-furan-2-carbaldehyde (described in example 142, 0.30 g, 1.07 mmol) and 1,3-cyclohexanedione (0.12 g, 1.07 mmol) in 5 ml of 1-butanol is heated at reflux temperature for 3 hours. The reaction mixture is then concentrated under reduced pressure and the residue is purified on a silica gel column (40 g) eluted with a mixture of cyclohexane and ethyl acetate (2/8, v/v). The fractions containing the expected product are concentrated under reduced pressure and the obtained solid is washed with pentane (25 ml) and diisopropylether (25 ml) and dried under vacuum to yield 323 mg of 4-[5-(5,7-difluoro-1H-benzimidazol-2-ylsulfanyl)-furan-2-yl]-2,4,6,7,8,9-hexahydro-pyrazolo[3,4-b]quinolin-5-one as a white powder. Yield=69%. Analytical LC/MS (method C): m/z=438 (negative ion mode [M−H]⁻), m/z=440 (positive ion mode [M+H]+)

500 MHz 1H NMR on a BRUKER AVANCE DRX-500 spectrometer, chemical shifts (δ in ppm) in d6 dimethylsufoxyde (DMSO-d6) solvent referenced at 2.50 ppm at 303K temperature: 1.88 (m, 2H); 2.24 (m, 2H); 2.55 (m partially masked, 2H); 5.17 (s, 1H); 5.97 (d, J=3.5 Hz, 1H); 6.84 (d, J=3.5 Hz, 1H); 7.03 (t broad, J=10.5 Hz, 1H); 7.12 (d broad, J=8.5 Hz, 1H); 7.44 (s, 1H); 9.94 (s, 1H); 12.15 (s, 1H); 12.95 (m broad, 1H).

EXAMPLE 145

4-[5-(5,7-Difluoro-1H-benzimidazol-2-ylsulfanyl)-furan-2-yl]-2,4,6,7,8,9-hexahydro-pyrazolo[3,4b]-1,7-naphthyridin-5-one hydrochloride

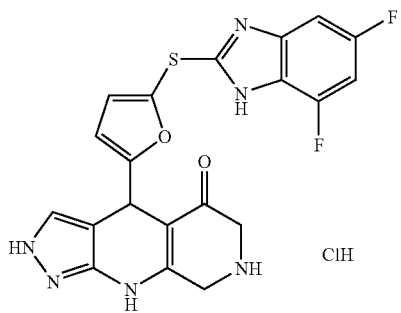

Preparation of the Boc Protected Intermediate:

A mixture of 3-aminopyrazole (0.089 g, 1.07 mmol), 5-(4,6-difluoro-1H-benzimidazol-2-ylsulfanyl)-furan-2-carbaldehyde (described in example 142, 0.30 g, 1.07 mmol) and N-Boc-3,5-diketopiperidine (0.228 g, 1.07 mmol) in 5 ml of 1-butanol is heated at reflux temperature for 3 hours. The reaction mixture is then concentrated under reduced pressure and the residue is purified on a silica gel column (40 g) eluted successively with cyclohexane/ethyl acetate (9/1, v/v). The fractions containing the expected product are concentrated under reduced pressure to yield 360 mg of 7-tert-butyloxy-4-[5-(5,7-difluoro-1H-benzimidazol-2-ylsulfanyl)-furan-2-yl]-5-oxo-2,4,6,7,8,9-hexahydro-pyrazolo[3,4b]-1,7-naphthyridine. Yield=62%. Analytical LC/MS (method B): retention time=3.82 min., m/z=541.24 (positive ion mode).

A solution of 360 mg of 7-tert-butyloxy-4-[5-(5,7-difluoro-1H-benzimidazol-2-ylsulfanyl)-furan-2-yl]-5-oxo-2,4,6,7,8,9-hexahydro-pyrazolo[3,4b]-1,7-naphthyridine in 10 ml of dioxane is combined with 2.5 ml of 4N HCl in dioxane and the reaction mixture is stirred at room temperature for 16 hours. The formed insoluble material is collected by filtration, washed with dioxane (100 ml), diisopropylether (60 ml), pentane (60 ml) and dried under vacuum to yield 320 mg of 4-[5-(5,7-difluoro-1H-benzimidazol-2-ylsulfanyl)-furan-2-yl]-2,4,6,7,8,9-hexahydro-pyrazolo[3,4b]-1,7-naphthyridin-5-one hydrochloride as an orange powder. Quantitative yield. Analytical LC/MS (method C): m/z=439 (negative ion mode [M−H]⁻), m/z=441 (positive ion mode [M+H]⁺)

500 MHz 1H NMR on a BRUKER AVANCE DRX-500 spectrometer, chemical shifts (δ in ppm) in d6 dimethylsufoxyde (DMSO-d6) solvent referenced at 2.50 ppm at 303K temperature: from 3.50 to 4.00 (m partially masked, 2H); 4.12 (d broad, J=16.5 Hz, 1H); 4.22 (m, 1H); 5.25 (s, 1H); 6.36 (d, J=3.5 Hz, 1H); 6.90 (d, J=3.5 Hz, 1H); 7.06 (dt, J=2.0 et 11.0 Hz, 1H); 7.15 (dd, J=2.0 et 9.0 Hz, 1H); 7.55 (s, 1H); 9.97 (m broad, 1H); 10.15 (m broad, 1H); 10.7 (s broad, 1H); 12.4 (m broad, 1H).

EXAMPLE 146

9-[5-(6-Chloro-5-fluoro-1H-benzimidazol-2-ylsulfanyl)-furan-2-yl]-8-oxo-4,5,6,7,8,9-hexahydro-2H-pyrrolo[3,4-b]quinoline-3-carboxylic acid ethyl ester

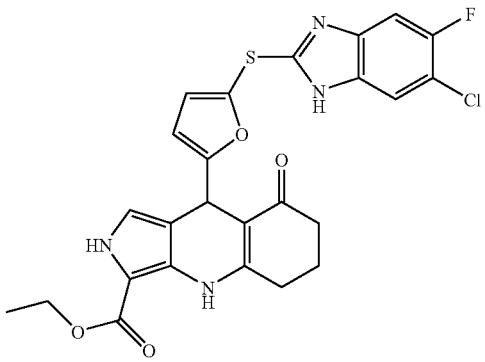

2-Mercaptobenzimidazole Intermediate Preparation:

Di-2-pyridylthionocarbonate (2.31 g, 9.96 mmol) is added by portions to a solution of 1,2-diamino-4-chloro-5-fluorobenzene (1 g, 6.22 mmol) in 10 ml of tetrahydrofuran and the mixture is stirred at room temperature for 16 hours. The reaction mixture is then concentrated under reduced pressure and the residue is dissolved in 100 ml of ethyl acetate and washed with water (2×30 ml). The organic phase is then dried over MgSO₄, filtered and concentrated under reduced pressure to yield 1.2 g of 2-mercapto-5-chloro-6-fluoro-benzimidazole as a yellow powder. Yield=95%. Analytical LC/MS (method B): retention time=2.90 min. m/z=202.95 (1 Cl, positive ion mode).

Aldehyde Intermediate Preparation:

A solution of 2-mercapto-5-chloro-6-fluoro-benzimidazole (1.2 g, 5.92 mmol) in tetrahydrofuran (10 ml) is added dropwise to a mixture of sodium hydride (60% dispersion in mineral oil, 0.379 g, 9.47 mmol) and tetrahydrofuran (5 ml). The mixture is stirred at room temperature for 2 hours. A solution of 5-nitro-2-furaldehyde (0.836 g, 5.92 mmol) in tetrahydrofuran (15 ml) is then added dropwise over a 15 minute period and the mixture is stirred for 16 hours at room temperature. The reaction mixture is concentrated under reduced pressure and the residue is dissolved in 100 ml of ethyl acetate and washed with water (2×30 ml). The organic phase is dried over MgSO₄ and concentrated under reduced pressure. The residue is purified on a silica gel column (120 g) eluted with a mixture of dichloromethane and methanol (98/2, v/v) to yield 370 mg of 5-(6-chloro-5-fluoro-1H-benzimidazol-2-ylsulfanyl)-furan-2-carbaldehyde as an orange powder. Yield=21%. Analytical LC/MS (method B): retention time=3.58 min., m/z=296.98 (1 Cl, positive ion mode).

A mixture of 3-amino-2-ethoxycarbonyl-pyrrole (0.192 g, 1.25 mmol), 5-(6-chloro-5-fluoro-1H-benzimidazol-2-ylsulfanyl)-furan-2-carbaldehyde (0.37 g, 1.25 mmol) and 1,3-cyclohexanedione (0.14 g, 1.25 mmol) in 5 ml of 1-butanol is heated at reflux temperature for 2 hours. The reaction mixture is then concentrated under reduced pressure. The residue is resuspended in 5 ml of acetonitrile and the mixture is heated at reflux temperature for 30 minutes. The mixture is allowed to cool to room temperature and the insoluble material is collected by filtration, washed with diisopropylether (20 ml), pentane (20 ml) and dried under vacuum to yield 363 mg of 9-[5-(6-chloro-5-fluoro-1H-benzimidazol-2-ylsulfanyl)-furan-2-yl]-8-oxo-4,5,6,7,8,9-hexahydro-2H-pyrrolo[3,4-b]quinoline-3-carboxylic acid ethyl ester as a white powder. Yield=55%. Analytical LC/MS (method B): m/z=525 (negative ion mode, [M−H]⁻, 1 Cl present), m/z=527 (positive ion mode, [M+H]⁺, 1 Cl present).

400 MHz 1H NMR on a BRUKER AVANCE DRX-400 spectrometer, chemical shifts (δ in ppm) in d6 dimethylsufoxyde (DMSO-d6) solvent referenced at 2.50 ppm at 303K temperature: 1.28 (t, J=7.0 Hz, 3H); 1.91 (m, 2H); 2.25 (m, 2H); 2.58 (m, 1H); 2.80 (m, 1H); 4.26 (q, J=7.0 Hz, 2H); 5.14 (s, 1H); 5.97 (d, J=3.5 Hz, 1H); 6.79 (d, J=3.5 Hz, 1H); 6.83 (d, J=3.5 Hz, 1H); 7.50 (d, J=9.5 Hz, 1H); 7.65 (d, J=7.0 Hz, 1H); 8.43 (s, 1H); 11.4 (d, J=3.5 Hz, 1H); 12.75 (m broad, 1H).

EXAMPLE 147

9-[5-(6-Chloro-5-fluoro-1H-benzimidazol-2-ylsulfanyl)-furan-2-yl]-8-oxo-4,5,6,7,8,9-hexahydro-2H-pyrrolo[3,4-b]-1,7-naphthyridine-3-carboxylic acid ethyl ester hydrochloride

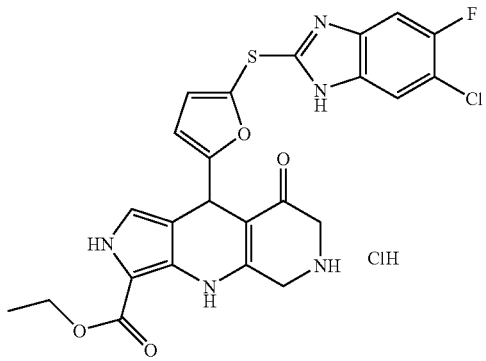

Boc-Protected Intermediate Preparation:

A mixture of 3-amino-2-ethoxycarbonyl-pyrrole (0.208 g, 1.35 mmol), 5-(6-chloro-5-fluoro-1H-benzimidazol-2-ylsulfanyl)-furan-2-carbaldehyde (described in example 146, 0.40 g, 1.35 mmol) and N-Boc-3,5-diketopiperidine (0.287 g, 1.35 mmol) in 5 ml of 1-butanol is heated at reflux temperature for 2 hours and stirred at room temperature for an additional 16 hour period. The reaction mixture is then concentrated under reduced pressure and the residue is resuspended in 7.5 ml of acetonitrile and heated at reflux temperature for 30 min. The mixture is allowed to cool to room temperature and the insoluble material is collected by filtration, washed with pentane (20 ml), diisopropylether (20 ml) and dried under vacuum to yield 376 mg of 6-tert-butyloxy-9-[5-(6-chloro-5-fluoro-1H-benzimidazol-2-ylsulfanyl)-furan-2-yl]-8-oxo-2,4,5,7,8,9-hexahydro-pyrrolo[3,4-b]-1,7-naphthyridine-3-carboxylic acid ethyl ester. Yield=44%. Analytical LC/MS (method B): retention time=4.47 min., m/z=628.03 (positive ion mode).

A solution of 6-tert-butyloxy-9-[5-(6-chloro-5-fluoro-1H-benzimidazol-2-ylsulfanyl)-furan-2-yl]-8-oxo-2,4,5,7,8,9-hexahydro-pyrrolo[3,4-b]-1,7-naphthyridine-3-carboxylic acid ethyl ester (0.376 g, 0.60 mmol) in dioxane (20 ml) is combined with 4 N HCl in dioxane (2.17 ml) and the mixture is stirred at room temperature for 16 hours. The formed insoluble material is collected by filtration, washed with dioxane (40 ml), pentane (40 ml), diisopropylether (40 ml) and dried under vacuum to yield 310 mg of 9-[5-(6-chloro-5-fluoro-1H-benzimidazol-2-ylsulfanyl)-furan-2-yl]-8-oxo-4,5,6,7,8,9-hexahydro-2H-pyrrolo[3,4-b]-1,7-naphthyridine-3-carboxylic acid ethyl ester hydrochloride as a light brown powder. Yield=92%. Analytical LC/MS (method B): m/z=528 (positive ion mode, [M+H]⁺, 1 Cl present), m/z=526 (negative ion mode [M−H]⁻, 1 Cl present)

500 MHz 1H NMR on a BRUKER AVANCE DRX-500 spectrometer, chemical shifts (δ in ppm) in d6 dimethylsufoxyde (DMSO-d6) solvent referenced at 2.50 ppm at 303K temperature: 1.29 (t, J=7.0 Hz, 3H); 3.73 (m, 1H); 3.81 (m, 1H); 4.23 (m, 1H); 4.28 (m, 2H); 4.46 (d broad, J=17.0 Hz, 1H); 5.19 (s, 1H); 6.39 (d, J=3.5 Hz, 1H); 6.86 (d, J=3.5 Hz, 1H); 6.89 (d, J=3.5 Hz, 1H); 7.55 (d, J=9.5 Hz, 1H); 7.70 (d, J=7.0 Hz, 1H); 9.38 (s, 1H); 10.05 (m broad, 1H); 10.35 (m broad, 1H); 11.7 (d, J=3.5 Hz, 1H).

EXAMPLE 148

9-[5-(5-Fluoro-1H-benzimidazol-2-ylsulfanyl)-furan-2-yl]-8-oxo-4,5,6,7,8,9-hexahydro-2H-pyrrolo[3,4-b]quinoline-3-carboxylic acid ethyl ester

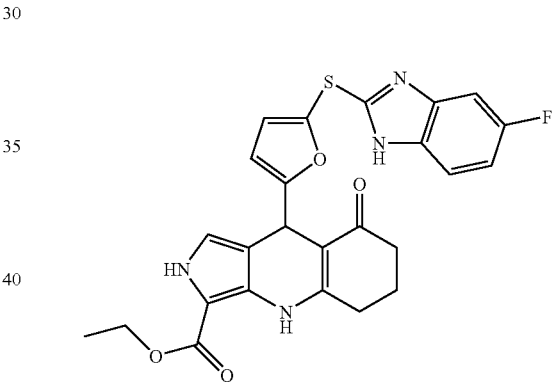

2-Mercaptobenzimidazole Intermediate Preparation:

Di-2-pyridylthionocarbonate (3.68 g, 15.9 mmol) is added by portions to a solution of 4-fluoro-ortho-phenylenediamine (2 g, 15.9 mmol) in 20 ml of tetrahydrofuran and the mixture is stirred at room temperature for 16 hours. The reaction mixture is then concentrated under reduced pressure and the residue is dissolved in 200 ml of ethyl acetate and washed with water (2×60 ml). The organic phase is then dried over MgSO₄, filtered and concentrated. The residue is triturated in diisopropylether and pentane and dried under vacuum to yield 2.24 g of 2-mercapto-5-fluoro-benzimidazole as a brown powder. Yield=84%. Analytical LC/MS (method B): retention time=2.32 min. m/z=168.97 (positive ion mode).

Aldehyde Intermediate Preparation:

A solution of 2-mercapto-5-fluoro-benzimidazole (2.24 g, 13.3 mmol) in tetrahydrofuran (10 ml) is added dropwise to a mixture of sodium hydride (60% dispersion in mineral oil, 0.852 g, 21.3 mmol) and tetrahydrofuran (5 ml). The mixture is stirred at room temperature for 2 hours. A solution of 5-nitro-2-furaldehyde (1.88 g, 13.3 mmol) in tetrahydrofuran (15 ml) is then added dropwise over a 15 minute period and the mixture is stirred for 2 hours at room temperature. The reaction mixture is concentrated under reduced pressure and the residue is dissolved in 200 ml of ethyl acetate and washed with water (2×60 ml). The organic phase is dried over MgSO$_4$ and concentrated under reduced pressure. The residue is purified on a silica gel column (40 g) eluted with dichloromethane to yield 700 mg of 5-(5-fluoro-1H-benzoimidazol-2-ylsulfanyl)-furan-2-carbaldehyde as an orange powder. Yield=20%. Analytical LC/MS (method B): retention time=3.08 min., m/z=263.05 (positive ion mode).

A mixture of 3-amino-2-ethoxycarbonyl-pyrrole (0.235 g, 1.52 mmol), 5-(5-fluoro-1H-benzoimidazol-2-ylsulfanyl)-furan-2-carbaldehyde (0.40 g, 1.52 mmol) and 1,3-cyclohexanedione (0.171 g, 1.52 mmol) in 5 ml of 1-butanol is heated at reflux temperature for 2 hours. The reaction mixture is then concentrated under reduced pressure. The residue is resuspended in 5 ml of acetonitrile and the mixture is heated at reflux temperature for 30 minutes. The mixture is allowed to cool to room temperature and the insoluble material is collected by filtration, washed with diisopropylether (20 ml), pentane (20 ml) and dried under vacuum to yield 377 mg of 9-[5-(5-fluoro-1H-benzoimidazol-2-ylsulfanyl)-furan-2-yl]-8-oxo-4,5,6,7,8,9-hexahydro-2H-pyrrolo[3,4-b]quinoline-3-carboxylic acid ethyl ester as a white powder. Yield=50%. Analytical LC/MS (method B): m/z=491 (negative ion mode, [M−H]$^-$), m/z=493 (positive ion mode [M+H]$^+$).

400 MHz 1H NMR on a BRUKER AVANCE DRX-400 spectrometer, chemical shifts (δ in ppm) in d6 dimethylsufoxyde (DMSO-d6) solvent referenced at 2.50 ppm at 303K temperature: 1.28 (t, J=7.0 Hz, 3H); 1.89 (m, 2H); 2.26 (m, 2H); 2.58 (m, 1H); 2.80 (m, 1H); 4.25 (q, J=7.0 Hz, 2H); 5.14 (s, 1H); 5.96 (d, J=3.5 Hz, 1H); 6.79 (d, J=3.5 Hz, 1H); 6,82 (d, J=3.5 Hz, 1H); 7.00 (dt, J=2.5 et 9.0 Hz, 1H); 7.27 (d broad, J=9.5 Hz, 1H); 7.45 (m broad, 1H); 8.42 (s, 1H); 11.4 (s broad, 1H); 12.5 (m broad, 1H).

EXAMPLE 149

9-[5-(5-Fluoro-1H-benzimidazol-2-ylsulfanyl)-furan-2-yl]-8-oxo-4,5,6,7,8,9-hexahydro-2H-pyrrolo[3,4-b]-1,7-naphthyridine-3-carboxylic acid ethyl ester hydrochloride

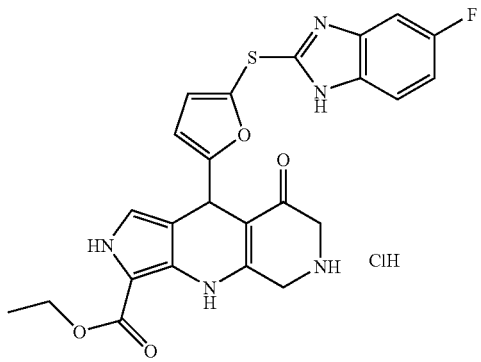

Boc-Protected Intermediate Preparation:

A mixture of 3-amino-2-ethoxycarbonyl-pyrrole (0.235 g, 1.52 mmol), 5-(5-fluoro-1H-benzoimidazol-2-ylsulfanyl)-furan-2-carbaldehyde (described in example 148, 0.40 g, 1.52 mmol) and N-Boc-3,5-diketopiperidine (0.325 g, 1.52 mmol) in 5 ml of 1-butanol is heated at reflux temperature for 2 hours and stirred at room temperature for an additional 16 hour period. The reaction mixture is then concentrated under reduced pressure and the residue is resuspended in 7.5 ml of acetonitrile and heated to reflux temperature for 30 min. The mixture is allowed to cool to room temperature and the insoluble material is collected by filtration, washed with pentane (20 ml), diisopropylether (20 ml) and dried under vacuum to yield 380 mg of 6-tert-butyloxy-9-[5-(5-fluoro-1H-benzimidazol-2-ylsulfanyl)-furan-2-yl]-8-oxo-2,4,5,7,8,9-hexahydro-pyrrolo[3,4-b]-1,7-naphthyridine-3-carboxylic acid ethyl ester as a white powder. Yield=42%. Analytical LC/MS (method B): retention time=4.1 min., m/z=594.03 (positive ion mode).

A solution of 6-tert-butyloxy-9-[5-(5-fluoro-1H-benzimidazol-2-ylsulfanyl)-furan-2-yl]-8-oxo-2,4,5,7,8,9-hexahydro-pyrrolo[3,4-b]-1,7-naphthyridine-3-carboxylic acid ethyl ester (0.380 g, 0.64 mmol) in dioxane (20 ml) is combined with 4 N HCl in dioxane (2.32 ml) and the mixture is stirred at room temperature for 16 hours. The formed insoluble material is collected by filtration, washed with dioxane (40 ml), pentane (40 ml), diisopropylether (40 ml) and dried under vacuum to yield 323 mg of 9-[5-(5-fluoro-1H-benzimidazol-2-ylsulfanyl)-furan-2-yl]-8-oxo-4,5,6,7,8,9-hexahydro-2H-pyrrolo[3,4-b]-1,7-naphthyridine-3-carboxylic acid ethyl ester hydrochloride as a orange-brown powder. Yield=95%. Analytical LC/MS method B: m/z=492 (negative ion mode [M−H]$^-$), m/z=494 (positive ion mode [M+H]$^+$).

500 MHz 1H NMR on a BRUKER AVANCE DRX-500 spectrometer, chemical shifts (δ in ppm) in d6 dimethylsufoxyde (DMSO-d6) solvent referenced at 2.50 ppm at 303K temperature: 1.29 (t, J=7.0 Hz, 3H); de 3.69 à 3.85 (m, 2H); 4.23 (m, 1H); 4.29 (m, 2H); 4.45 (d broad, J=16.0 Hz, 1H); 5.20 (s, 1H); 6.36 (d, J=3.5 Hz, 1H); 6.87 (d, J=3.5 Hz, 1H); 6.89 (d, J=3.5 Hz, 1H); 7.04 (dt, J=2.5 et 9.0 Hz, 1H); 7.32 (dd, J=2.5 et 9.0 Hz, 1H); 7.49 (dd, J=4.5 et 9.0 Hz, 1H); 9.39 (s, 1H); 9.96 (m broad, 1H); 10.2 (m broad, 1H); 11.7 (d, J=3.5 Hz, 1H).

EXAMPLE 150

8-Oxo-9-[5-(5-trifluoromethoxy-1H-benzimidazol-2-ylsulfanyl)-furan-2-yl]-4,5,6,7,8,9-hexahydro-2H-pyrrolo[3,4-b]quinoline-3-carboxylic acid ethyl ester

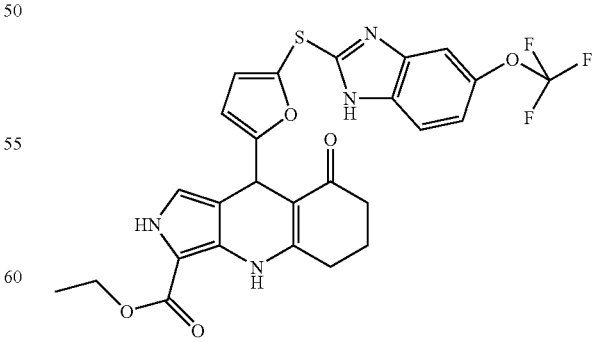

2-Mercaptobenzimidazole Intermediate Preparation:

1,1'-thiocarbonyldiimidazole (1.13 g, 6.25 mmol) is added by portions to a solution of 4-(trifluoromethoxy)-ortho-phenylenediamine (1 g, 5.2 mmol) in 5 ml of tetrahydrofuran and the mixture is stirred at room temperature for 16 hours. The reaction mixture is then concentrated under reduced pressure and the residue is dissolved in 100 ml of ethyl acetate and washed with water (2×30 ml). The organic phase is then dried over MgSO$_4$, filtered and concentrated. The residue is triturated in diisopropylether and pentane and dried under vacuum to yield 1.26 g of 2-mercapto-5-trifluoromethoxy-benzimidazole as a yellow powder. Quantitative yield. Analytical LC/MS (method B): retention time=3.69 min. m/z=235.67 (positive ion mode).

Aldehyde Intermediate Preparation:

A solution of 2-mercapto-5-trifluoromethoxy-benzimidazole (1.26 g, 5.38 mmol) in tetrahydrofuran (10 ml) is added dropwise to a mixture of sodium hydride (60% dispersion in mineral oil, 0.344 g, 8.61 mmol) and tetrahydrofuran (5 ml) at 0° C. The mixture is stirred at room temperature for 2 hours. A solution of 5-nitro-2-furaldehyde (0.76 g, 5.38 mmol) in tetrahydrofuran (15 ml) is then added dropwise over a 15 minute period and the mixture is stirred for 16 hours at room temperature. The reaction mixture is concentrated under reduced pressure and the residue is dissolved in 10 ml of dichloromethane and filtered through a silica gel plug (40 ml). The silica gel plug is eluted with 800 ml of cylohexane/ethyl acetate (7/3, v/v). The organic filtrates are combined and concentrated under reduced pressure to yield 1.1 g of 5-(5-trifluoromethoxy-1H-benzoimidazol-2-ylsulfanyl)-furan-2-carbaldehyde as an oil. Yield=62%. Analytical LC/MS (method B): retention time=3.77 min., m/z=329.0 (positive ion mode).

A mixture of 3-amino-2-ethoxycarbonyl-pyrrole (0.235 g, 1.52 mmol), 5-(5-trifluoromethoxy-1H-benzoimidazol-2-ylsulfanyl)-furan-2-carbaldehyde (0.50 g, 1.52 mmol) and 1,3-cyclohexanedione (0.171 g, 1.52 mmol) in 5 ml of 1-butanol is heated at reflux temperature for 4 hours. The reaction mixture is then concentrated under reduced pressure. The residue is then purified on a silica gel column (40 g) eluted successively with cyclohexane/ethyl acetate (7/3, v/v) and cyclohexane/ethyl acetate (1/1, v/v). The fractions containing the expected product are concentrated under reduced pressure. The obtained solid is washed with acetonitrile (100 ml), pentane (50 ml) and dried under vacuum to yield 310 mg of 8-oxo-9-[5-(5-trifluoromethoxy-1H-benzoimidazol-2-ylsulfanyl)-furan-2-yl]-4,5,6,7,8,9-hexahydro-2H-pyrrolo[3,4-b]quinoline-3-carboxylic acid ethyl ester as a white powder. Yield=36%. Analytical LC/MS (method C): m/z=559 (positive ion mode [M+H]$^+$), m/z=557 (negative ion mode [M−H]$^−$).

400 MHz 1H NMR on a BRUKER AVANCE DRX-400 spectrometer, chemical shifts (δ in ppm) in d6 dimethylsufoxyde (DMSO-d6) solvent referenced at 2.50 ppm at 303K temperature: 1.28 (t, J=7.0 Hz, 3H); 1.90 (m, 2H); 2.25 (m, 2H); 2.58 (m, 1H); 2.79 (m, 1H); 4.26 (q, J=7.0 Hz, 2H); 5.15 (s, 1H); 5.98 (d, J=3.5 Hz, 1H); 6.79 (d, J=3.5 Hz, 1H); 6.82 (d, J=3.5 Hz, 1H); 7.11 (d broad, J=8.5 Hz, 1H); 7.44 (s broad, 1H); 7.52 (d, J=8.5 Hz, 1H); 8.41 (s, 1H); 11.4 (s broad, 1H).

EXAMPLE 151

8-Oxo-9-[5-(5-trifluoromethoxy-1H-benzimidazol-2-ylsulfanyl)-furan-2-yl]-4,5,6,7,8,9-hexahydro-2H-pyrrolo[3,4-b][1,7]naphthyridine-3-carboxylic acid ethyl ester hydrochloride

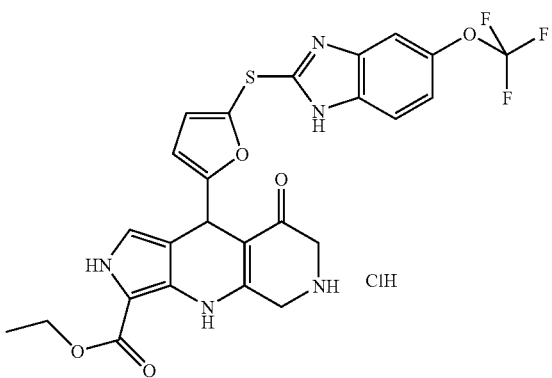

Boc-Protected Intermediate Preparation:

A mixture of 3-amino-2-ethoxycarbonyl-pyrrole (0.148 g, 0.96 mmol), 5-(5-trifluoromethoxy-1H-benzoimidazol-2-ylsulfanyl)-furan-2-carbaldehyde (described in example 150, 0.315 g, 0.96 mmol) and N-Boc-3,5-diketopiperidine (0.205 g, 0.96 mmol) in 5 ml of 1-butanol is heated at reflux temperature for 4 hours. The reaction mixture is then concentrated under reduced pressure and the residue is purified on a silica gel column (40 g) eluted successively with cyclohexane/ethyl acetate (7/3, v/v) and cyclohexane/ethyl acetate (1/1, v/v) to yield 650 mg of 6-tert-butyloxy-8-oxo-9-[5-(5-trifluoromethoxy-1H-benzimidazol-2-ylsulfanyl)-furan-2-yl]-2,4,5,7,8,9-hexahydro-pyrrolo[3,4-b][1,7]naphthyridine-3-carboxylic acid ethyl ester. Quantitative yield. Analytical LC/MS (method B): retention time=4.53 min., m/z=660.00 (positive ion mode).

A solution of 6-tert-butyloxy-8-oxo-9-[5-(5-trifluoromethoxy-1H-benzimidazol-2-ylsulfanyl)-furan-2-yl]-2,4,5,7,8,9-hexahydro-pyrrolo[3,4-b][1,7]naphthyridine-3-carboxylic acid ethyl ester (0.65 g, 0.98 mmol) in dioxane (20 ml) is combined with 4N HCl in dioxane (3.57 ml). The reaction mixture is stirred at room temperature for 16 hours. The formed insoluble material is collected by filtration, washed with dioxane (100 ml), pentane (50 ml) and dried under vacuum to yield 350 mg of 8-oxo-9-[5-(5-trifluoromethoxy-1H-benzimidazol-2-ylsulfanyl)-furan-2-yl]-4,5,6,7,8,9-hexahydro-2H-pyrrolo[3,4-b][1,7]naphthyridine-3-carboxylic acid ethyl ester hydrochloride as a light brown powder. Yield=64%. Analytical LC/MS (method C): m/z=558 (negative ion mode [M−H]$^−$), m/z=560 (positive ion mode [M+H]$^+$).

400 MHz 1H NMR on a BRUKER AVANCE DRX-400 spectrometer, chemical shifts (δ in ppm) in d6 dimethylsufoxyde (DMSO-d6) solvent referenced at 2.50 ppm at 303K temperature: 1.29 (t, J=7.0 Hz, 3H); 3.77 (m, 2H); 4.25 (m partially masked, 1H); 4.28 (q, J=7.0 Hz, 2H); 4.44 (d broad, J=16.5 Hz, 1H); 5.22 (s, 1H); 6.30 (d, J=3.5 Hz, 1H); 6.87 (d, J=3.5 Hz, 1H); 6.91 (d broad, J=3.5 Hz, 1H); 7.16 (d broad, J=8.5 Hz, 1H); 7.49 (s broad, 1H); 7.56 (d broad, J=8.5 Hz, 1H); 9.39 (s, 1H); 9.67 (m broad, 1H); 9.80 (m broad, 1H); 11.65 (s broad, 1H).

A product of the invention may be useful for inhibiting the in vitro activity of an Aurora A and/or B kinase.

Experimental Protocols Regarding the Biochemical Tests Aurora 1 and 2 (Respectively. Aurora B and A)

The inhibitory effect of compounds with respect to the Aurora 1 and 2 kinases is determined with a radioactivity scintillation assay using nickel chelate.

The kinase activity of Aurora is measured by the phosphorylation of NuMA-histidine substrate in the presence of radiolabelled ATP ($[^{33}P]$ ATP) using 96 well Flash plates where the nickel-chelate is linked to the surface of the microplate. The amount of $^{33}P$ incorporated to the substrate NuMA is proportional to the aurora activity.

Proteins:

The protein production has been made in the protein production group of Sanofi-Aventis.
- Aurora-A: the full length recombinant protein including an N-terminal poly-histidine tail has been expressed in *E. coli* and purified to 82%.
- Aurora-B: the full length protein (His tagged in N-terminal) has been co expressed in SF9 cells with the C3 fragment of INCEP protein fused to GST protein. The complex has been purified using the N-terminal poly-histidine tail to 50% homogeneity.
- NuMA, (a nuclear protein which binds to the mitotic system): fragment of 424 amino acids (position 1687-2101) has been expressed in *E. coli* (tagged on the N-terminal end with a poly-histidine tail for use as a the substrate for both Aurora enzymes.

Protocol:

The Flash plates used are nickel-chelate 96 well plates (Perkin Elmer, model SMP107).

The products to be evaluated are incubated in a 100 μl reaction volume per well in the presence of 10 nM of Aurora-B or Aurora-A, 500 nM of NuMA substrate in the following buffer: 50 mM of NaCl, 5 mM MgCl2, (Aurora-B) or 10 mM MgCl2 (Aurora-A) and 1 mM of DTT at 37° C.

80 μL of enzyme/substrate incubation buffer is distributed in each well, followed by 10 μL of solution of compound to be measured with various concentrations. The reaction is started by adding 1 μM of ATP (final concentration) containing 0.2 μCi of $[^{33}P]$ ATP (10 μL). After 30 minutes of incubation the reaction is stopped by removal of the reaction mixture and each well is washed twice with 300 μl of buffer Tris/HCl. The radioactivity is measured in each well using a Packard Top count scintillation counter instrument.

The enzymatic activity is expressed as counts per minute obtained in 30 minutes after subtraction of the background noise (reaction medium without enzyme). The measurement is expressed as percentage of inhibition of Aurora activity versus the control. To generate IC50 values, compounds of the invention are tested at different concentration and the percentage of inhibition are plotted as function of compound concentration, IC50s are calculated using the Xlfit 4 curve fitting software.

| Example # | Aurora2 IC50 (nM) | Aurora1 IC50 (nM) |
|---|---|---|
| 1 | 7448 | |
| 2 | 2739 | |
| 3 | 37 | 8 |
| 4 | 15 | 4 |
| 5 | 9873 | |
| 7 | 302 | |
| 8 | 696 | |
| 9 | 1330 | |
| 10 | 6288 | |
| 11 | 1128 | |
| 12 | 599 | |
| 13 | 5082 | |
| 16 | 1085 | |
| 17 | 888 | |
| 18 | 2151 | |
| 19 | 8394 | |
| 20 | 100 | 83 |
| 22 | 2323 | |
| 23 | 2410 | |
| 24 | 291 | |
| 25 | 3070 | |
| 26 | 1026 | |
| 27 | 4922 | |
| 28 | 17 | 5 |
| 29 | 100 | 36 |
| 30 | 20 | 5 |
| 31 | 14 | 4 |
| 32 | 125 | 50 |
| 33 | 179 | 32 |
| 34 | 23 | 5 |
| 35 | 19 | 5 |
| 36 | 41 | 11 |
| 37 | 29 | 7 |
| 38 | 18 | 7 |
| 39 | 134 | 38 |
| 40 | | 3400 |
| 41 | 29 | 10 |
| 42 | 508 | 17 |
| 43 | 9700 | |
| 45 | 887 | 43 |
| 50 | 227 | |
| 52 | 1939 | 145 |
| 53 | 7371 | |
| 54 | 6097 | |
| 55 | 7198 | |
| 59 | 2217 | 136 |
| 60 | 6500 | |
| 63 | 3300 | |
| 64 | 4100 | |
| 65 | 630 | |
| 67 | 2000 | |
| 70 | 31 | 8 |
| 71 | 187 | 15 |
| 72 | 20 | 6 |
| 73 | 35 | 55 |
| 74 | 302 | 521 |
| 75 | 73 | 183 |
| 76 | 46 | 9 |
| 77 | 2480 | 473 |
| 78 | 331 | 121 |
| 79 | 70 | 15 |
| 80 | 495 | 41 |
| 81 | 33 | 11 |
| 82 | 1336 | 150 |
| 83 | | 5020 |
| 84 | 947 | 177 |
| 85 | 22 | 9 |
| 86 | 82 | 17 |
| 87 | 22 | 8 |
| 88 | 362 | 91 |
| 89 | 355 | 31 |
| 90 | 670 | 194 |
| 91 | 156 | 86 |
| 92 | 2091 | 233 |
| 93 | 1364 | 156 |
| 94 | 9805 | 1223 |
| 95 | 61 | 9 |
| 96 | 58 | 23 |
| 97 | 292 | 47 |
| 98 | 338 | 231 |
| 99 | 135 | 124 |
| 100 | 5441 | 5428 |
| 101 | 1712 | 60 |
| 102 | 596 | 45 |
| 103 | 4721 | 299 |
| 104 | 9 | 7 |

-continued

| Example # | Aurora2 IC50 (nM) | Aurora1 IC50 (nM) |
|---|---|---|
| 105 | 8 | 7 |
| 106 | 17 | 31 |
| 107 | 2941 | 2578 |
| 108 | 41 | 8 |
| 109 | 63 | 17 |
| 110 | 21 | 8 |
| 111 | 1254 | 501 |
| 112 | 31 | 12 |
| 113 | 112 | 23 |
| 114 | 22 | 6 |
| 115 | 48 | 8 |
| 116 | 54 | 6 |
| 117 | 3092 | 194 |
| 119a (+) | 4 | 3 |
| 119b (−) | 738 | 483 |
| 120a (+) | 24 | 4 |
| 120b (−) | 578 | 75 |
| 121 | 10 | 7 |
| 122 | 22 | 7 |
| 123 | 813 | 72 |
| 124 | 20 | 15 |
| 125 | 23 | 11 |
| 126 | 41 | 13 |
| 127 | 566 | 93 |
| 128 | 114 | 17 |
| 129 | 34 | 10 |
| 130 | 434 | 37 |
| 131 | 82 | 10 |
| 132 | 114 | 14 |
| 133 | 31 | 5 |
| 134 | 525 | 47 |
| 135 | 120 | 22 |
| 136 | 18 | 12 |
| 137 | 205 | 93 |
| 138 | 8 | 6 |
| 139 | 124 | 19 |
| 140 | 3902 | 1663 |
| 141 | 87 | 20 |
| 142 | 8 | 3 |
| 143 | 26 | 7 |
| 144 | 28 | 6 |
| 145 | 131 | 16 |
| 146 | 41 | 6 |
| 147 | 67 | 9 |
| 148 | 15 | 11 |
| 149 | 55 | 11 |
| 150 | 29 | 19 |
| 151 | 60 | 14 |

What is claimed is:

1. A compound of formula (I):

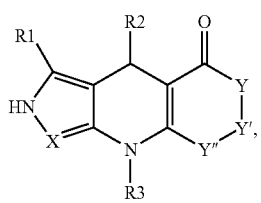

wherein:
R1 represents H or methyl;
R2 represents phenyl, or furyl or thienyl;
R3 represents H or R4;
X is N;
Y, and Y":
  each independently represent a substituent selected from $CH_2$, CHR5, CR5R6, or C=O;
Y' is NH or NR7;
R4 and R7 each independently represents a substituent selected from R8, —COOR8, COR8, and CONHR8;
R5 and R6 each independently represent R8;
R8 represents H or optionally substituted: -alkyl, -alkyl-alkylene, -alkylene, -heterocycloalkyl, -cycloalkyl, -aryl, -heteroaryl, -alkyl-heterocycloalkyl, -alkyl-cycloalkyl, -alkyl-aryl, -alkyl-heteroaryl, or -alkyl-NRaRb, wherein Ra and Rb each independently represent H or alkyl; or
a tautomer, racemate, enantiomer, or diastereomer of said compound or an inorganic or organic acid addition salt or an inorganic or organic base addition salt of said compound, tautomer, racemate, enantiomer, or diastereomer.

2. A compound according to claim 1 wherein R1 is H; or
a tautomer, racemate, enantiomer, or diastereomer of said compound or an inorganic or organic acid addition salt or an inorganic or organic base addition salt of said compound, tautomer, racemate, enantiomer, or diastereomer.

3. A compound according to claim 1, wherein R3 is H; or
a tautomer, racemate, enantiomer, or diastereomer of said compound or an inorganic or organic acid addition salt or an inorganic or organic base addition salt of said compound, tautomer, racemate, enantiomer, or diastereomer.

4. A compound according to claim 1, wherein Y" and Y are $CH_2$; or
a tautomer, racemate, enantiomer, or diastereomer of said compound or an inorganic or organic acid addition salt or an inorganic or organic base addition salt of said compound, tautomer, racemate, enantiomer, or diastereomer.

5. A compound according to claim 1, wherein Y' is NR7; or
a tautomer, racemate, enantiomer, or diastereomer of said compound or an inorganic or organic acid addition salt or an inorganic or organic base addition salt of said compound, tautomer, racemate, enantiomer, or diastereomer.

6. A compound according to claim 1 of formula (Ia)

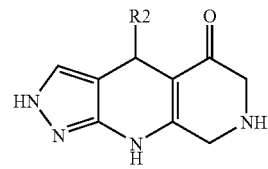

wherein R2 is a substituted phenyl group; or
a tautomer, racemate, enantiomer, or diastereomer of said compound or an inorganic or organic acid addition salt or an inorganic or organic base addition salt of said compound, tautomer, racemate, enantiomer, or diastereomer.

7. A compound according to claim 1 of formula (Ia)

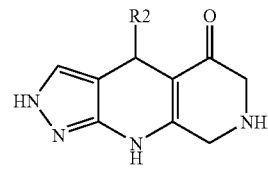

wherein R2 is a substituted thienyl or furyl group; or
a tautomer, racemate, enantiomer, or diastereomer of said compound or an inorganic or organic acid addition salt or an inorganic or organic base addition salt of said compound, tautomer, racemate, enantiomer, or diastereomer.

8. A compound according to claim 1 of formula (Ia)

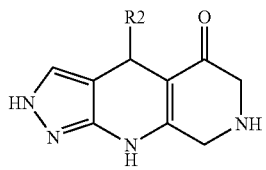

(Ia)

wherein R2 is a substituted phenyl or substituted thienyl or furyl wherein the substitution includes one to four substituents chosen from halogen, alkyl, OH, OR8, $CH_2$—OR8, SH, SR8, $NH_2$, NHR8, CONHR8, CONHCH2R8, NHCOR8, NHCONHR8, $SO_2^-$NHR8, unsubstituted phenyl, and phenyl substituted by alkyl, OH, or halogen; and R8 represents H or optionally substituted: -alkyl, -alkyl-alkylene, -alkylene, -heterocycloalkyl, -cycloalkyl, -aryl, -heteroaryl, -alkyl-heterocycloalkyl, -alkyl-cycloalkyl, -alkyl-aryl, -alkyl-heteroaryl, or -alkyl-NRaRb, wherein Ra and Rb each independently represent H or alkyl; or a tautomer, racemate, enantiomer, or diastereomer of said compound or an inorganic or organic acid addition salt or an inorganic or organic base addition salt of said compound, tautomer, racemate, enantiomer, or diastereomer.

9. A compound according to claim 1, wherein R2 is phenyl or furyl or thienyl substituted by SR8, wherein R8 represents H or optionally substituted: -alkyl, -alkyl-alkylene, -alkylene, -heterocycloalkyl, -cycloalkyl, -aryl, -heteroaryl, -alkyl-heterocycloalkyl, -alkyl-cycloalkyl, -alkyl-aryl, -alkyl-heteroaryl, or -alkyl-NRaRb, wherein Ra and Rb each independently represent H or alkyl; or a tautomer, racemate, enantiomer, or diastereomer of said compound or an inorganic or organic acid addition salt or an inorganic or organic base addition salt of said compound, tautomer, racemate, enantiomer, or diastereomer.

10. A compound according to claim 9, wherein R2 is furyl or thienyl substituted by SR8; or a tautomer, racemate, enantiomer, or diastereomer of said compound or an inorganic or organic acid addition salt or an inorganic or organic base addition salt of said compound, tautomer, racemate, enantiomer, or diastereomer.

11. A compound according to claim 1, wherein R2 is furyl or thienyl substituted by SR8, wherein R8 is a unsubstituted benzimidazolyl or an unsubstituted imidazolyl or a substituted benzimidazolyl or substituted imidazolyl wherein said substituted benzimidzolyl or imidazolyl is substituted by one to four substituents independently chosen from F, Cl, Br, OH, SH, $CF_3$, $OCF_3$, $OCH_3$, $SCF_3$, $SCH_3$, $OCHF_2$, $OCH_2F$, $SCH_2F$, (C1-C6)-alkyl, O-allyl, phenyl, and phenyl substituted with halogen; or a tautomer, racemate, enantiomer, or diastereomer of said compound or an inorganic or organic acid addition salt or an inorganic or organic base addition salt of said compound, tautomer, racemate, enantiomer, or diastereomer.

12. A compound according to claim 1 wherein R5 and R6 are both hydrogen or both methyl; or a tautomer, racemate, enantiomer, or diastereomer of said compound or an inorganic or organic acid addition salt or an inorganic or organic base addition salt of said compound, tautomer, racemate, enantiomer, or diastereomer.

13. A compound according to claim 1 wherein R5 is hydrogen and R6 is a (C1-C6)-alkyl substituted or not substituted, or a phenyl substituted or not substituted; or a tautomer, racemate, enantiomer, or diastereomer of said compound or an inorganic or organic acid addition salt or an inorganic or organic base addition salt of said compound, tautomer, racemate, enantiomer, or diastereomer.

14. A compound according to claim 1 wherein R7 is a —$CO_2Et$ group; or a tautomer, racemate, enantiomer, or diastereomer of said compound or an inorganic or organic acid addition salt or an inorganic or organic base addition salt of said compound, tautomer, racemate, enantiomer, or diastereomer.

15. A compound according to claim 1 which is 4-(4-Hydroxy-3-methyl-phenyl)-2,4,6,7,8,9-hexahydro-pyrazolo[3,4-b]-1,7-naphthyridin-5-one;

4-[3-(4-Chloro-phenoxy)-phenyl]-2,4,6,7,8,9-hexahydro-pyrazolo[3,4-b]-1,7-naphthyridin-5-one;

4-(2-Fluoro-phenyl)-2,4,6,7,8,9-hexahydro-pyrazolo[3,4-b]-1,7-naphthyridin-5-one;

4-(4-Phenoxy-phenyl)-2,4,6,7,8,9-hexahydro-pyrazolo[3,4-b]-1,7-naphthyridin-5-one;

4-[3-(3,5-Dichloro-phenoxy)-phenyl]-2,4,6,7,8,9-hexahydro-pyrazolo[3,4-b]-1,7-naphthyridin-5-one;

4-[3-(4-tert-Butyl-phenoxy)-phenyl]-2,4,6,7,8,9-hexahydro-pyrazolo[3,4-b]-1,7-naphthyridin-5-one;

4-[3-(4-trifluoromethyl-phenyloxy)-phenyl]-2,4,6,7,8,9-hexahydro-pyrazolo[3,4-b]-1,7-naphthyridin-5-one;

4-[3-(4-Methoxy-phenoxy)-phenyl]-2,4,6,7,8,9-hexahydro-pyrazolo[3,4-b]-1,7-naphthyridin-5-one;

4-(3-p-Tolyloxy-phenyl)-2,4,6,7,8,9-hexahydro-pyrazolo[3,4-b]-1,7-naphthyridin-5-one;

4-[3-(3,4-Dichloro-phenoxy)-phenyl]-2,4,6,7,8,9-hexahydro-pyrazolo[3,4-b]-1,7-naphthyridin-5-one;

4-(3-Phenoxy-phenyl)-2,4,6,7,8,9-hexahydro-pyrazolo[3,4-b]-1,7-naphthyridin-5-one;

4-[3-(4-Chloro-phenoxy)-phenyl]-3-methyl-2,4,6,7,8,9-hexahydro-pyrazolo[3,4-b]-1,7-naphthyridin-5-one;

4-[2-(4-Chloro-phenoxy)-phenyl]-2,4,6,7,8,9-hexahydro-pyrazolo[3,4-b]-1,7-naphthyridin-5-one;

4-[5-(4-Chloro-phenyl)-furan-2-yl]-2,4,6,7,8,9-hexahydro-pyrazolo[3,4-b]-1,7-naphthyridin-5-one;

4-[5-(2-trifluoromethyl-phenyl)-furan-2-yl]-2,4,6,7,8,9-hexahydro-pyrazolo[3,4-b]-1,7-naphthyridin-5-one;

4-[5-(3-trifluoromethyl-phenyl)-furan-2-yl]-2,4,6,7,8,9-hexahydro-pyrazolo[3,4-b]-1,7-naphthyridin-5-one;

4-[5-(3,4-Dichloro-phenoxymethyl)-furan-2-yl]-2,4,6,7,8,9-hexahydro-pyrazolo[3,4-b]-1,7-naphthyridin-5-one;

4-[5-(1H-Benzimidazol-2-ylsulfanyl)-furan-2-yl]-2,4,6,7,8,9-hexahydro-pyrazolo[3,4-b]-1,7-naphthyridin-5-one;

4-(2-Allyloxy-phenyl)-2,4,6,7,8,9-hexahydro-pyrazolo[3,4-b]-1,7-naphthyridin-5-one;

4-[5-(1H-Benzimidazol-2-ylsulfanyl)-furan-2-yl]-7-(tert-butyloxycarbonyl)-2,4,6,7,8,9-hexahydro-pyrazolo[3,4-b]-1,7-naphthyridin-5-one;

4-[5-(1H-Benzimidazol-2-ylsulfanyl)-furan-2-yl]-7-(2-hydroxy-3-piperidin-1-yl-propyl)-2,4,6,7,8,9-hexahydro-pyrazolo[3,4-b]-1,7-naphthyridin-5-one;

4-[3-(4-Chloro-phenoxy)-phenyl]-7-(2-hydroxy-3-morpholin-4-yl-propyl)-2,4,6,7,8,9-hexahydro-pyrazolo[3,4-b]-1,7-naphthyridin-5-one;

4-[5-(1H-Benzimidazol-2-ylsulfanyl)-furan-2-yl]-9-(2-hydroxy-3-morpholin-4-yl-propyl)-2,4,6,7,8,9-hexahydro-pyrazolo[3,4-b]-1,7-naphthyridin-5-one;

4-[3-(4-Chloro-phenoxy)-phenyl]-7-(3,5-dimethyl-isoxazole-4-carbonyl)-2,4,6,7,8,9-hexahydro-pyrazolo[3,4-b]-1,7-naphthyridin-5-one, 4-[3-(4-Chloro-phenoxy)-phenyl]-7-(isoxazole-5-carbonyl)-2,4,6,7,8,9-hexahydro-pyrazolo[3,4-b]-1,7-naphthyridin-5-one;

4-[3-(4-Chloro-phenoxy)-phenyl]-7-(4-methyl-[1,2,3]thia-diazole-5-carbonyl)-2,4,6,7,8,9-hexahydro-pyrazolo[3,4-b]-1,7-naphthyridin-5-one;

4-[3-(4-Chloro-phenoxy)-phenyl]-7-(6-chloro-pyridine-2-carbonyl)-2,4,6,7,8,9-hexahydro-pyrazolo[3,4-b]-1,7-naphthyridin-5-one;

7-Acetyl-4-[3-(4-chloro-phenoxy)-phenyl]-2,4,6,7,8,9-hexahydro-pyrazolo[3,4-b]-1,7-naphthyridin-5-one;

9-Acetyl-4-[3-(4-chloro-phenoxy)-phenyl]-2,4,6,7,8,9-hexahydro-pyrazolo[3,4-b]-1,7-naphthyridin-5-one;

3-(5-oxo-2,4,6,7,8,9-hexahydro-pyrazolo[3,4b]-1,7-naphthyridin-4-yl)-N-(4-trifluoromethoxy-benzyl)-benzamide;

3-(5-oxo-2,4,6,7,8,9-hexahydro-pyrazolo[3,4b]-1,7-naphthyridin-4-yl)-N-(3-trifluoromethoxy-benzyl)-benzamide;

4-(5-oxo-2,4,6,7,8,9-hexahydro-pyrazolo[3,4b]-1,7-naphthyridin-4-yl)-N-(3-trifluoromethoxy-phenyl)-benzamide;

3-(5-oxo-2,4,6,7,8,9-hexahydro-pyrazolo[3,4b]-1,7-naphthyridin-4-yl)-N-(4-trifluoromethoxy-phenyl)-benzamide;

3-(5-oxo-2,4,6,7,8,9-hexahydro-pyrazolo[3,4b]-1,7-naphthyridin-4-yl)-N-(3-trifluoromethoxy-phenyl)-benzamide;

4-Chloro-N-[3-(5-oxo-2,4,6,7,8,9-hexahydro-pyrazolo[3,4b]-1,7-naphthyridin-4-yl)-phenyl]-benzamide;

1-(4-Chloro-phenyl)-3-[3-(5-oxo-2,4,6,7,8,9-hexahydro-pyrazolo[3,4b]-1,7-naphthyridin-4-yl)-phenyl]-urea;

4-(5-Oxo-2,4,6,7,8,9-hexahydro-pyrazolo[3,4b]-1,7-naphthyridin-4-yl)-N-(4-trifluoromethoxy-phenyl)-benzenesulfonamide;

N-(4-Chloro-phenyl)-4-(5-oxo-2,4,6,7,8,9-hexahydro-pyrazolo[3,4b]-1,7-naphthyridin-4-yl)-benzenesulfonamide;

4-[5-(5-Methyl-1H-benzimidazol-2-ylsulfanyl)-furan-2-yl]-2,4,6,7,8,9-hexahydro-pyrazolo[3,4-b]-1,7-naphthyridin-5-one;

4-[5-(5-Chloro-benzothiazol-2-ylsulfanyl)-furan-2-yl]-2,4,6,7,8,9-hexahydro-pyrazolo[3,4-b]-1,7-naphthyridin-5-one;

4-[5-(5-Methoxy-1H-benzimidazol-2-ylsulfanyl)-furan-2-yl]-2,4,6,7,8,9-hexahydro-pyrazolo[3,4-b]-1,7naphthyridin-5-one;

4-[5-(1-Methyl-1H-benzimidazol-2-ylsulfanyl)-furan-2-yl]-2,4,6,7,8,9-hexahydro-pyrazolo[3,4-b]-1,7-naphthyridin-5-one;

4-[5-(5,6-Dichloro-1H-benzoimidazol-2-ylsulfanyl)-furan-2-yl]-2,4,6,7,8,9-hexahydro-pyrazolo[3,4-b]-1,7-naphthyridin-5-one;

4-{5-[5-(4-Chloro-phenyl)-1-methyl-1H-imidazol-2-ylsulfanyl]-furan-2-yl}-2,4,6,7,8,9-hexahydro-pyrazolo[3,4-b]-1,7-naphthyridin-5-one;

4-[5-(5-Chloro-1H-benzoimidazol-2-ylsulfanyl)-furan-2-yl]-2,4,6,7,8,9-hexahydro-pyrazolo[3,4-b]-1,7-naphthyridin-5-one;

4-[5-(4,5-Dimethyl-1H-imidazol-2-ylsulfanyl)-furan-2-yl]-2,4,6,7,8,9-hexahydro-pyrazolo[3,4-b]-1,7-naphthyridin-5-one;

4-[5-(5-Methyl-1H-benzoimidazol-2-ylsulfanyl)-thiophen-2-yl]-2,4,6,7,8,9-hexahydro-pyrazolo[3,4-b]-1,7-naphthyridin-5-one;

9-[5-(1H-Benzimidazol-2-ylsulfanyl)-furan-2-yl]-8-oxo-4,5,6,7,8,9-hexahydro-2H-pyrrolo[3,4-b]-1,7-naphthyridine-3-carboxylic acid ethyl ester;

9-[5-(6-Methoxy-1H-benzimidazol-2-ylsulfanyl)-furan-2-yl]-8-oxo-4,5,6,7,8,9-hexahydro-2H-pyrrolo[3,4-b][1,7]naphthyridine-3-carboxylic acid ethyl ester;

9-[5-(3H-Imidazo[4,5-b]pyridin-2-ylsulfanyl)-furan-2-yl]-8-oxo-4,5,6,7,8,9-hexahydro-2H-pyrrolo[3,4-b][1,7]naphthyridine-3-carboxylic acid ethyl ester;

9-[5-(5,6-Difluoro-1H-benzimidazol-2-ylsulfanyl)-furan-2-yl]-8-oxo-4,5,6,7,8,9-hexahydro-2H-pyrrolo[3,4-b][1,7]naphthyridine-3-carboxylic acid ethyl ester;

9-[5-(5-Hydroxy-1H-benzimidazol-2-ylsulfanyl)-furan-2-yl]-8-oxo-4,5,6,7,8,9-hexahydro-2H-pyrrolo[3,4-b]-1,7-naphthyridine-3-carboxylic acid ethyl ester;

6-tert-Butyloxy-9-[5-(5-Difluoromethoxy-1H-benzimidazol-2-ylsulfanyl)-furan-2-yl]-8-oxo-2,4,5,7,8,9-hexahydro-pyrrolo[3,4-b]-1,7-naphthyridine-3-carboxylic acid ethyl ester;

9-[5-(5-Difluoromethoxy-1H-benzimidazol-2-ylsulfanyl)-furan-2-yl]-8-oxo-4,5,6,7,8,9-hexahydro-2H-pyrrolo[3,4-b]-1,7-naphthyridine-3-carboxylic acid ethyl ester;

6-tert-Butyloxy-9-[5-(5-chloro-1H-benzimidazol-2-ylsulfanyl)-furan-2-yl]-8-oxo-2,4,5,7,8,9-hexahydro-pyrrolo[3,4-b]-1,7-naphthyridine-3-carboxylic acid ethyl ester;

9-[5-(5-Chloro-1H-benzimidazol-2-ylsulfanyl)-furan-2-yl]-8-oxo-4,5,6,7,8,9-hexahydro-2H-pyrrolo[3,4-b]-1,7-naphthyridine-3-carboxylic acid ethyl ester;

6-tert-Butyloxy-9-[5-(5-chloro-6-methyl-1H-benzimidazol-2-ylsulfanyl)-furan-2-yl]-8-oxo-2,4,5,7,8,9-hexahydro-pyrrolo[3,4-b]-1,7-naphthyridine-3-carboxylic acid ethyl ester;

9-[5-(5-Chloro-6-methyl-1H-benzimidazol-2-ylsulfanyl)-furan-2-yl]-8-oxo-4,5,6,7,8,9-hexahydro-2H-pyrrolo[3,4-b]-1,7-naphthyridine-3-carboxylic acid ethyl ester;

6-tert-Butyloxy-9-[5-(5-chloro-7-methyl-1H-benzimidazol-2-ylsulfanyl)-furan-2-yl]-8-oxo-2,4,5,7,8,9-hexahydro-pyrrolo[3,4-b]-1,7-naphthyridine-3-carboxylic acid ethyl ester;

9-[5-(5-Chloro-7-methyl-1H-benzimidazol-2-ylsulfanyl)-furan-2-yl]-8-oxo-4,5,6,7,8,9-hexahydro-2H-pyrrolo[3,4-b]-1,7-naphthyridine-3-carboxylic acid ethyl ester;

6-tert-Butyloxy-9-[5-(2,2-difluoro-5H-[1,3]dioxolo[4',5':4,5]benzo[1,2-d]imidazol-6-ylsulfanyl)-furan-2-yl]-8-oxo-2,4,5,7,8,9-hexahydro-pyrrolo[3,4-b]-1,7-naphthyridine-3-carboxylic acid ethyl ester;

9-[5-(2,2-Difluoro-5H-[1,3]dioxolo[4',5':4,5]benzo[1,2-d]imidazol-6-ylsulfanyl)-furan-2-yl]-8-oxo-4,5,6,7,8,9-hexahydro-2H-pyrrolo[3,4-b]-1,7-naphthyridine-3-carboxylic acid ethyl ester;

9-[5-(4,6-Difluoro-1H-benzimidazol-2-ylsulfanyl)-furan-2-yl]-8-oxo-4,5,6,7,8,9-hexahydro-2H-pyrrolo[3,4-b]quinoline-3-carboxylic acid ethyl ester;

9-[5-(5,7-Difluoro-1H-benzimidazol-2-ylsulfanyl)-furan-2-yl]-8-oxo-4,5,6,7,8,9-hexahydro-2H-pyrrolo[3,4-b]-1,7-naphthyridine-3-carboxylic acid ethyl ester;

4-[5-(5,7-Difluoro-1H-benzimidazol-2-ylsulfanyl)-furan-2-yl]-2,4,6,7,8,9-hexahydro-pyrazolo[3,4b]-1,7-naphthyridin-5-one;

9-[5-(6-Chloro-5-fluoro-1H-benzimidazol-2-ylsulfanyl)-furan-2-yl]-8-oxo-4,5,6,7,8,9-hexahydro-2H-pyrrolo[3,4-b]-1,7-naphthyridine-3-carboxylic acid ethyl ester;

9-[5-(5-Fluoro-1H-benzimidazol-2-ylsulfanyl)-furan-2-yl]-8-oxo-4,5,6,7,8,9-hexahydro-2H-pyrrolo[3,4-b]-1,7-naphthyridine-3-carboxylic acid ethyl ester;

8-Oxo-9-[5-(5-trifluoromethoxy-1H-benzimidazol-2-ylsulfanyl)-furan-2-yl]-4,5,6,7,8,9-hexahydro-2H-pyrrolo[3,4-b][1,7]naphthyridine-3-carboxylic acid ethyl ester; or a tautomer, racemate, enantiomer, or diastereomer of said compound or an inorganic or organic acid addition salt or an inorganic or organic base addition salt of said compound, tautomer, racemate, enantiomer, or diastereomer.

16. A pharmaceutical composition comprising a therapeutically effective amount of a compound according to claim 1, in combination with a pharmaceutically effective excipient.

17. A method of inhibiting Aurora kinases A and B, comprising administering an inhibiting amount of the compound according to claim 1.

\* \* \* \* \*